(12) United States Patent
Sikic et al.

(10) Patent No.: US 7,875,274 B2
(45) Date of Patent: Jan. 25, 2011

(54) PROTEIN MODULATORS OF RESISTANCE TO ALKYLATING AGENTS

(75) Inventors: Branimir Sikic, Stanford, CA (US); Markus Bredel, Evanston, IL (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 21 days.

(21) Appl. No.: 11/638,161

(22) Filed: Dec. 13, 2006

(65) Prior Publication Data

US 2007/0148145 A1 Jun. 28, 2007

Related U.S. Application Data

(60) Provisional application No. 60/751,031, filed on Dec. 16, 2005.

(51) Int. Cl.
*A61K 48/00* (2006.01)
*C12Q 1/68* (2006.01)

(52) U.S. Cl. .......................... 424/93.21; 435/6; 977/802

(58) Field of Classification Search ...................... None
See application file for complete search history.

(56) References Cited

U.S. PATENT DOCUMENTS

| | | | |
|---|---|---|---|
| 5,716,785 A | 2/1998 | Van Gelder et al. | |
| 5,807,522 A | 9/1998 | Brown et al. | |
| 5,891,636 A | 4/1999 | Van Gelder et al. | |
| 6,387,699 B1 * | 5/2002 | Bennett et al. | 435/375 |
| 6,410,516 B1 | 6/2002 | Baltimore et al. | |
| 6,973,388 B2 | 12/2005 | Friend et al. | |
| 7,171,311 B2 | 1/2007 | Dai et al. | |
| 2003/0198961 A1 | 10/2003 | Spelsberg et al. | |
| 2003/0215830 A1 | 11/2003 | Tabiti et al. | |
| 2004/0013691 A1 * | 1/2004 | Rosenblum | 424/234.1 |
| 2004/0156854 A1 * | 8/2004 | Mulligan et al. | 424/155.1 |
| 2005/0079496 A1 | 4/2005 | Serfling et al. | |
| 2005/0250137 A1 * | 11/2005 | Tainsky et al. | 435/6 |

OTHER PUBLICATIONS

Esteller et al. (N Engl J Med. 2000; 343(19): 1350-1354).*
Islaih et al. (Environmental and Molecular Mutagenesis. 2004; 44: 401-419).*
Jin et al. (Acta Pharmacologica Sinica. 2004; 25(3): 319-326).*
Dudda-Subramanya et al. (Journal of Experimental Therapeutics and Oncology. 2003; 3: 297-304).*
Bredel et al. ( Journal of clinical Oncology, Jan. 10, 2006; 24(2): 274-287).*
Nakatsu et al. (Mol. Cancer Ther. Mar. 2005; 4(3): 399-412).*
Bredel et al. (Journal of Clinical Oncology. Jan. 2006; 24(2): 274-287).*
Ningya Shi, et al., "Noninvasive gene targeting to the brain," *PNAS*, 2000, vol. 97, No. 13 7567-7572.
Paula Y.P. Lam, et al., "Potential of gene therapy for brain tumors," *Human Molecular Genetics*, 2001, vol. 10, 777-787.
Virginia Goss Tusher, et al., "Significance analysis of microarrays applied to the ionizing radiation response," *PNAS*, Apr. 24, 2001, vol. 98, No. 9, 5116-5121.
Gary Hardiman, "Microarray Technologies—An Overview," *UC-San Diego,*, Mar. 13-15, 2002, 1-5.
William M. Pardridge, et al., "Tyrosine Hydroxylase Replacement in Experimental Parkinson's Disease with Transvascular Gene Therapy," *Journal of the American Society for Experimental NeuroTherapeutics*, Jan. 2005, vol. 2, 129-138.
Markus Bredel, et al., "High-Resolution Genome-Wide Mapping of Genetic Alterations in Human Glial Brain Tumors," *Cancer Res*, May 15, 2005, vol. 65, No. 10, 4088-4096.
Markus Bredel, et al., "Functional Network Analysis Reveals Extended Gliomagenesis Pathway Maps and Three Novel MYC-Interacting Genes in Human Gliomas," *Cancer Res*, Oct. 1, 2005, vol. 65, No. 19, 8679-8689.
Kyle D. Weaver, et al., "Potentiation of chemotherapeutic agents following antagonism of nuclear factor kappa B in human gliomas," *Journal of Clinical Oncology*, Jan. 10, 2006, vol. 24, No. 2, 274-287.
Esteller, et al., "Inactivation of the DNA-Repair Gene MGMT and the Clinical Response of Gliomas to Alkylating Agents," *New England Journal of Medicine*, Nov. 9, 2000, vol. 343, No. 19, 1350-1354.

* cited by examiner

*Primary Examiner*—Scott Long
(74) *Attorney, Agent, or Firm*—David J. Aston; Peters Verny, LLP

(57) ABSTRACT

There is disclosed a method for identifying a therapeutically responsive phenotype, as distinguished, e.g. from an alkylating agent resistant phenotype in a cell, which method may be used to evaluate the likelihood of successful outcome of treating a tumor cell with an alkylating agent. The method is directed to the NF-κB activation in response to DNA damage caused by alkylating agents. It comprises the step of measuring a level of expression of a protein, which participates in the NF-κB pathway. Preferably it comprises measuring the expression of TNFAIP3 in the cell, wherein a resistant phenotype has less expression of TNFAIP3 than a sensitive phenotype. Another particularly significant gene, which predicts survival, is NFKBIA. Other genes whose altered expression level is associated with resistance or prognosis are TNIP1, TNIP2, RIP, NFKBIB, Beta4GalNAc-T4, NFKBIE, C8orf4, LIF, CD44, FBXO32, and SDC1, and these are also measured in certain embodiments.

10 Claims, 19 Drawing Sheets

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
```

-continued aatcttcccc ggtctctgtt                                          20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
taccctgggt gaccctgaag                                          20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
acaccaggtc aggattttgc                                          20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
gctgatgtca atgctcagga                                          20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
tgtgtcgaag tggtagccat g                                        21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
agccaccaag ccatcatcat                                          20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
ttccagtgca gaaccaacag                                          20

```
<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
gtgcagccca taatgaaggt                                              20
```

PROTEIN MODULATORS OF RESISTANCE TO ALKYLATING AGENTS

CROSS-REFERENCE TO RELATED APPLICATIONS

This application claims priority from U.S. Provisional Patent Application No. 60/751,031 filed on Dec. 16, 2005, which is hereby incorporated by reference in its entirety.

FEDERALLY-SPONSORED RESEARCH OR DEVELOPMENT

This invention was made with U.S. Government support under contract CA092474 awarded by the National Institutes of Health. The U.S. Government has certain rights in this invention.

REFERENCE TO SEQUENCE LISTING, COMPUTER PROGRAM, OR COMPACT DISK

Applicants assert that the paper copy of the Sequence Listing is identical to the Sequence Listing in computer readable form found on the accompanying computer disk. Applicants incorporate the contents of the sequence listing by reference in its entirety.

BACKGROUND OF THE INVENTION

1. Field of the Invention

The present invention relates to the field of cancer and to the field of evaluation of therapy of diseases, including glioblastoma, and the use of alkylating agents and other therapeutics.

2. Related Art

The prognosis of patients with glioblastoma multiforme has not improved substantially over the past decades and almost all patients succumb to their disease. Current treatment approaches are based on radiation therapy and alkylating agent chemotherapy. $O^6$-guanine alkylating agents, such as 1,3-bis(2-chloroethyl)-1-nitrosourea (BCNU) and temozolomide (TMZ), are among the most widely used chemotherapeutics in treating glioblastomas because they can efficiently cross the blood-brain barrier. These agents have modest efficacy against glioblastomas (Refs 1, 2). A subset of glioblastoma patients demonstrates an initial response, lasting a few or several months and eventually leading to tumor recurrence.

One of the most prominent resistance mechanisms to alkylating agents includes $O^6$-methylguanine DNA methyltransferase (MGMT) (Ref 3), which acts as a suicide enzyme by removing the methyl or chloroethyl damage at the $O^6$-position of guanine. Epigenetic MGMT gene silencing via promoter hypermethylation, present in about 40% of cases, has been shown to predict outcome in glioblastoma patients treated with BCNU or TMZ (Refs. 4, 5).

The growing awareness that resistance in human cancer is likely regulated by the coordinated alteration of molecular pathways (Ref. 6) suggests that many more genes might be involved in the development of resistance phenotypes in glioblastomas than the changes described thus far for a limited number of known resistance genes (Ref. 3). Resistance of glioblastomas to alkylating agents such as BCNU and TMZ seems to follow a more complex pattern than simple dependence on MGMT levels (Refs 3,7-9).

Excessive and prolonged activation of nuclear factor-κB (NF-κB) has been established as a principal mechanism of tumor chemoresistance, which is primarily mediated by its antiapoptotic activity (Refs. 10,11). Some evidence also indicates a link between the NF-κB pathway and resistance of glioblastoma cells to $O^6$-alkylating agents, and suggests that inhibition of NF-κB is a promising means to potentiate the cytotoxic effects of these agents (Ref. 12). The NF-κB complex consists of a family of heterodimers, of which the p50/p65 heterodimer is the most abundant form. NF-κB is active in the nucleus and is inhibited through its sequestration in the cytoplasm by the inhibitors of κB (IκB), primarily through the interaction of IκB proteins with p65. IκB is a target of several well-characterized kinase cascades that activate IκB kinases (IKK), which phosphorylate IκB and mark it for degradation via the ubiquination pathway, thereby allowing activation of NF-κB. Activated NF-κB translocates to the nucleus and binds DNA at κB-binding motifs, which initiates gene transcription. Anticancer drugs are known to induce the expression of NF-κB target genes through the direct activation of NF-κB and the secondary production of NF-κB activators (Ref 11).

There is increasing recognition of the value of comprehensive approaches to the molecular characterization of biological phenotypes such as drug resistance. We have here utilized an integrated model of glioblastoma resistance to $O^6$-alkylating agents and genomics tools to globally explore molecular factors, cellular pathways, and functional interaction networks perturbed during the selection and evolution of drug resistance in glioblastoma cells.

The results described below highlight the involvement of a cellular pathway of NF-κB-mediated resistance to these agents in glioblastoma cells. The contribution of NF-κB to anticancer drug resistance has been described in various in vitro and in vivo resistance models (Ref. 10). The antiapoptotic activity of NF-κB appears to be the most important mode of action mediating the resistance and pro-survival effects of this gene in cancer cells (Refs. 10-13). Genotoxic stress resulting from the exposure of tumor cells to $O^6$-alkylating agents causes DNA damage and leads to the initiation of apoptosis. NF-κB activation abrogates the apoptosis signal in response to these agents (Ref. 10). Antagonism of NF-κB in malignant gliomas has been shown to render glioma cells more susceptible to BCNU via increased apoptosis (Ref. 12), but the DNA damage-induced signaling pathway upstream of IκB has not been identified in these cells.

Cited Patents and Publications

Inactivation of the DNA-Repair Gene MGMT and the Clinical Response of Gliomas to Alkylating Agents, by Esteller, M, et al., *N Engl J Med.* 2000; 343(19): 1350-1354 describes how the DNA-repair enzyme O6-methylguanine-DNA methyltransferase (MGMT) inhibits the killing of tumor cells by alkylating agents. MGMT activity is controlled by a promoter; methylation of the promoter silences the gene in cancer, and the cells no longer produce MGMT. The authors examined gliomas to determine whether methylation of the MGMT promoter is related to the responsiveness of the tumor to alkylating agents. They found that the MGMT promoter was methylated in gliomas from 19 of 47 patients (40 percent). This finding was associated with regression of the tumor and prolonged overall and disease-free survival. It was an independent and stronger prognostic factor than age, stage, tumor grade, or performance status. The authors concluded that methylation of the MGMT promoter in gliomas is a useful predictor of the responsiveness of the tumors to alkylating agents.

US 2005/0287541 to Nakagawara, et al., published Dec. 29, 2005, entitled "Microarray for predicting the prognosis of neuroblastoma and method for predicting the prognosis of neuroblastoma," discloses microarray for predicting the prognosis of neuroblastoma, wherein the microarray has 25 to 45 probes related to good prognosis, which are hybridized to a gene transcript whose expression is increased in a good prognosis patient with neuroblastoma and are selected from 96 polynucleotides.

US 2003/0198961 to Spelsberg, et al., published Oct. 23, 2003, entitled "Determining cancer aggressiveness," discloses methods for determining the aggressiveness of a cancer in a mammal. Specifically, the invention provides methods and methods for measuring the level of a TIEG marker in a sample. Such levels can be correlated with the aggressiveness of a cancer to predict patient outcome and develop treatment regimens.

A list of additional cited references is contained at the end of the specification.

'Cohort I'). Sub-grouping according to unsupervised clustering of patients based on resistance signature. Significant difference in survival distribution between the two subgroups (Group I='favorable' and Group II='unfavorable') according to log-rank test (p=0.019).

Figure 7:
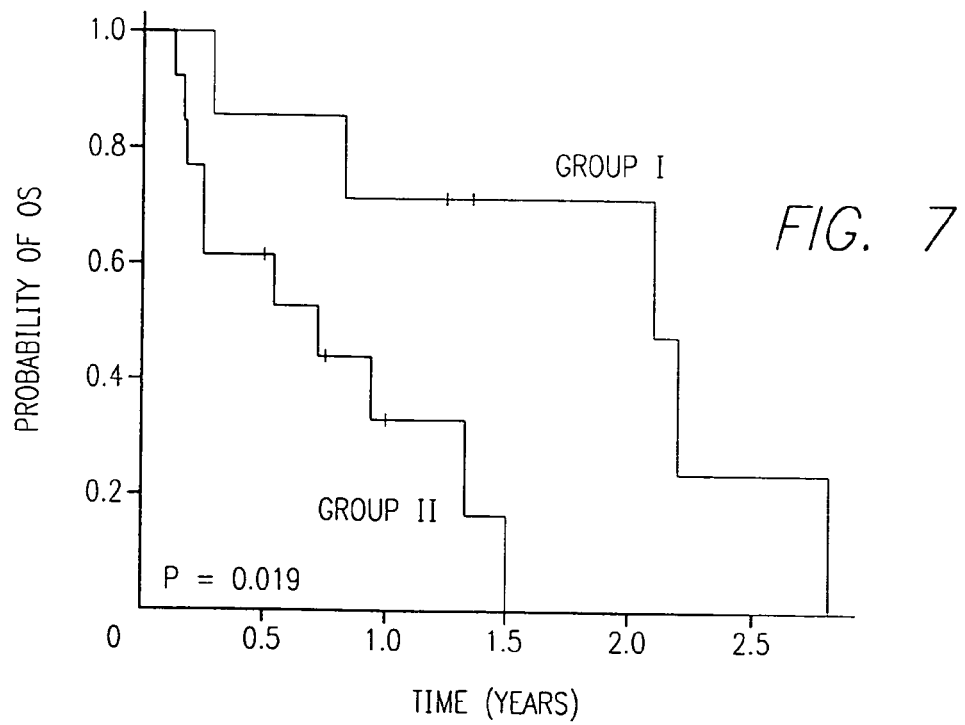
FIG. 7 is a Kaplan-Meier estimate of overall survival in 29 glioblastoma patients (independent validation cohort.
Figure 8A:
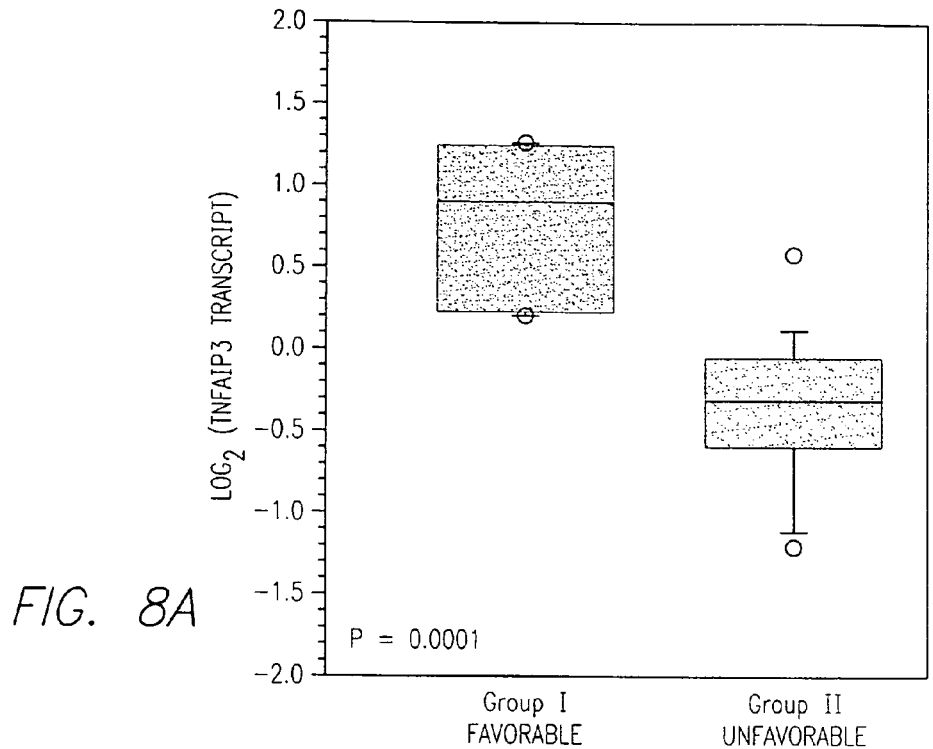
Figure 8B:
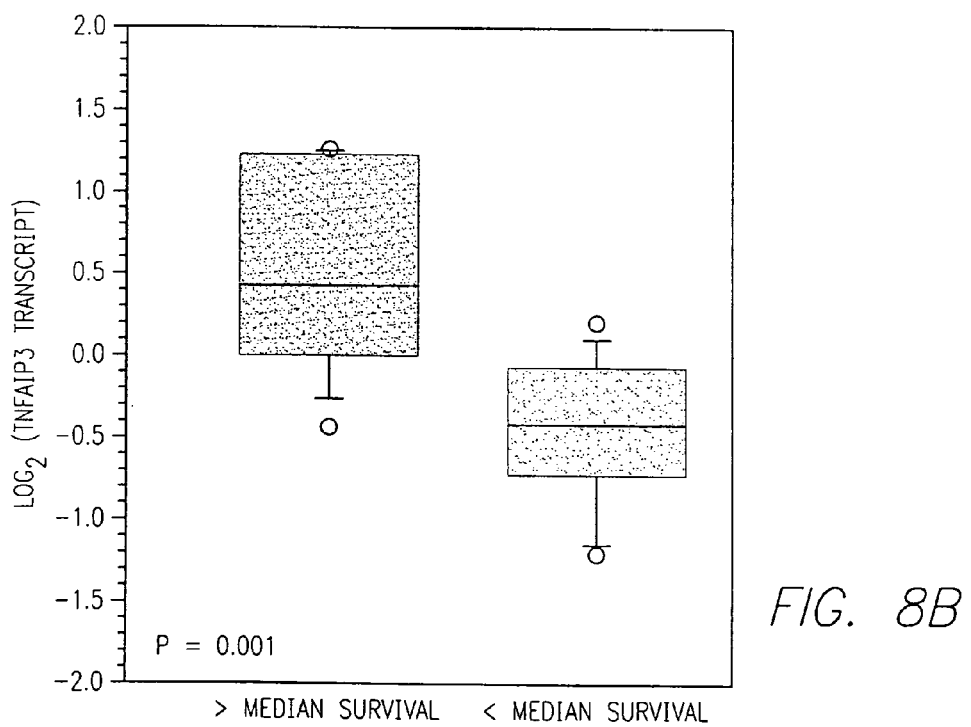

FIGS. 8A and 8B is a pair of graphs showing TNFAIP3 transcript abundance in Cohort I of FIG. 7. 8A, Significantly different TNFAIP3 abundance in the two subgroups of FIG. 7 (p=0.0001, independent t-test) with low abundance present in the unfavorable subgroup ('Group II'). 8B, Significant difference in TNFAIP3 abundance if patients are stratified according to median survival (p=0.001).

FIG. 9 represents TNFAIP3 in continuous and class models in Cohort I. 9A is a graph showing Global Univariate Cox-proportional hazards regression model for 2,188 expressed clones representing about 1,800 genes. TNFAIP3 is the second most significant gene related to patient survival as a continuous variable (p=0.0018). 9B is a Kaplan-Meier estimates of overall survival based on median TNFAIP3 transcript abundance confirm a significant survival link for TNFAIP3 in a class model (p=0.018, log-rank test).

FIG. 10A-D is a series of Kaplan-Meier plots showing NFKBIA performance as a class in Cohorts II+III. A and B are Kaplan-Meier estimates of overall survival stratified based on median NFKBIA abundance and disclose high significance for NFKBIA in non-parallel hazard functions, both in glioblastomas (p=0.0001, log-rank test) and high-grade gliomas (p=0.0008). C and D, NFKBIA outperforms MGMT in predicting patient outcome in two-class models both in glioblastomas (p=0.0001 vs. 0.001, respectively) and high-grade gliomas p=0.0008 vs. 0.032, respectively).

FIG. 11 illustrates NFKBIA/MGMT combined predictor model in Cohorts II+III. 11A is a graph showing Univariate Cox proportional hazards regression analysis based on a rank sum model showed a significantly greater proportional hazard for the gene combination compared to individual genes both in glioblastomas (p=0.000002) and high-grade gliomas (p=0.000008). 11B is a Kaplan-Meier plot of a Class model using the same rank sum model disclosing also a comparably better performance in terms of non-parallel hazard functions for the gene combination compared to the individual genes in glioblastomas (p=0.00004, log-rank test); in these graphs, low risk=NFBBIA is high and MGMT is low, while high risk=NFBBIA is low and MGMT is high.

FIG. 12 illustrates unsupervised sub-classification of tumors based on seven-modulator model in Cohorts II+III. 12A, upper panel shows a heat map and dendrogram resulting from unsupervised hierarchical clustering of 96 glioblastomas (columns) based on the abundance of 7 candidate endogenous modulators (rows) of canonical NFKB activation, namely NFKBIB, IKBG, NFKBIE, TNIP2, NFKBIA, TNIP1, TNFAIP3. The gene dendrogram demonstrates the highly correlated expression pattern of most modulators across the tumor panel. NFKBIA, TNFAIP3, and TNIP1 show the most highly correlated expression patterns. Lower panel is a dendrogram showing stepwise gene elimination in the order of least correlated expression behavior. Actuarial survival analyses of the two major tumor subgroups after re-clustering after each elimination step indicates the significant relationship to patient survival of all predictor models (7-gene to 3-gene models) and the most significant survival link for the 3-gene (NFKBIA, TNFAIP3, TNIP1) predictor. 11B is a Kaplan-Meier estimate and log-rank p for the 3-gene predictor with subgroups (Group I: high modulator abundance, Group II: low modulator abundance) based on the 3-gene re-clustering.

Figure 13:
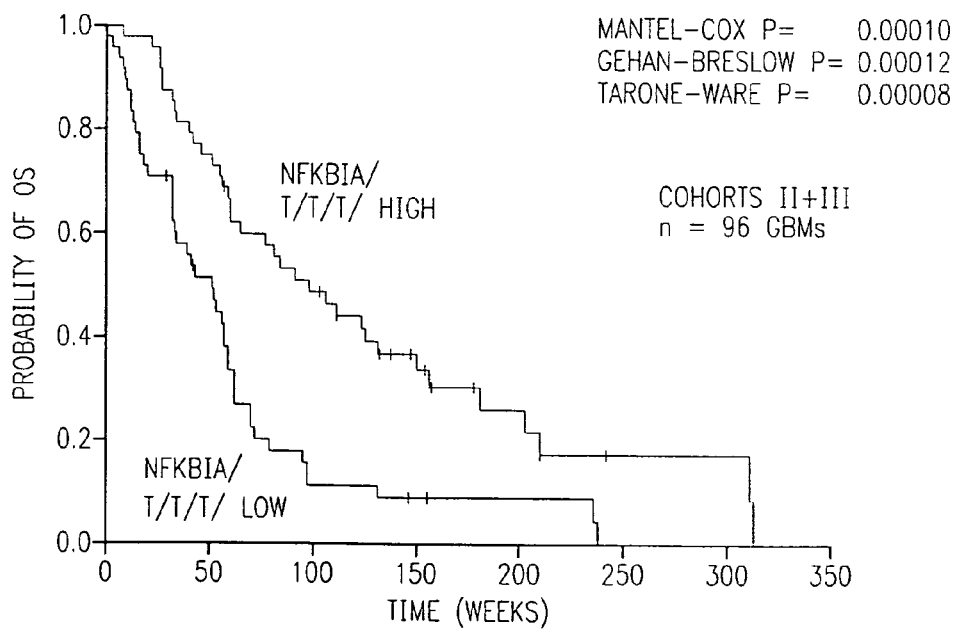

FIG. 13 is a Kaplan-Meier plot illustrating class prediction of glioblastoma survival based on four endogenous NF-κB modulators in Cohorts II+III. Actuarial survival analysis using three different compare factors (Cox-Mantel, Gehan-Breslow, Tarone-Ware) each indicates a significant difference in survival between the two subgroups (above 3+TNIP2) stratified according to median modulator abundance.

DETAILED DESCRIPTION OF THE PREFERRED EMBODIMENT

Definitions

The term "Alkylating agent, or "$O^6$-alkylating agent" means a drug which acts by adding an alkyl group to DNA which inhibits cellular DNA synthesis. The term is intended to include nitrosoureas, which act similarly to alkylating agents and also inhibit changes necessary for DNA repair. These agents cross the blood-brain barrier and are therefore used to treat brain tumors, lymphomas, multiple myeloma, and malignant melanoma. Carmustine (BCNU) and lomustine (CCNU) are the major drugs in this category. Temozolomide (TMZ) is now the first-line chemotherapeutic for malignant gliomas. Other representative alkylating agents include Cyclophosphamide, Ifosfamide, Cisplatinum, Carboplatinum, Procarbazine, etc. The alkylation of DNA can be performed via two types of nucleophilic reaction, the SN1 and SN2 reaction. Substances that act via SN1 reaction, have a high selectivity for alkylation at the O6 or N2-position of guanine and substances that act via SN2 reaction, have a high selectivity for alkylation at the N7-position of guanine. Weak SN1 agents are more specific for alkylation at the N2 position and hard SN1 agents alkylate predominant the O6-position of guanine. Treatment of cells with these compounds gives rise to N-alkylated and O-alkylated purines and pyrimidines as well as phosphotriesters. One of the most critical O-alkylated lesions produced by an alkylating agent is $O^6$-methylguanine ($O^6$-MeG).

The term "brain tumor" is used as defined by the National Institutes of Health (See, world wide web address nlm.nih.gov/medlineplus/ency/article/007222.htm), and includes Glioblastoma multiforme—adults; Ependymoma—adults; Glioma—adults; Astrocytoma—adults; Medulloblastoma—adults; Neuroglioma—adults; Oligodendroglioma—adults; Meningioma—adults; Cancer—brain tumor (adults). In particular, the present methods and materials apply to high-grade gliomas and glioblastomas. The term "glioma" means a tumor that arises from the supportive tissue of the brain; for example, astrocytoma or oligodendroglioma. It may be benign or malignant. Cells from such tumors are also referred to herein as "diseased cells."

The term "resistant phenotype" means a cell that is at least 50% resistant (i.e., 50% of cells survive) to at least 2.5 μg/ml or mol, preferably at least 10 μg/ml or 10 μmol/L of an alkylating agent such as TMZ or BCNU, respectively. A cell that is not resistant is "sensitive." Ultimately, the resistant phenotype is distinguished from the sensitive phenotype by the absence of cell death after treatment with an O6-alkylating agent. Thus, a "therapeutically responsive phenotype" is not a resistant phenotype, and, in the case of a brain tumor, is a diseased cell that responds to known therapies of radiation and chemotherapy with an alkylating agent.

The term "gene expression" means the process by which a gene's coded information is converted into the structures present and operating in the cell. Expressed genes include those that are transcribed into mRNA and then translated into protein and those that are transcribed into RNA but not translated into protein (e.g., transfer and ribosomal RNAs).

The genes described below may be isolated and prepared as either the cDNA or genomic DNA encoding the mRNA, or the expressed protein, or both, as the context indicates. Various gene definitions are taken from NCBI Entrez Gene. The term "polyeptide" refers to either a full-length protein or an active fragment of a protein.

The term "TNFAIP3" is also known as A20, KIAAO113, NAF1, TNFA1P2, TNIP1, and tumor necrosis factor alpha-induced protein 3. It interacts with NAF1 and inhibits TNF-induced NF-kappa-B-dependent gene expression by interfering with an RIP- or TRAF2-mediated transactivation signal. It has a role in the function of the lymphoid system and may contribute to the in vivo effects of TNF (By similarity). It has deubiquitinating activity that is directed towards Lys-48 or Lys-63-linked polyubiquitin chains. It belongs to the peptidase C64 family. It contains 7 A20-type zinc fingers and 1 OTU domain.

TNFAIP3 includes the following GenBank sequences: AL157444, AY820830, BC041790, BC041790, BC064689, and BQ002744. The term is intended to include all variants (e.g., SNPs and splice variants).

The term "CD44" is also known as CD44R, CDW44, ECMR-III, IN, LHR, MC56, MDU2, MDU3, MGC10468, MIC4, MUTCH-I, Pgp1, CD44 antigen (homing function and Indian blood group system), CD44 antigen precursor (Phagocytic glycoprotein I) (PGP-1) (HUTCH-I) (Extracellular matrix receptor-III) (ECMR-III) (GP90 lymphocyte homing/adhesion receptor) (Hermes antigen) (Hyaluronate receptor) (Heparan sulfate proteoglycan) (Epican) (CDw44). It has 742 amino acids; 81554 Da. It interacts with HA, as well as other lycosaminoglycans, collagen, laminin, and fibronectin via its N-terminal segment. Interacts with ANK, the ERM proteins (VIL2, RDX and MSN), and NF2 via its C-terminal segment. It is a Type I membrane protein, which is proteolytically cleaved in the extracellular matrix by specific proteinases (possibly MMPs) in several cell lines and tumors.

CD44 has five alternative transcripts in REFSEQ: NP_000601.3, NP_001001389.1, NP_001001390.1, NP_001001391.1 and NP_001001392.1.

The term "FBXO32" means F-box protein 32, also known as ATROGIN1, FLJ32424, Fbx32, MAFbx, MGC33610, F-box only protein 32, muscle atrophy F-box, F-box only protein 32 (Muscle atrophy F-box protein) (MAFbx) (Atrogin-1). It is thought to recognize and bind to some phosphorylated proteins and promotes their ubiquitination and degradation during skeletal muscle atrophy. The protein contains 355 amino acids; 41637 Da. It is part of a SCF (SKP1-cullin-F-box) protein ligase complex. It is shown in REFSEQ proteins (2 alternative transcripts): NP_478136.1 NP_680482.1.

The term "SDC1," also known as CD138, SDC, SYND1, syndecan 1, Syndecan-1 precursor (SYND1) (CD138 antigen), refers to a gene whose protein has UniProt/Swiss-Prot accession number: SDC1_HUMAN, P18827, a size of 310 amino acids; 32477 Da; It is a Type I membrane protein and is known to exist in two alternative transcripts: NP_001006947.1 and NP_002988.3. The syndecan-1 protein functions as an integral membrane protein and participates in cell proliferation, cell migration and cell-matrix interactions via its receptor for extracellular matrix proteins.

The term "NFKBIA," also known as IKBA; MAD-3; NFKBI, refers to a gene whose protein is bound to REL (MIM 164910), RELA (MIM 164014), or RELB (MIM 604758) to form the NFKB complex. The NFKB complex is inhibited by I-kappa-B proteins (NFKBIA or NFKBIB, MIM 604495), which inactivate NF-kappa-B by trapping it in the cytoplasm.

The term "TNIP1," TNFAIP3 interacting protein 1, also known as VAN; NAF1; ABIN-1; KIAAO113, refers to a gene identified as having 2 alternatively spliced isoforms of NAF1, NAF1-alpha and NAF1-beta, that differ only in their C-terminal amino acids. NAF1-alpha contains 636 amino acids, and NAF1-beta contains 640 amino acids. Both isoforms have 4 coiled-coil domains and a proline-rich C terminus. Northern blot analysis has detected a 2.8-kb transcript in all tissues tested, with strong expression in peripheral blood lymphocytes, spleen, and skeletal muscle, and weak expression in brain. NAF mRNA was also detected in various human hematopoietic cell lines. GenBank Accession number is AJ11895.

The term "nucleic acid" or "nucleic acid molecule" is intended to include DNA molecules (e.g., cDNA [complementary to mRNA] or genomic DNA) and RNA molecules (e.g., mRNA) and analogs of the DNA or RNA generated using nucleotide analogs. The nucleic acid molecule can be single-stranded or double-stranded, but preferably is single stranded DNA when used as a target for hybridization with an expressed gene as described here.

The term "mRNA" will correspond to the sense strand of the coding sequences referred to herein and is used in its customary sense, i.e., messenger RNA transcribed during gene expression. mRNA as referred to herein generally will be mature mRNA, i.e., with capping, splicing and polyadenylation as is known to occur in eukaryotic cells.

The term "probe" means a single-stranded DNA or RNA molecule used to detect the presence of a complementary sequence among a mixture of other singled-stranded DNA molecules.

The term "microarray" is used to mean a high-density array of short DNA molecules bound to a solid surface, which facilitates high throughput analysis of thousands of genes simultaneously. The microarray, or DNA chip, contains a variety of sequences to provide a very powerful tool capable of probing a biological sample to determine gene expression, marker pattern or nucleotide sequence of DNA/RNA. In a typical microarray, DNA microarrays are comprised of a library of genes, immobilized in a grid on a glass microscope slide. Each unique spot or feature on the grid contains a DNA sequence derived from a specific gene that will bind to the mRNA produced by the gene in question. The standard microarray experimental platform consists of comparing mRNA abundance in two different samples. One fluorescent target is prepared from control mRNA and the second from mRNA isolated from treated cells or tissue under investigation. Both targets are mixed and hybridized together on the same microarray slide and target gene sequences hybridize to their complementary sequences. The microarray is excited, using a laser, to enable the fluorescent intensity of each spot to be determined. The relative intensities of the two colored signals on individual spots are proportional to the amount of specific mRNA transcripts in each sample, enabling an estimation of the relative expression levels of the genes in sample and control populations. It is further defined in U.S. Pat. No. 6,973,388, further referenced below.

All terms defined above are used in their conventional sense except as the definition may be explicitly contradicted in certain aspects by the definitions given.

Overview

The present invention is based on findings pursued in a translational approach from the lab to the clinic. We started with a new combined in vitro/in vivo resistance model (more exactly, cell lines that were established from clinical glioblastoma samples, which were either already resistant or which we selected for drug resistance) and identified a set of genes significantly linked to this "in vitro/in vivo" resistance phenotype. Subsequently, we showed that this set of genes actually predicted the survival of glioblastoma patients at Stanford (stratification of patients into one favorable and one unfavorable outcome group). That is, patients with tumors of a therapeutically responsive phenotype had a greater survival. A major concern with genomics analysis is always that there is substantial contamination with bystander genes that emerge randomly during the analysis but do not have anything to do with the pathogenic process of interest. We then established focused gene-reduction models in which we could show that various small subsets of genes (for example, 10 genes, or 4 genes) were self-sufficient in predicting the patient outcome. Our initial set of genes was significantly enriched for endogenous modulator genes of canonical NFKB activation. More importantly, our validation approach in the Stanford patients showed that TNFAIP3 (one of these modulators) was a constituent of the refined 4-gene predictor. Functional studies showed that there was actually an immediate link between TNFAIP3 abundance and NFKB activation status. This was validated in 3 additional independent patient cohorts from different institutions, as described below. It was shown in each of these three cohorts that the candidate genes (especially the NFKB modulators) were significantly linked to patient outcome (not only glioblastomas=grade IV glioma, but also in "high-grade" gliomas=grade III and IV gliomas). The NFKBIA gene outperforms the MGMT gene, the currently most established response marker for glioblastomas, in terms of survival prediction in both glioblastoma and high-grade glioma. In addition, if we combine several modulators (e.g. NFKBIA, TNFAIP3, TNIP1, TNIP2), our capability of predicting patient outcome, or identifying a therapeutically responsive phenotype, is even greater.

The description below references the treatment of glioblastomas with alkylating agents ($O^6$-alkylating agents), and the resistance of certain tumors to such agents. However, alkylating agents may be used in the treatment of various other human cancers, including chronic leukemias, Hodgkin's disease, lymphomas, and certain carcinomas of the lung, breast, prostate and ovary. Also, alkylating agents, particularly cyclophosphamide, are used in the treatment of a number of rheumatic and renal disorders including systemic vasculitis and glomerulonephritis associated with systemic lupus erythematosus (SLE) and other disease. The present sensitivity assays therefore be applicable to measure cell sensitivity in any condition to be treated with an alkylating agent.

As described below, it has been found that a distinct genomic signature is shared by glioblastoma cells selected for resistance to $O^6$-alkylating agents under in vitro and in vivo conditions. Alterations in several NF-κB pathway members in glioblastoma cells may act synergistically in activating NF-κB during resistance formation to $O^6$-alkylating agents. The most significant link to resistance to these agents within the NF-κB pathway was revealed for TNFAIP3. The consistent downregulation of this gene in our resistance models suggests a potentially important role of this gene in the development of resistance to $O^6$-alkylating agents in glioblastoma cells. Protein levels of TNFAIP3 were directly related to the expression of the corresponding transcript, as well as to the levels of NF-κB DNA-binding activity of the cells.

The zinc finger protein TNFAIP3 (Ref. 2) is a potent inhibitor of NF-κB signaling (Ref.[3]). Its mechanism of action involves the cooperative activity of its two ubiquitin-editing domains (Ref. 24). The amino-terminal domain of TNFAIP3 (Ref. 37), removes lysine-63 (K63) -linked ubiquitin chains from RIP (Ref. 24). The carboxy-terminal domain, composed of seven $C_2/C_2$ zing fingers (Ref. 36), then functions as an ubiquitin ligase by polyubiquitinating RIP with K48-linked ubiquitin chains, thereby targeting RIP for proteasomal degradation (Ref. 24). In addition to consistent downregulation of TNFAIP3 in resistant glioblastoma cells, which frees RIP, we also found a significant upregulation ($q<0.05$) of RIP in these cells. This observation supports a cooperative or reciprocal molecular mechanism for these two genes in the resistant phenotype. RIP, which complexes with IκB, has been reported to have an essential role in DNA-damage-induced NF-κB activation, but not in UV-induced NF-κB activation (Ref. 27). RIP-mediated NF-κB activation by drug- and irradiation-induced DNA damage is not mediated by autocrine or tumor necrosis factor receptor 1 (TNFR1) signaling. In line with recent evidence indicating that TNFAIP3 is critical for the regulation of TNF-independent signals that lead to termination of NF-κB activity (Ref. 38), our data provide evidence for an upstream extension of a RIP-mediated signaling cascade that augments NF-κB-induced resistance in glioblastoma cells to DNA-alkylating agents. Although the initiation point of this resistance signal remains ambiguous, our data support a model that extends its cytoplasmic pathway to TNFAIP3. We therefore propose a dual mechanism that may synergistically foster the activation of NF-κB by these agents. On receiving the nuclear signal in response to DNA damage, upregulation of RIP has been hypothesized to initiate the cytoplasmic signaling that activates NF-κB (Ref. 27). RIP action and its complexing with IκB may be enabled and ameliorated by downregulation of TNFAIP3 in the resistant cells, which under normal cell conditions obscures RIP by targeting it to proteasomal degradation. Functional validation will be needed to confirm this candidate resistance pathway in glioblastomas.

Our resistance signature-based outcome predictor model, derived from the cell lines, enabled us to subcategorize an independent cohort of glioblastomas commonly treated with $O^6$-alkylating agents into two major groups with apparently different outcomes. Based on this link we reasoned that the observed difference in survival might have been the result of distinct response characteristics of these tumors to therapy rather than different biological tumor behavior. Including more genes may make our predictive model perform better in independent validation analyses, but a smaller number of genes would make the model more practical and also amenable to future target modulation approaches. We have therefore reduced our resistance signature to a minimal number of genes for use in constructing a predictive model. We have shown that measurement of the weighted expression of four resistance-related genes was sufficient in predicting patient outcome. This optimized predictor, which included the four genes SDC1, CD44, FBXO32, and TNFAIP3, was able to partition glioblastomas into two subgroups according to their survival. The identification of TNFAIP3 as part of this predictor corresponds to its significant association with both resistance formation and NF-κB activation in our in vitro and in vivo cell models. It is supported as well by strong evidence for a link between NF-κB and glioblastoma cell survival (Ref. 39) and glioblastoma cell resistance to cytotoxic therapy (Refs.12, 40).

We have found reduced expression for all four genes associated with poor patient outcome. In line with our results, loss of SDC1, a transmembrane type I heparan sulfate proteoglycan and member of the syndecan proteoglycan family, has been linked to unfavorable prognosis of various human malignancies, including squamous cell carcinoma of the head and neck (Ref. 41), laryngeal cancer (Ref. 42), poorly differentiated non-small cell lung carcinoma (Refs. 43, 44), hepatocellular carcinoma with high metastatic potential (Ref. 45), and gastric cancer (Ref 46). In addition, SDC1 has been reported as a predictor of chemotherapy efficacy in oral squamous cell carcinoma, with decreased expression in response to cytostatic treatment indicating a poor prognosis (Ref. 47). CD44 has various functions in cell-cell and cell-matrix interactions. Expression of this cell-surface glycoprotein has been linked to increased survival in node-negative, invasive breast cancer (Ref. 48), and to indicate favorable prognosis in epithelial ovarian cancer (Ref. 49). Lack of CD44 expression is also a highly significant factor of poor outcome in neuroblastoma (Ref. 50). CD44v6 has been shown to predict responses to treatment in advanced colorectal cancer (Ref. 51). FBXO32 (Ref. 52), which constitutes a potential substrate-recognition component of the cell cycle-regulating SKP1-cullin-F-box (SCF) ubiquitin protein ligase (E3) complex and functions in phosphorylation-dependent ubiquitination (Refs. 53,54), has not been associated with tumor prognosis and drug resistance so far. Beta4GalNAc-T4, which is involved protein glycosylation (Ref. 55), was the only high-ranking transcript for which increased expression was associated with unfavorable outcome. Although the role of Beta1, 4-N-acetylgalactosaminyltransferases IV in drug resistance remains enigmatic, altered protein glycosylation has been implicated in tumorigenesis (Ref. 56). A limitation of our study, however, was the relatively small sample size and the not completely uniform treatment of our patients. Assessment of our predictor in a larger, standardized patient population will be necessary to ultimately assign outcome significance to these genes in glioblastomas, and to refine parameters for risk-based stratification. However, the genes selected here for inclusion in multiple gene assays have a highly statistically significant correlation with cell resistance to alkylating agents.

These results suggest a role of a cellular pathway that leads to NF-κB activation during the emergence of acquired resistance to $O^6$-alkylating agents in glioblastoma cells. While our data indicate the alteration of various members of the NF-κB canonical pathway, the endogenous NF-κB inhibitor TNFAIP3 was linked most significantly to the resistance phenotype. TNFAIP3 gene as well as protein expression mirrored the level of NF-κB activation in these cells. Though it remains unclear how the DNA damage response is linked to the cytoplasm, downregulation of TNFAIP3 may promote the initiation of a RIP-dependent signaling cascade that mediates NF-κB-induced cell survival. This gene was significantly related to patient outcome in a cohort of glioblastomas, and was a member of an optimized four-gene outcome predictor that enabled the subcategorization of these tumors. These observations raise the hope for an amenable target to modulate NF-κB-mediated resistance in glioblastomas cells, with the ultimate goal of increasing the efficacy of chemotherapy in patients harboring these challenging malignancies.

Materials and Methods

Cell culture and selection for drug resistant cell populations. Primary tumors were given a random two-letter code designation, and the recurrent tumor from the same patient received the same code with the addition of "R" (ME/MER, LX/LXR, DI/DIR). Cell lines were derived from these tumors as described (Refs. 13,14) and grown in Waymouth MAB 87/3 medium (MAB) with 20% fetal calf serum (FCS). Cells were selected for resistance to BCNU or TMZ as described (Refs. 14,15), using the maximum clinically achievable and tolerated doses. Briefly, cells were washed with MAB without serum 3 times; they were then mock-treated using MAB alone, or treated with increasing concentrations of BCNU (2.5, 5.0. 7.5, 10 μg/ml) or TMZ (2.5, 5.0, 7.5, 10 μM) in MAB for 1 hour at 37° C. with 5% CO2. Cells were washed and fed with MAB containing 20% serum. The cells were treated for three (BCNU) or five (TMZ) consecutive days, after which the cells were allowed to grow. Corresponding sets of cells were mock-treated, as described above, in parallel. This step was repeated several times until the resulting cell population was resistant, as evidenced by the absence of cell death after treatment when compared to the mock-treated controls. The time required to select for a resistant cell population varied for the different cell lines. Cells from the recurrent tumors had a higher level of intrinsic resistance than cells from the primary tumor. Cells were re-treated with 10 μg/ml BCNU or 10 μM TMZ every 8-10 passages to maintain the resistant phenotype.

Tumor specimens and patients. Thirty-one fresh-frozen glioblastoma specimens were collected and subjected to standard WHO classification (Ref. 16). Patients underwent tumor debulking surgery (gross total resection: 84%; subtotal resection: 16%) and were generally treated with an adjuvant regimen that included irradiation (total of ~60 Gy) and TMZ (150-200 mg per square meter for 5 days during each 28-day cycle). All but four patients were treated chemotherapeutically, and one patient also did not receive radiotherapy. For four patients, data on adjuvant therapy were incomplete. Written informed consent was obtained from all patients, and the study was approved by the Institutional Review Board of Stanford University Medical Center.

RNA and DNA preparation. For RNA extraction from cell lines and tumor specimens, cell lysates and samples were homogenized using QIAshredder columns (Qiagen, Valencia, Calif.) and a rotor-stator homogenizer (Kinematica, Cincinnati, Ohio), respectively. Total RNA was isolated from cell and tumor homogenates using the RNeasy Mini and RNeasy Lipid Tissue Kits (Qiagen), respectively, and quantified via spectrophotometry. RNA integrity was confirmed using the Agilent 2100 Bioanalyzer (Agilent, Palo Alto, Calif.). Universal human reference total RNA was purchased from Stratagene (Strategene, La Jolla, Calif.). Genomic DNA from cell lines was isolated using the DNeasy Tissue Kit (Qiagen, Valencia, Calif.), DPNII (New England Biolabs, Beverly, Mass.) digested, and purified using the QIAquick PCR Purification Kit (Qiagen). Genomic DNA and genomic digest were quantified spectrophotometrically. Human male and female genomic reference DNA was purchased from Promega (Madison, Wis.).

Microarray-based gene expression profiling. An indirect, dendrimer-based labeling method (Ref. 17) was used for microarray hybridization that utilized the Genisphere 3DNA Array 900 labeling system (Genisphere, Hatfield, Pa.), following the procedural protocol provided by the manufacturer without any modifications. For cDNA synthesis, 3 μg of glioblastoma and universal human reference total RNA were separately reverse transcribed using the Cy5- and Cy3-specific Genisphere primers, respectively, and hybridized together overnight at 65° C. to a Stanford human cDNA microarray containing 41,421 cDNA elements, corresponding to 27,290 different UniGene cluster IDs. Microarrays were coated with DyeSaver2 (Genisphere) immediately after the last wash. The Stanford Microarray is further described at world wide web address microarray.org/sfgf/servlet/Array.

Array-based comparative genomic hybridization. Labeling of digested DNA and microarray hybridizations were performed essentially as described (Ref. 18), with slight modifications. Two µg of DNA were labeled using random primers (Bioprime Labeling Kit; Invitrogen, Carlsbad, Calif.). Tumor DNA and reference DNA were fluorescently labeled with Cy5 and Cy3 dye (Amersham Biosciences, Piscataway, N.J.), respectively. Tumor DNA was hybridized together with sex-matching reference DNA to the same Stanford human cDNA microarray as above.

Data normalization and filtering. Microarrays were scanned on a GenePix 4000B scanner (Axon Instruments, Union City, Calif.). Primary data collection was performed using GenePix Pro 5.1 software. Raw data were deposited into the Stanford Microarray Database. Data were background corrected, filtered using a flag and background filter (1.5-minimal signal over background ratio for expression arrays; 2.5-minimal signal over background ratio in the reference channel and regression correlation >0.6 in both channels for array-CGH), and normalized by the LOWESS normalization function using SNOMAD data analysis tools (world wide web hypertext transfer protocol pevsnerlab.kennedykrieger.org/snomad.htm) or the TIGR MIDAS function of the TM4 microarray software suite (world wide web (tigr.org/software/tm4/midas.html). The GoldenPath Human Genome Assembly (world wide web hypertext transfer protocol (genome.ucsc.edu, National Center for Biotechnology Information build 34) was used to map fluorescent ratios of the arrayed human cDNAs to chromosomal positions. Chromosomal copy number maps were generated by mean filtering of signal intensity ratios according to 5-mb windows moved across the chromosomes in 2.5-mb steps. Gene copy number values were deemed changed as compared to normal human reference DNA if they fell beyond the ±3-standard deviation range (+/−0.2135) of distribution of all signal intensity ratios of control self-to-self hybridizations. For gene-by-gene integration of gene copy number and gene expression, copy numbers were reported as symmetric 3-nearest genomic neighbors moving averages (Ref. 19). The TreeView software (Ref. 20) was used to display gene expression and gene copy number ratios.

Inferential and descriptive statistics. In the cell line model, 9,734 out of 37,860 clones with expression in 80% of samples and whose expression levels differed by at least threefold, in at least one sample, from their mean expression levels across all cell lines were included in downstream statistical analyses. One-class response significance analysis of microarrays (SAM) (Ref. 21), which corrects for multiple testing by assigning a false discovery rate-based measure of significance, called q value (Ref. 22), was utilized after parental transformation of gene expression ratios of resistant sublines to identify genes overexpressed and under expressed in all in vitro and in vivo BCNU- and TMZ-resistant sublines. Genes identified with a q<0.005 were deemed significant. Non-parametric t-test analysis was performed in R (Ref. 23), and was used to allocate additional statistical confidence to clones identified by SAM. Unsupervised hierarchical clustering was performed in Cluster (Ref. 20), and two-way average linkage clustering was applied, based on Pearson correlation as a distance metric. Principal component analysis based on Pearson correlation was executed in MATLAB (The MathWorks, Natick, Mass.).

Gene ontology and functional network analysis. Analyses of gene ontology, canonical pathways, and functional networks were executed using Ingenuity Pathways Analysis tools (Ingenuity Systems, Mountain View, Calif.), a web-delivered application that enables the discovery, visualization and exploration of molecular interaction networks in gene expression data. The gene list identified by SAM, containing GenBank accession numbers as clone identifiers as well as d-scores, was uploaded into the Ingenuity pathway analysis. Each clone identifier was mapped to its corresponding gene object in the Ingenuity pathways knowledge base, which represents a proprietary ontology of 300,000 classes of biological objects spanning genes, proteins, cells and cell components, anatomy, molecular and cellular processes, and small molecules. Semantically consistent pathway relationships are modeled based on a continual, formal extraction from the public domain literature and cover more than 10,300 human genes (www.ingenuity.com/products/pathways_knowledge.html). These so-called focus genes were then used as a starting point for generating biological networks. A score was computed for each network according to the fit of the original set of significant genes. This score reflects the negative logarithm of the p value that indicates the likelihood of the focus genes in a network being found together due to random chance. Using a 99% confidence level, scores of 2 or higher were considered significant. Significances for the enrichment of the genes in a network with particular biological functions or canonical pathways were determined via right-tailed Fisher's exact test with $\alpha=0.05$ and the whole database as a reference set. The same computation was used for gene ontology analyses of the initial gene lists.

Real-time reverse transcription (RT)-PCR. Quantitative real-time RT-PCR reactions were performed with the ABI Prism 7900HT Sequence Detection System using SYBR GREEN PCR Master Mix (Applied Biosystems, Foster City, Calif.). Primers targeting the transcripts of TNFAIP3, NFKBIA, C8orf4 and LIF genes and the GAPDH housekeeping gene were designed with the Primer3 program (world wide web hypertext transfer protocol (frodo.wi.mitedu/cgi-bin/primer3/primer3_www.cgi) and synthesized at the Stanford PAN Facility (for sequences see Table 1 below). Total RNA was reverse-transcribed using the SuperScript first-strand synthesis system and SuperScript II (both Invitrogen). Thermocycling for each PCR reaction was carried out in a final volume of 20 µl containing 1 ng of cDNA, forward and reverse primers at 3 µM final concentration, and 1× SYBR GREEN PCR Master Mix. After 10 min of initial denaturation at +95° C., the cycling conditions of 40 cycles consisted of denaturation at +95° C. for 15 s, annealing at +55° C. for 30 s, and elongation at +72° C. for 30 s. All reactions were performed in triplicate. Dissociation curve analysis was performed after every run to confirm the primer specificity. Gene quantities were determined using standard curves, constructed by five serial dilutions of RT product of universal human reference RNA (Stratagene), and gene expression levels were reported as ratios of quantities of the target gene and GAPDH as the reference gene. The following primer sequences were used:

TABLE 1

| Primer sequences | Right | Left | SEQ ID NO: |
|---|---|---|---|
| TNFAIP3 | AATCTTCCCCGGTCTCTGTT | TACCCTTGGTGACCCTGAAG | 1, 2 |
| NFKBIA | ACACCAGGTCAGGATTTTGC | GCTGATGTCAATGCTCAGGA | 3, 4 |
| C8orf4 | TGTGTCGAAGTGGTAGCCATG | AGCCACCAAGCCATCATCAT | 5, 6 |
| LIF | TTCCAGTGCAGAACCAACAG | GTGCAGCCCATAATGAAGGT | 7, 8 |

Immunoblotting. The light-enhanced chemiluminescence protocol was used for the detection of specific proteins from total cell lysates prepared using 1×RIPA buffer [150 mM NaCl, 10 mM Tris (pH 7.2), 0.1% (w/v) SDS, 1.0% (v/v) Igepal CA-630 (Sigma-Aldrich, St. Louis, Mo.), 0.5% (w/v) Sodium deoxycholate, 5 mM EDTA]. Blots were exposed to 2 µg/ml of an anti-TNFAIP3 monoclonal antibody (Abcam, Cambridge, Mass.), recognized by a HRP-conjugated goat anti-mouse secondary antibody (Santa Cruz Biotechnology, Santa Cruz, Calif.). The ECL-Plus detection system (Amersham Biosciences) was used according to the manufacturer's protocol. Blots were stripped using the Re-Blot Plus mild antibody stripping solution (Chemicon International, Temecula, Calif.), and re-probed with two independent loading controls including the anti-β-actin goat polyclonal (Santa Cruz Biotechnology) antibody and the anti-GAPDH mouse monoclonal (Abcam, Cambridge, Mass.) antibody. A separate gel was stained with the SimplyBlue gel stain (Invitrogen) to ensure equal protein loading. Bands were quantified on an AlphaImager 2200 (Alpha Innotech, San Leandro, Calif.), and TNFAIP3 expression normalized to loading controls.

NF-κB DNA-binding activity assay. Nuclear protein extracts were prepared using the NucBuster Protein Extraction Kit (Novagen, Madison, Wis.) according to the supplier. DNA binding activity of NF-κB was assayed colorimetrically, utilizing the NoShift Transcription Factor Assay Kit and NoShift NF-κB (p65) Reagents (both Novagen) following the manufacturer's instructions. To assess sequence-specific binding activity, 15 µg of sample nuclear extract or 25 µg of HeLa positive control nuclear extract were incubated with various combinations of biotinylated NF-κB wild-type dsDNA, specific NF-κB competitor dsDNA lacking biotin end-labels, and non-specific, non-biontinylated dsDNA with a mutant NF-κB consensus binding motif. Negative controls consisted of reactions performed in the absence of a binding sequence. HRP-conjugated goat anti-mouse IgG was used as secondary antibody. All assays were performed in triplicate. Binding activity was measured via colorimetric absorbance at 450 nm on a ThermoMax multiwell spectrophotometer (Molecular Devices, Sunnyvale, Calif.) using TBM as substrate.

Survival analysis. Overall survival was calculated from the date of tumor diagnosis until death or the last follow-up contact. Data were current as of Jan. 1, 2005. At last follow-up 28% of patients were alive and 72% were dead. Patient subgroups were defined by unsupervised clustering of patients based on gene expression data of the resistance-associated transcripts revealed by SAM in the resistance model and with expression in >75 percent of the tumor specimens. Actuarial survival curves between groups were estimated by the Kaplan-Meier product-limit method and survival distributions between groups were compared using the log-rank test. Univariate and multivariate Cox proportional-hazards analyses were performed with overall survival as the dependent variable.

Results

Resistance signature of glioblastoma cells to $O^6$-alkylating agents. One-class response SAM, following parental transformation, was used to identify gene expression patterns associated with resistance formation to $O^6$-alkylating agents. A d-score was assigned to each gene on the basis of change in gene expression relative to the standard deviation of repeated measurements. Permutations of the repeated measurements estimated the q-value, a false discovery rate-based measure of significance (Ref 4). The three sensitive parental sublines DI, LX, and ME (which were obtained from untreated patient glioblastoma cells as described above were analyzed against the pool of 15 sublines with in vitro resistance to BCNU (DI-B and ME-B), in vivo resistance to BCNU (DIR, LXR, MER), combined in vivo I in vitro resistance to BCNU (DIR-B and MER-B), in vitro resistance to TMZ (LX-T, ME-T) and combined in vivo resistance to BCNU/in vitro resistance to TMZ (DIR-T, LXR-T, MER-T). DIR, LXR, MER show an in vivo resistance phenotype as a result of BCNU treatment of the corresponding patient and as confirmed by a resistance assay. Cell lines were made resistant in vivo to BCNU or TMZ as described above, and were resistant in vivo due to treatment of the designated individual with an alkylating agent.

FIG. 1 shows the transcriptomic resistance signature of glioblastoma cells to $O^6$-alkylating agents. This analysis revealed a set of 329 transcripts consistently overexpressed (78 clones, 23.7%) or underexpressed (251 clones, 76.3%) in the resistant versus the parental sublines (q<0.005) (FIG. 1A). The well-established resistance marker MGMT (Ref. 3) was among the top-scoring overexpressed transcripts (q<0.003). High-scoring underexpressed transcripts included the NF-κB-pathway modulator tumor necrosis factor α-induced protein 3 (TNFAIP3), which encodes the zinc finger protein A20 (Ref. 5), the NF-κB-inhibiting IκB family member NF-κB inhibitor α (NFKBIA), the metastatic colon cancer-down-regulated chromosome 8 open reading frame 4 (C8orf4) (Ref. 6), and the astrocyte differentiation-associated leukemia inhibitory factor (LIF)[7] (all, q<0.003). FIG. 1A displays these clones ordered according to d-score significance. D scores are further explained in Ref. 4. Non-parametric t-testing in the context of multiple testing was performed to allocate additional confidence to this resistance signature. 141 clones passed a p-value threshold of <0.01. While this analysis substantiated high significances for TNFAIP3 (p <0.000001), C8orf4 (p<0.000001), NFKBIA (p=0.000005), and LIF (p=0.000005) in the resistance phenotype, MGMT only passed a p-value filter of <0.05.

Figure 1A:
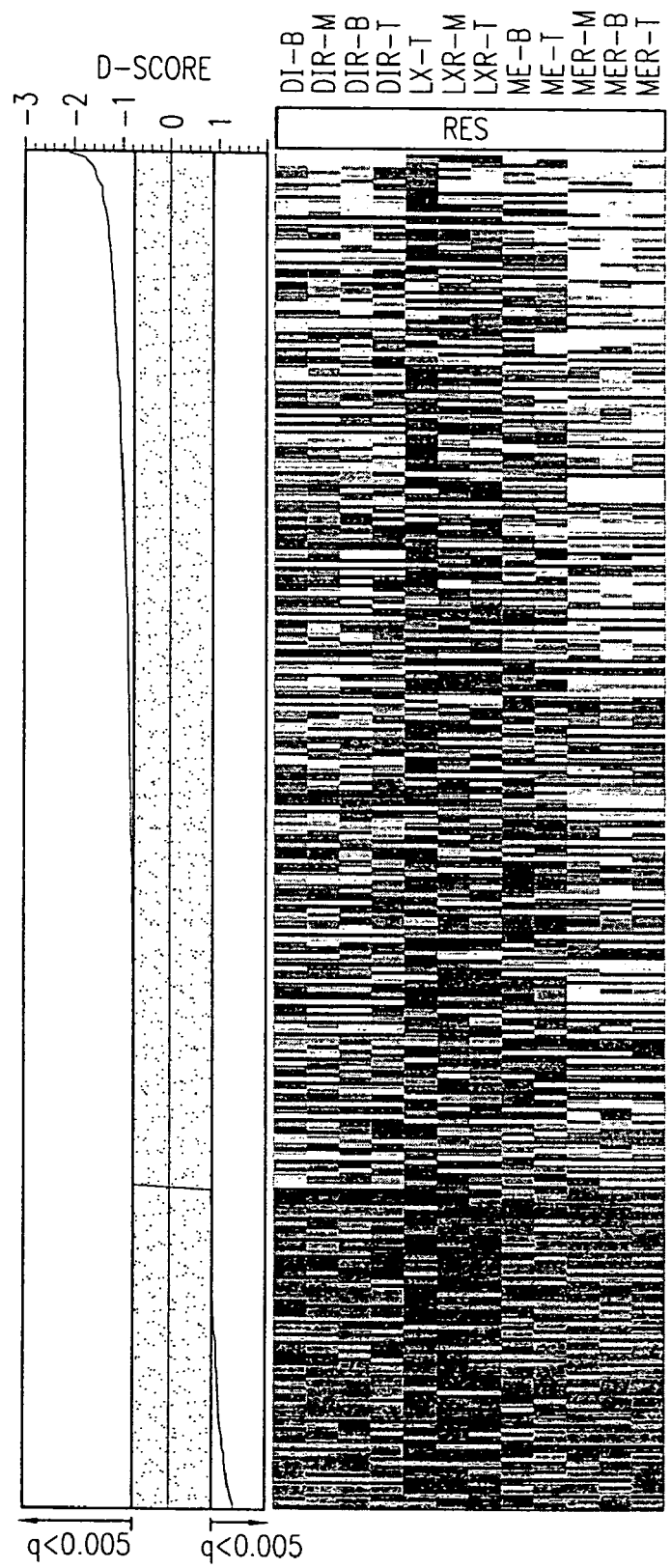
FIG. 1A, right side, represents a heat map displaying the expression of 329 transcripts identified by one-class response SAM (significance analysis of microarrays) to be significantly linked to the resistant phenotype (q<0.005). Expression levels in the resistant variants were normalized to their corresponding parental cell line to distinguish (one traditionally uses green, underexpression; red, overexpression—not shown here). Transcripts are ordered according to their d-score, shown on the left side.
Figure 1B:
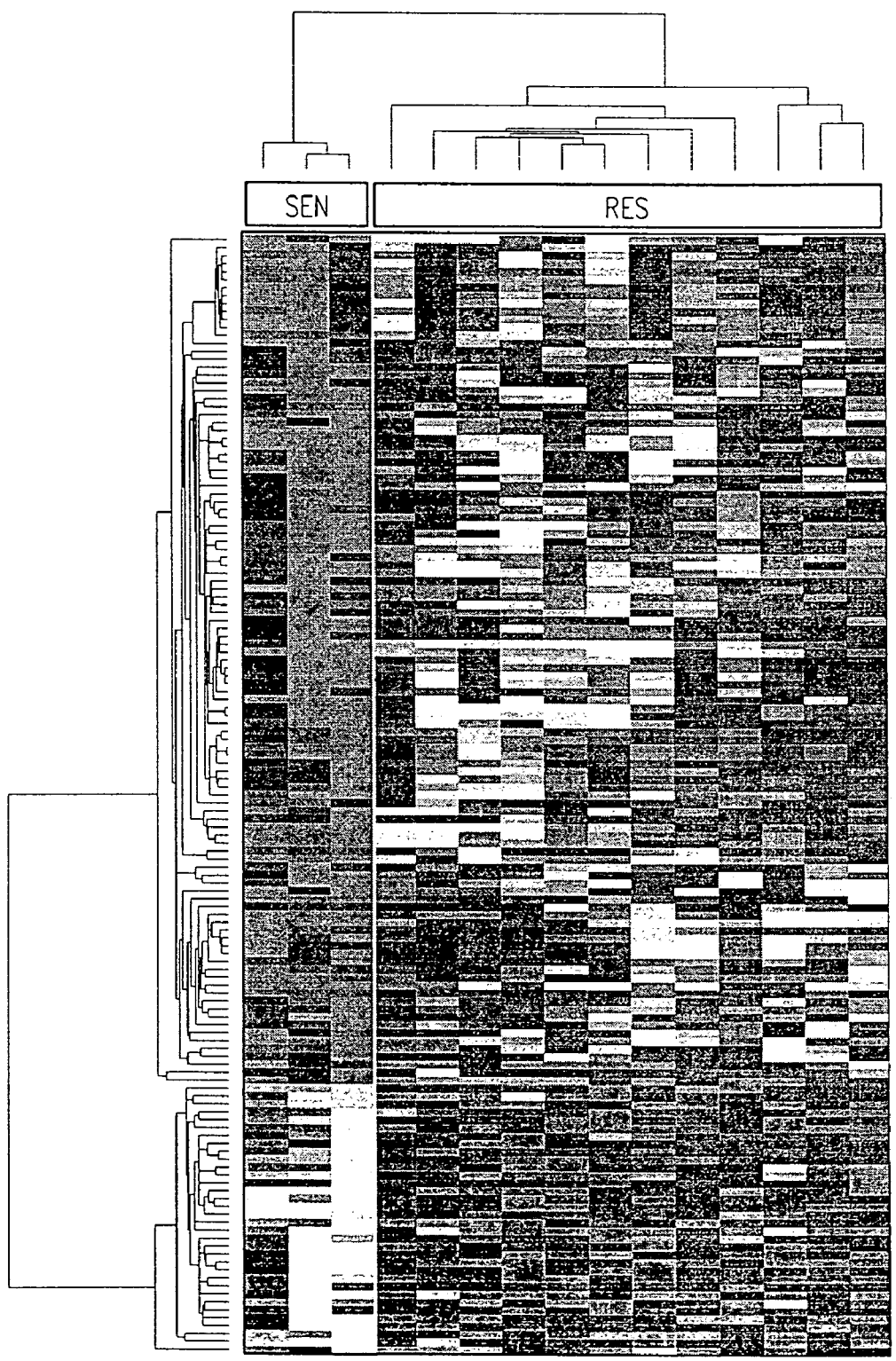
FIG. 1B is a heat map showing unsupervised, two-way average linkage clustering of 141 transcripts, identified by filtering the 329 SAM transcripts using a non-parametric t-test with a p-value threshold of 0.01, separated cell lines with a sensitive (Sen) phenotype from those with a resistant (Res) phenotype. 1C is a dendrogram with cell line labels corresponding to B. 1D is a graph showing principal component analysis in the same subset demonstrating the clear separation of Sen and Res phenotypes.
Figure 1C:
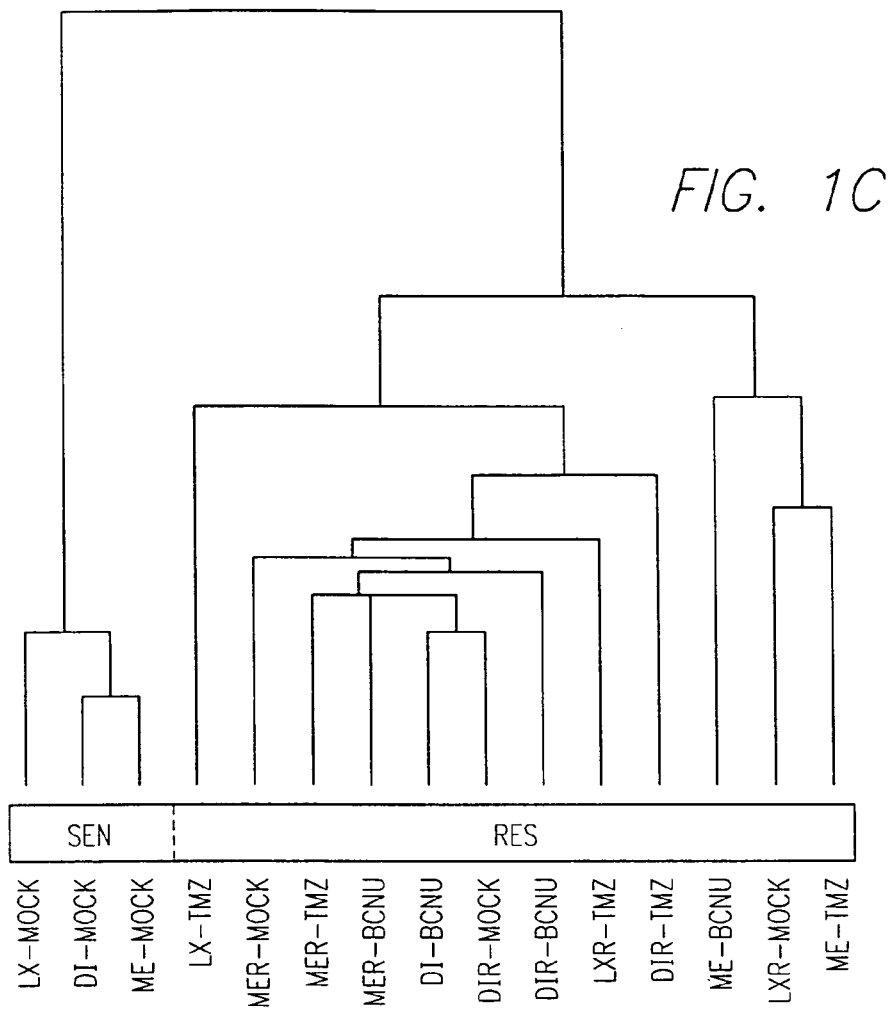
Figure 1D:
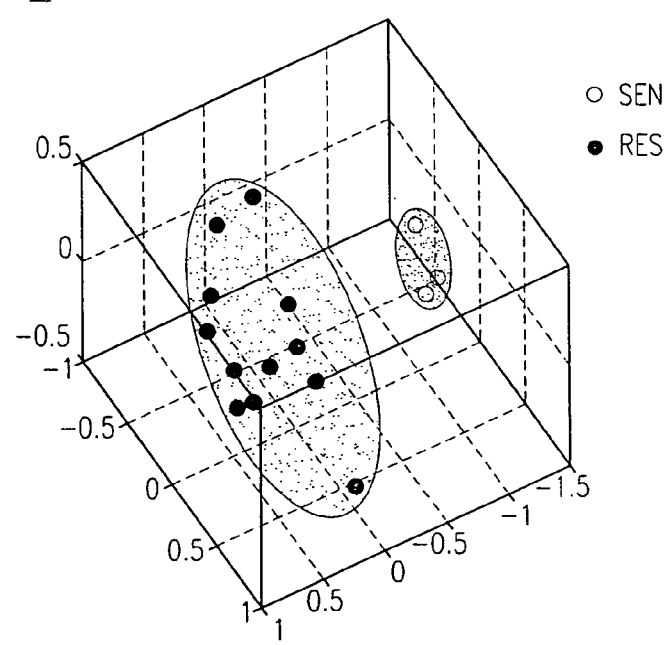

The strength and accuracy of this highest-confidence subset of 141 transcripts in predicting sensitive versus resistant phenotypes was evaluated by two-dimensional unsupervised average linkage cluster analysis after cell line-specific, mean centering of the expression data. Gene expression levels of these transcripts separated hierarchical clustering samples into two groups based on sensitivity phenotype (FIGS. 1B-C). An unsupervised learning algorithm based on multidimensional scaling using the first three principal components confirmed the phenotype-specific separation of the sublines by the subset (FIG. 1D).

Figure 2A:
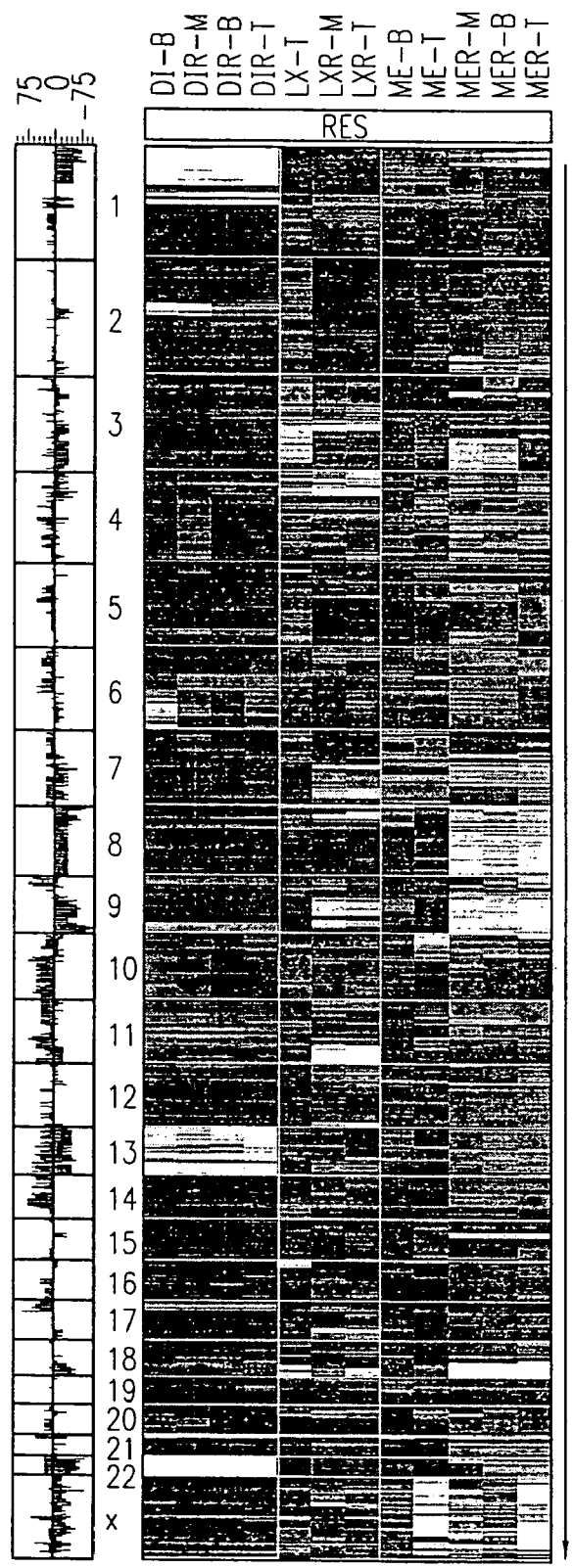
FIG. 2A, right, is a heat map of a highly compressed genome-wide gene copy number map, in which 33,587 cDNA clones are ordered position along the chromosomes and are mean filtered according to 5-mb windows moved across the chromosomes in 2.5-mb steps. Gene copy numbers in the resistant variants are normalized to their corresponding parental cell lines and masked to only indicate changes beyond the ±3-standard deviation range of distribution of signal intensity ratios of control self-to-self hybridizations. Discrete copy number transition points are readily distinguishable from chance noise events. Copy number gains and losses in original figure were color-coded in red and green, respectively. Left, corresponding recurrence frequencies of chromosomal alterations in the resistant variants and aligned in genome order. 2B is a heat map showing integration of gene copy number and gene expression data of the resistance signature. Copy numbers in resistant cells normalized to their corresponding parental cells are reported as symmetric 3-nearest genomic neighbors moving averages. 92 genes demonstrated coincident alterations in gene dosage and gene expression. The heat map is masked to only show fluorescent ratios indicating genes with >±2-fold change in gene dosage in the resistant vs. the sensitive sublines.

Genome-wide gene copy number maps. Since gene copy number aberrations have a significant impact on gene expression patterns and also represent common mechanisms of gene activation and inactivation in drug resistance formation, we have mapped gene copy numbers in a high-resolution manner using the same cDNA microarray platform. FIG. 2 shows genomic changes associated with resistance formation of glioblastoma cells to $O^6$-alkylating agents. FIG. 2A reports the copy number profile for 33,587 clones mapped along the genome and mean filtered according to 5-mb windows moved across the chromosomes in 2.5-mb steps. Multiple resistance-associated gene copy number changes, including both losses and gains, were found, with the extent of the chromosome involved in the alterations differing for each chromosome. While some areas of the profile were similar across most of the samples (i.e., chromosome 9q33.2-q33.3), others showed differences based on the individual patient's tumor (i.e., chromosome 13), or on whether the cells were from the primary or recurrent tumor (i.e., chromosome 7q11.21-q31.31). The left panel of FIG. 2A shows the recurrences frequencies of these changes in the resistant variants. Peak recurrences of chromosomal gains were noted for chromosomes 9p23-9p22.3, 10q21.1, 11q14.1, 14q23.2-q31.1, and 17p11.2, as were those of losses for chromosomes 1p35.2-p34.3, 8p23.2-p23.1, 9q33.2-q33.3, 22q11.1-q21.1, and Xp21.2-p21.1.

Figure 2B:
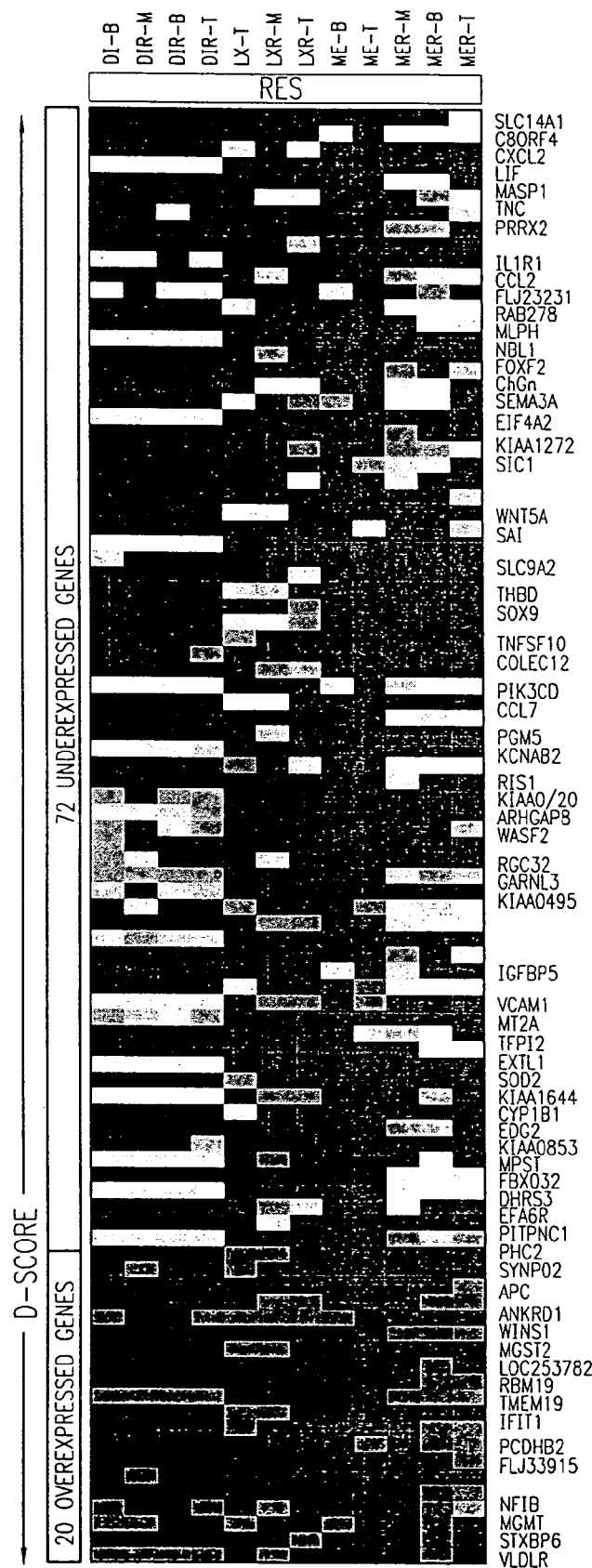
Figure 4A:
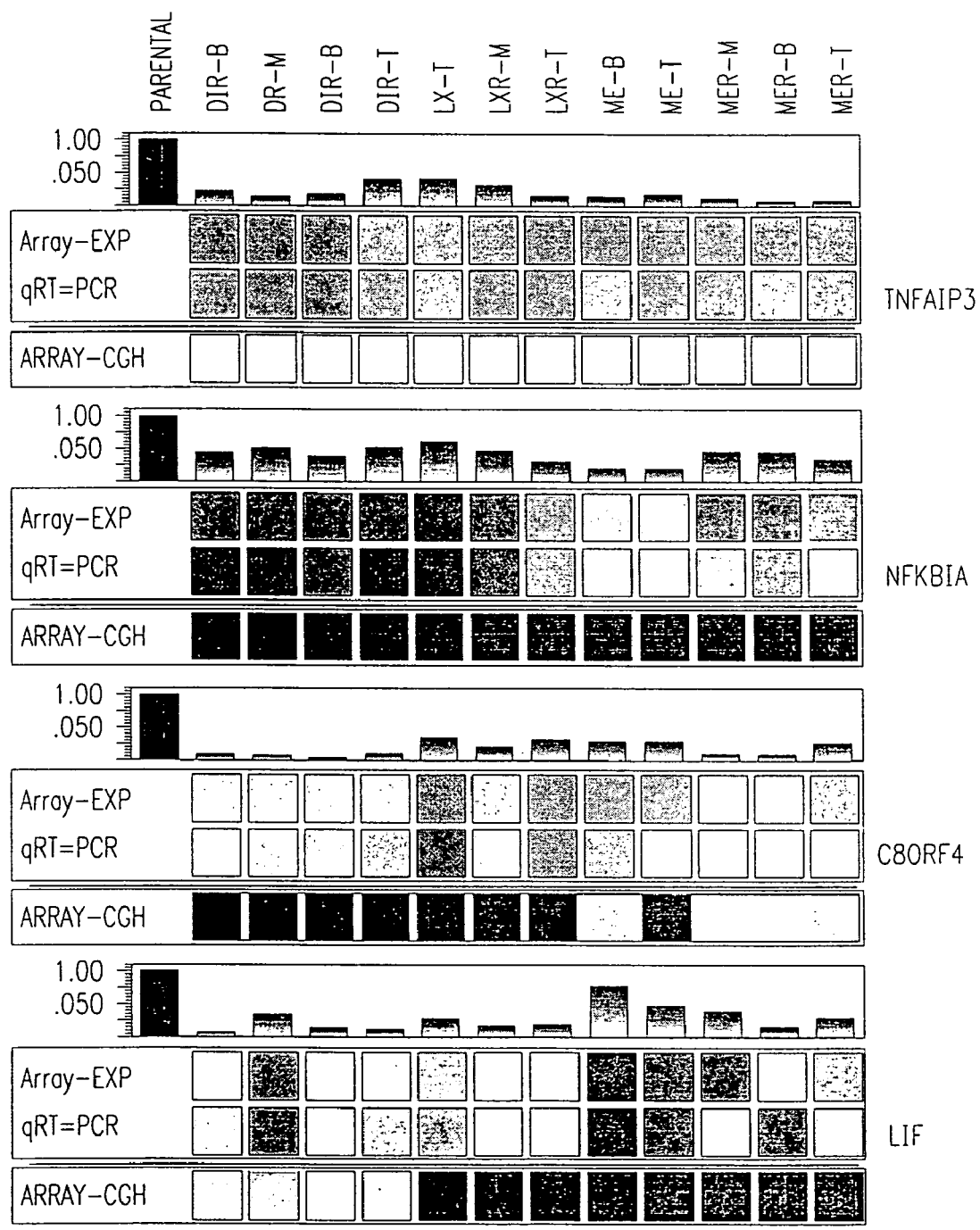
FIG. 4 is a series of bar graphs of candidate resistance genes. The bar graphs indicate the microarray-assessed gene expression in resistant cells relative to the corresponding parental cells. 4A shows gene expression by microarray and real-time RT-PCR of four genes (TNFAIP3, NFKBIA, C8orf4, and LIF) identified as constituents of a resistance signature in glioblastoma cells. In 4B, bars reflect the mean expression levels of the four target genes in the resistant variants normalized to their corresponding parental cells, error whiskers indicate the spread of the expression across all resistant variants. A high degree of concordance between microarray and real-time RT-PCR analyses is apparent. 4C, Microarray-based, parentally normalized gene expression and gene copy numbers for TNFAIP3-interacting RIP and the established resistance factor MGMT.
Figure 4B:
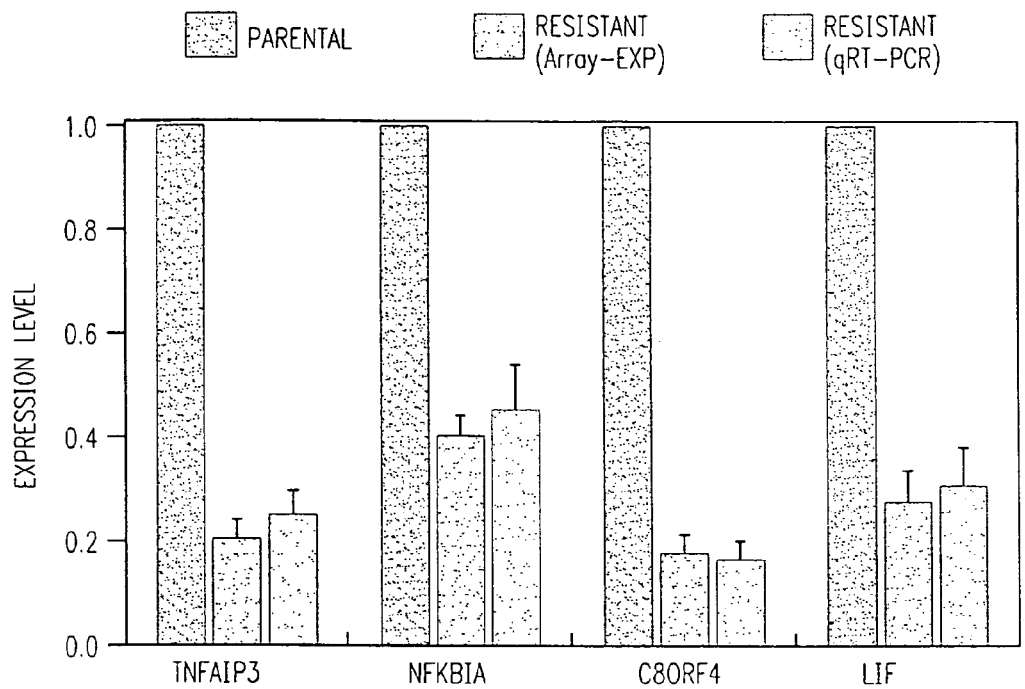
Figure 4C:
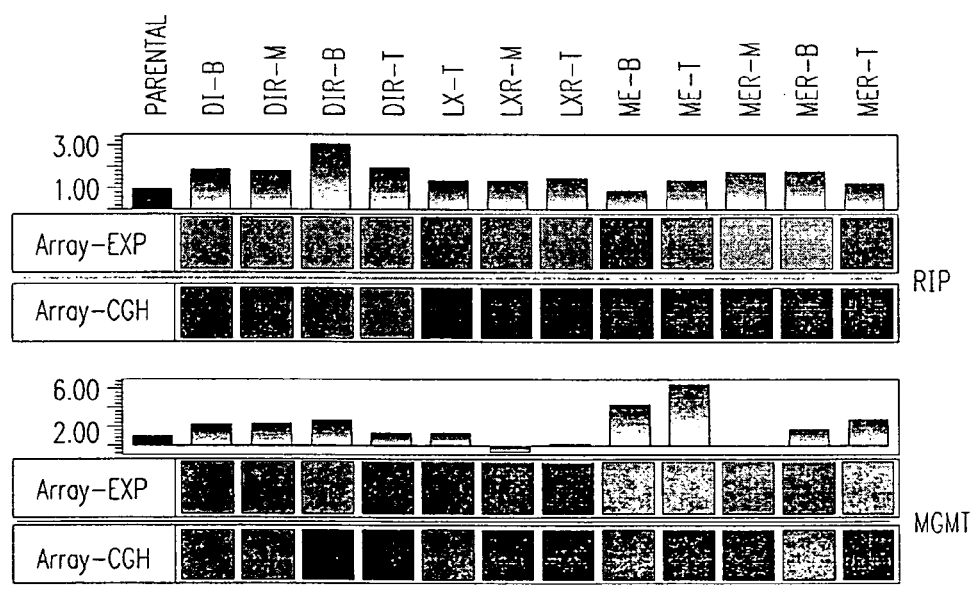

Integration of gene copy number and gene expression data. We then examined the effect of gene copy numbers on the expression of the 329 transcripts identified as resistance signature by SAM. For a gene-by-gene integration of copy numbers and expression, copy numbers were reported as symmetric 3-nearest genomic neighbors moving average (Ref. 19). The dataset was then filtered to include only those fluorescent ratios indicating genes that demonstrated at least ±2-fold changes in gene dosage in the resistant variants versus the corresponding sensitive parental sublines (Ref. 19). This analysis revealed a pervasive imprinting of aneuploidy on gene expression in a distinct subset of resistant sublines for 92 genes, 72 and 20 of which demonstrated losses and gains in copy number, respectively (FIG. 2B). Many of these genes with copy number-driven expression mapped to the recurrent resistance-associated chromosomal aberrations revealed in FIG. 2A. C8orf4 and LIF were among the genes with reduced copy number in a subset of resistant sublines (FIGS. 2B and 4A), and MGMT was among those with increased copy number (FIGS. 2B and 4C). No difference in gene copy numbers of TNFAIP3 and NFKBIA were noted between the resistant and the sensitive sublines (FIG. 4A).

Figure 3:
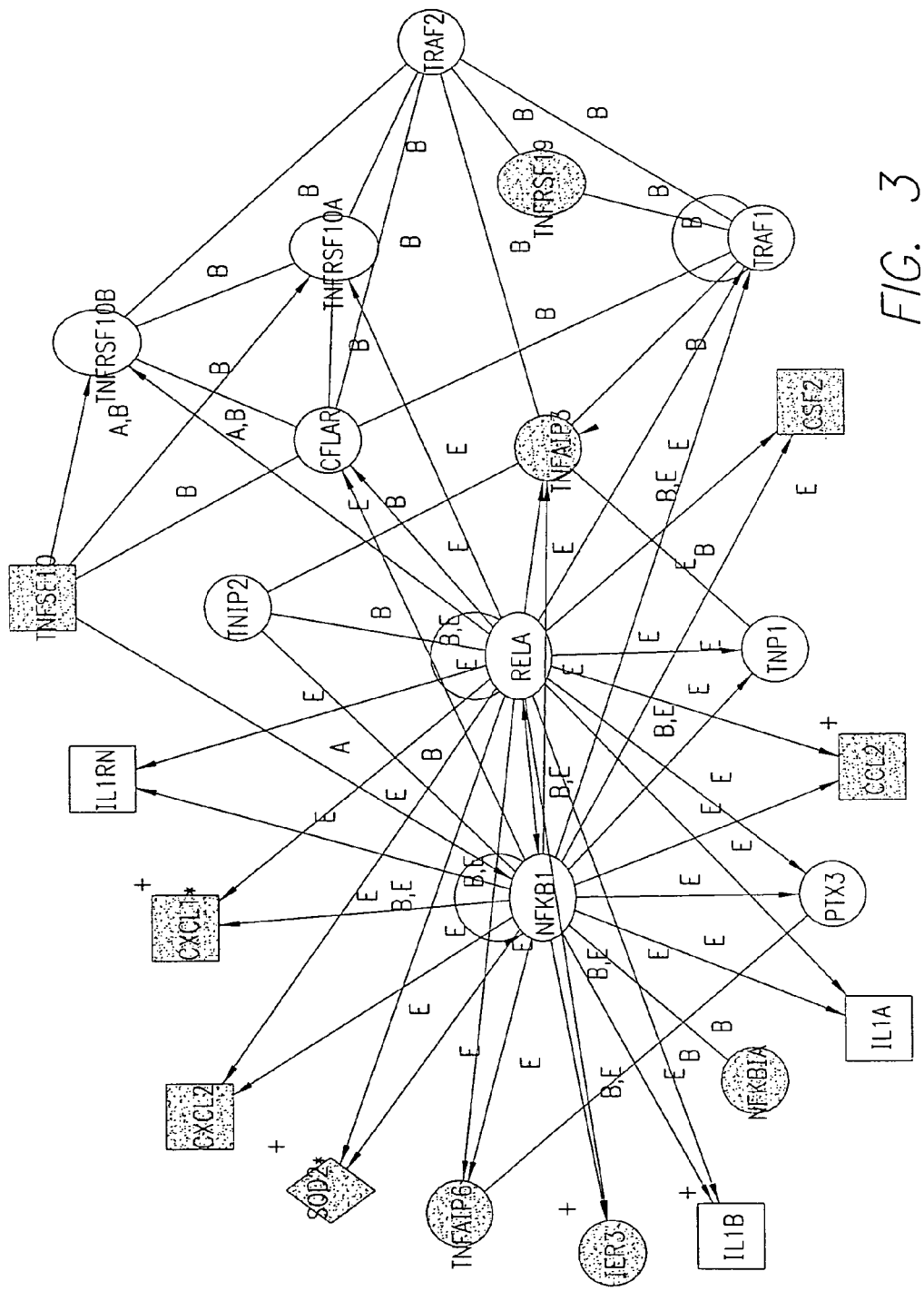
FIG. 3 is a graph showing a functional network analysis of resistance signature illustrating an excerpt of the top-scoring functional network built around NF-κB, which included several altered NF-κB-interacting genes and NF-κB pathway modulators, and members such as TNFAIP3 and NFKBIA. Molecular interactions and subcellular distribution of resistance genes were analyzed in an extensive network map, composed of seven overlapping functional networks (see Table 2). Nodes represent genes, with their shapes representing the functional classes of the gene products, and edges indicate the biological relationship between the nodes). Nodes are shaded according to their d-score (dark) overexpression; (light) underexpression). Shapes are diamond, enzyme; transcription factor, oval; phosphatase, upward triangle; translation factor, small circle; square, growth factor; shaded square, cytokine; connecting lines refer to binding; arrows refer to acting on; A means activation/deactivation; B means binding; E means expression.

Gene ontology, biological pathway, and network analysis. To explore how the 329 transcripts identified by inferential statistics as part of a resistance-associated gene expression signature are related, the genes were placed in the context of present knowledge about pathways, using Ingenuity pathways analysis tools. Initial gene ontology analysis revealed significant enrichment of the signature for genes involved in organismal survival (27.5%, $p<0.000003$) and cell death (49.0%, $p<0.000005$). Biological pathway analysis revealed the NF-κB canonical pathway as a significant molecular pathway in the dataset ($p=0.046$). Network analysis based on predetermined knowledge about individually modeled relationships between genes identified seven highly significant, overlapping networks in the dataset (FIG. 3A). The top-scoring network, built around NF-κB, displayed high-level functions in cell death, cellular compromise (stress), and organismal survival, and included several altered NF-κB-interacting genes and NF-κB pathway constituents and modulators such as TNFAIP3 and NFKBIA (FIG. 3B). Table 2 below shows the seven networks in the dataset.

TABLE 2

Functional network analysis based on 329-transcript resistance signature.

| No. | Genes in Network[1] | NW Genes[2] | Focus Genes[3] | Score[4] | High-Level Functions | Associated Genes[5] | Significance[6] |
|---|---|---|---|---|---|---|---|
| 1 | BCL3, CCL2, CD44, CFLAR, CSF2, CXCL1, CXCL2, DACH1, FN1, FOS, HGF, IER3, IL1A, IL1B, IL1RN, KRT8, NFKB1, NFKBIA, PLAU, PTX3, RELA, SDC1, SERPINE2, SOD2, TNFAIP3, TNFAIP6, TNFRSF19, TNFRSF10A, TNFRSF10B, TNFSF10, TNIP1, TNIP2, TRAF1, TRAF2, VLDLR, WASF2 | 36 | 15 | 18 | Cancer | 25 | 3.33 × 10−12-0.003 |
|  |  |  |  |  | Cell death | 26 | 3.33 × 10−12-0.003 |
|  |  |  |  |  | Cellular compromise | 10 | 6.03 × 10−7-0.003 |
|  |  |  |  |  | Organismal survival | 15 | 9.30 × 10−7-2.27 × 10−4 |
| 2 | APC, BCL3, BTRC, BUB1, CDC34, CITED1, CSNK1D, CSNK1E, CSNK2A1, CSNK2B, CUL1, E2F3, ENG, FBXO32, FOXF2, FST, INHBA, | 35 | 14 | 17 | Cell Cycle | 15 | 6.29 × 10−7-0.027 |
|  |  |  |  |  | Cellular Compromise | 7 | 4.51 × 10−6-0.010 |

TABLE 2-continued

Functional network analysis based on 329-transcript resistance signature.

| No. | Genes in Network[1] | NW Genes[2] | Focus Genes[3] | Score[4] | High-Level Functions | Associated Genes[5] | Significance[6] |
|---|---|---|---|---|---|---|---|
|   | INHBB, MGST2, MMP13, NFKBIA, NKD2, PTPN13, RBX1, SKP1A, SLPI, TBP, TBX3, TFAP2C, TFDP1, TFPI2, TGFA, THBD, TP53, UBE2D2 |   |   |   | DNA Replication, Recombination, and Repair | 13 | $4.51 \times 10-6-0.016$ |
| 3 | ABCC2, APOA1, CCND1, CCNH, CDKN1C, CEBPB, CXCL1, CYP1B1, | 35 | 14 | 17 | Cellular Growth and Proliferation | 24 | $1.07 \times 10-8-0.021$ |
|   | DYRK1B, EGR1, ENPEP, ESR1, FOSL1, FOXO1A, IL1B, IL1R1, IL1RAP, LBP, NR1H4, NR1I3, NR2C2, NR2F1, PIK3CA, PIK3CB, PIK3CD, PIK3CG, PIK3R1, PIK3R2, PIK3R3, POU2F1, SAT, SNCG, SOD2, XPO1 |   |   |   | Cancer | 23 | $1.50 \times 10-8-0.019$ |
| 4 | ANKRD1, BIN1, CDC2, CDKN1C, CDX2, CEBPA, CTBP1, E2F2, EVI1, FHL2, FLJ12541, GATA4, HDAC1, IGFBP5, MGMT, MSX1, MSX2, MYB, MYOD1, NBL1, NKX2-5, NPAS2, NPTX1, NSEP1, PML, PRDC, RARA, RARB, RARG, RGC32, TBX5, THBS1, TP73, ZBTB16, ZFML | 35 | 14 | 17 | Cell death | 26 | $2.80 \times 10-10-0.050$ |
|   |   |   |   |   | Gene expression | 22 | $6.18 \times 10-10-0.036$ |
|   |   |   |   |   | Cellular development | 19 | $1.40 \times 10-8-0.046$ |
| 5 | AGC1, CCL2, CCL7, CCL8, CCR2, CCR3, CCRL1, CD53, COL8A1, FMR1, ITGA4, ITGA9, ITGB1, KCNA3, KCNAB1, KCNAB2, KCNX3, KIAA1893, MLPH, MMP3, MMP13, MTPN, MYO5A, MYRIP, PRKCA, RAB27A, RAB27B, S100A10, SERPINE1, SHARP, SPARC, SPP1, TNC, VCAM1, VTN | 35 | 14 | 17 | Cancer | 18 | $5.01 \times 10-12-0.021$ |
|   |   |   |   |   | Cellular movement | 20 | $5.01 \times 10-12-0.021$ |
|   |   |   |   |   | cell morphology | 18 | $7.59 \times 10-10-0.021$ |
| 6 | ABCG5, ABCG8, BRCA1, CANX, CCNB1, CCND1, CCND2, CCNE1, CDK4, CDKN1B, EDN1, EDNRA, EIF4A1, EIF4A2, EIF4E, EIF4G1, EIF4G2, EIF4E, EIF4G1, EIF4G2, EIF4G3, HTATIP, IER3, IFIT1, LDB2, LMO4, MAPK3, MYC, PCNA, PHC2, RBL1, RBL2, RNF110, | 35 | 10 | 10 | Cell cycle | 18 | $2.13 \times 10-10-0.010$ |
|   |   |   |   |   | Cancer | 21 | $2.24 \times 10-9-0.010$ |
|   |   |   |   |   | Cellular development | 17 | $1.09 \times 10-8-0.010$ |

TABLE 2-continued

Functional network analysis based on 329-transcript resistance signature.

| No. | Genes in Network[1] | NW Genes[2] | Focus Genes[3] | Score[4] | High-Level Functions | Associated Genes[5] | Significance[6] |
|---|---|---|---|---|---|---|---|
| 7 | SCAMP5, TPD52, TPD52L1, TPD52L2, VEGF ETV1, HSPB6, KCNMA1, KCNMA3, KCNMB1, KCNMB2, KCNMB4, LCP1, PRKACA, SOX9 | 10 | 5 | 7 | Cell-to-cell signaling and interaction | 7 | 2.01 × 10-6-0.038 |
|  |  |  |  |  | Nervous system development | 3 | 2.01 × 10-6-0.010 |

NOTES:
[1]Genes in Network: bold black: genes of the test set that were overexpressed in the resistant cells, underlined: genes of the test set that were under expressed in the resistant cells, regular: global analysis genes that were not altered in expression in the test set
[2]NW (Network) Genes: total number of genes in the network
[3]Focus Genes: number of genes identified as part of the test set mapping to the network
[4]Score: reflects the negative logarithm of the p value that indicates the likelihood of the focus genes in a network being found together due to random chance (using a 99% confidence level, scores of >= 2 were considered significant)
[5]Associated Genes: number of genes significantly associated with the corresponding high-level function
[6]Significance: range of significances of the associated genes for the high-level function (a = 0.05)

Exploration of the NF-κB candidate pathway. Since our inferential statistical analysis and data from the literature (Ref. 12) evidenced importance of the NF-κB pathway in mediating resistance to $O^6$-alkylating agents in glioblastoma cells, we searched the whole expression dataset for alteration of additional members of this putative resistance pathway, applying a more liberal q-value threshold of <0.05 for the allocation of statistical significance. Using this threshold, the TNFAIP3 target gene RPA interacting protein (RIP) (Ref. 24) (FIG. 4C), which has been implicated in NF-κB-mediated cell responses to DNA damage (Ref. 27), was revealed to be significantly linked to the resistance phenotype (q=0.044). The recurrent overexpression of this gene was revealed to be partly related to gene copy number gains in the resistant glioblastoma genome (FIG. 4C). In addition, decreased expression of the IκB family member NF-κB inhibitor ε (NFKBIE), which inhibits NF-κB, was significantly associated with resistance formation at the same threshold level (q=0.027). Although not passing a q-value threshold of <0.05, expression alterations of additional NF-κB pathway constituents were sporadically observed in our model. These included the underexpression of the gene encoding the TNFAIP3-interacting protein 1 (TNIP1; q=0.0975) in 50% of the resistant variants, a protein which is suggested to inhibit NF-κB independent of its mutual interaction with TNFAIP3 (Ref. 28).

Candidate genes. Gene expression levels for the NF-κB pathway genes TNFAIP3 and NFKBIA were confirmed by real-time RT-PCR. The relative expression of the two transcripts C8orf4 and LIF, deemed biologically interesting because of their highly significant association with the resistance phenotype, was also confirmed by real-time RT-PCR. C8orf4, which is downregulated in metastatic colon cancer, has been implicated in colon cell differentiation and TGFβ-induced apoptosis (Ref. 6). The neuropoietic cytokine family member LIF regulates gliogenesis (Ref. 29) and promotes differentiation of astrocytes (Refs. 26,30). This gene is normally expressed in glioma cells (Ref. 31) and mediates a growth inhibitory effect in these cells (Ref. 32). FIG. 4A correlates the expression levels of these four genes revealed by the microarray and the real-time RT-PCR analyses and also indicates the gene copy number profiles for these genes. There was high concordance between both analyses in individual sublines (FIG. 4A), as well as when the mean transcription levels of all resistant sublines normalized to their corresponding parental cells and their spread were compared (FIG. 4B). FIG. 4C interfaces gene expression and copy numbers for the RIP and MGMT genes, indicating the relationship of RIP gene dosage to gene expression in the DI/DIR cell lines, but not LX/LXR and ME/MER. MGMT gene dosage correlates with expression in some, but not all of the cell lines examined.

Figure 5A:
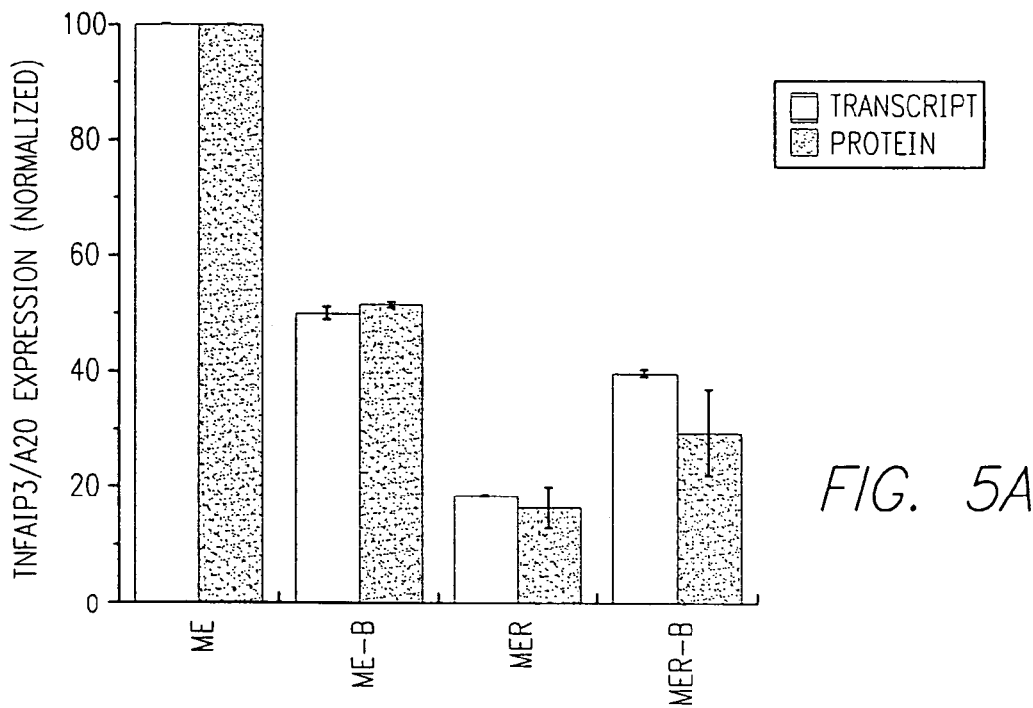
FIG. 5A is a bar graph showing TNFAIP3 gene and protein expression in ME cell lines. Expression levels in the resistant variants are indicated as percentages of expression in the parental cells. Gene expression, assessed by real-time RT-PCR, is normalized against the GAPDH housekeeping gene. Protein expression, assessed by immunoblotting, is normalized to loading controls (GAPDH, β-actin) from two independent blots with the range of expression indicated. 5B is a representative blot with TNFAIP3 (~70 KDa), β-actin (~43 KDa) and GAPDH (~36 KDa) expression. 5C is a bar graph showing competitive analysis of NF-κB DNA-binding activity in the same cell lines and HeLa positive control nuclear extract. Left bars, binding activity assessed by biotinylated NF-κB wild-type (WT) dsDNA; middle bars, WT dsDNA plus non-specific, non-biotinylated dsDNA with a mutant NF-κB consensus binding motif (NSC); right bars, WT dsDNA plus specific NF-κB competitor dsDNA lacking biotin end-labels (SC); Neg, negative control.
Figure 5B:
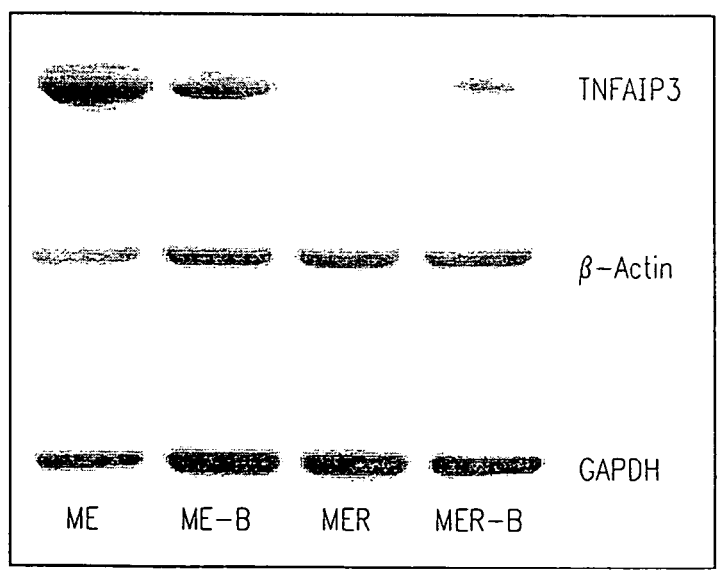

Correlation of TNFAIP3 protein and gene expression. Since our integrated large-scale screening and inferential statistical approach for resistance factors had highlighted a potentially important role of the NF-κB pathway modulator TNFAIP3 in the resistance of glioblastoma cells to $O^6$-alkylating agents, we examined whether the reduced expression of the TNFAIP3 transcript in the resistant cells may be reflected by reduced expression of the cognate protein product A20. FIG. 5 shows TNFAIP3 expression and NF-κB activation in resistant cells. FIG. 5B shows a representative immunoblot in ME cell lines. FIG. 5A indicates the A20 protein expression in these cell lines normalized to loading controls. A substantial reduction in protein expression in all resistant variants compared to the sensitive parental subline was noted. FIG. 5A also correlates TNFAIP3 protein and gene expression in these cells. In each cell line, the levels of protein product closely mirrored the expression of the corresponding transcript as determined using real-time RT-PCR.

Figure 5C:
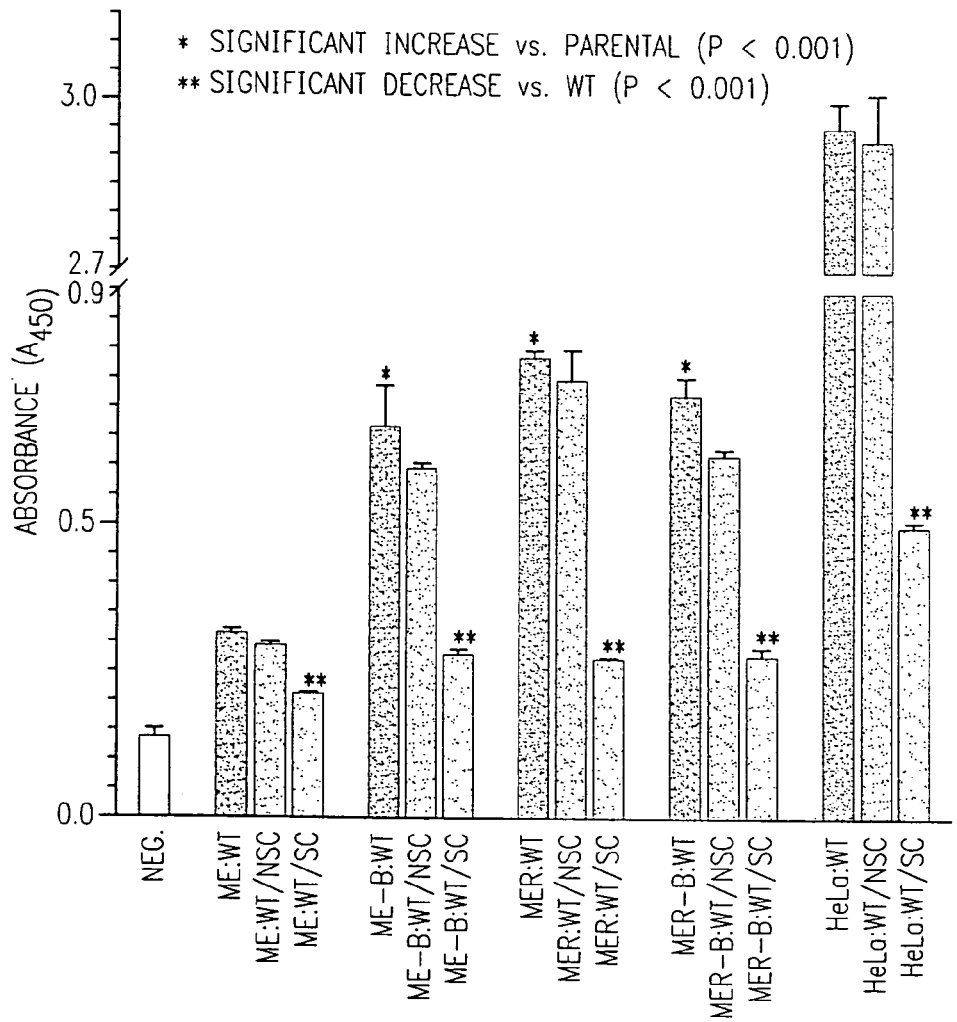

DNA-binding activity of NF-κB in sensitive vs. resistant cells. Because the presumed functional consequence of downregulation of TNFAIP3 transcript and protein is increased NF-κB pathway activation with resulting nuclear translocation and DNA binding of NF-κB, we then assessed the NF-κB DNA-complexing activity in sensitive versus resistant cells. NF-κB activation was assayed by the binding of NF-κB to oligonucleotides containing the consensus-binding site. FIG. 5C shows a competitive analysis of NF-κB DNA-binding activity in parental ME cells and resistant ME-B, MER, and MER-B cells. Nuclear extract from HeLa cells stimulated with TNF-α was used as a positive control (Ref. 33). To assess sequence-specific binding activity, nuclear extracts were incubated with NF-κB wild-type DNA, with or without either specific NF-κB competitor DNA or non-specific mutant NF-κB consensus-binding motif. When incubated with wild-type DNA alone, significantly increased NF-κB-DNA binding was observed in the resistant variants compared to the parental subline (p=0.001). Specific competitor DNA significantly reduced the binding activity in all cell lines (p=0.001), confirming sequence-specificity of the assay for NF-κB binding, but binding activity remained comparable to wild-type DNA alone when wild-type DNA was co-incubated with the non-specific mutant-binding motif (FIG. 5C). The NF-κB-DNA-binding activity was directly related to the level of expression of TNFAIP3 transcript and A20 protein; those cells with most reduction in TNFAIP3 and A20 were those that demonstrated the highest NF-κB DNA-complexing activity (FIG. 5).

Use of SAM

SAM (Significance Analysis of Microarrays) is a statistical technique for finding significant genes in a set of microarray experiments. It was originally proposed by Tusher, Tibshirani and Chu (Ref. 21). The input to SAM is gene expression measurements from a set of microarray experiments, as well as a response variable from each experiment. The response variable may be a grouping like untreated, treated [either unpaired or paired], a multiclass grouping (like breast cancer, lymphoma, colon cancer, etc.), a quantitative variable (like blood pressure) or a possibly censored survival time.

SAM computes a statistic di for each gene i, measuring the strength of the relationship between gene expression and the response variable. It uses repeated permutations of the data to determine if the expression of any genes is significantly related to the response. The cutoff for significance is determined by a tuning parameter delta, chosen by the user based on the false positive rate. One can also choose a fold change parameter, to ensure that called genes change at least a pre-specified amount.

In the One class problem one tests whether the mean gene expression differs from zero. For example each measurement might be the log(red/green) ratio from two labeled samples hydridized to a cDNA chip, with green denoting before treatment and red, after treatment. Here the response measurement is redundant and is set equal to all 1s.

SAM is licensed software. Information on licensing of SAM can be obtained from the Stanford University Office of Licensing (world wide web hypertext transfer protocol otl-.stanford.edu).

Figure 6A:
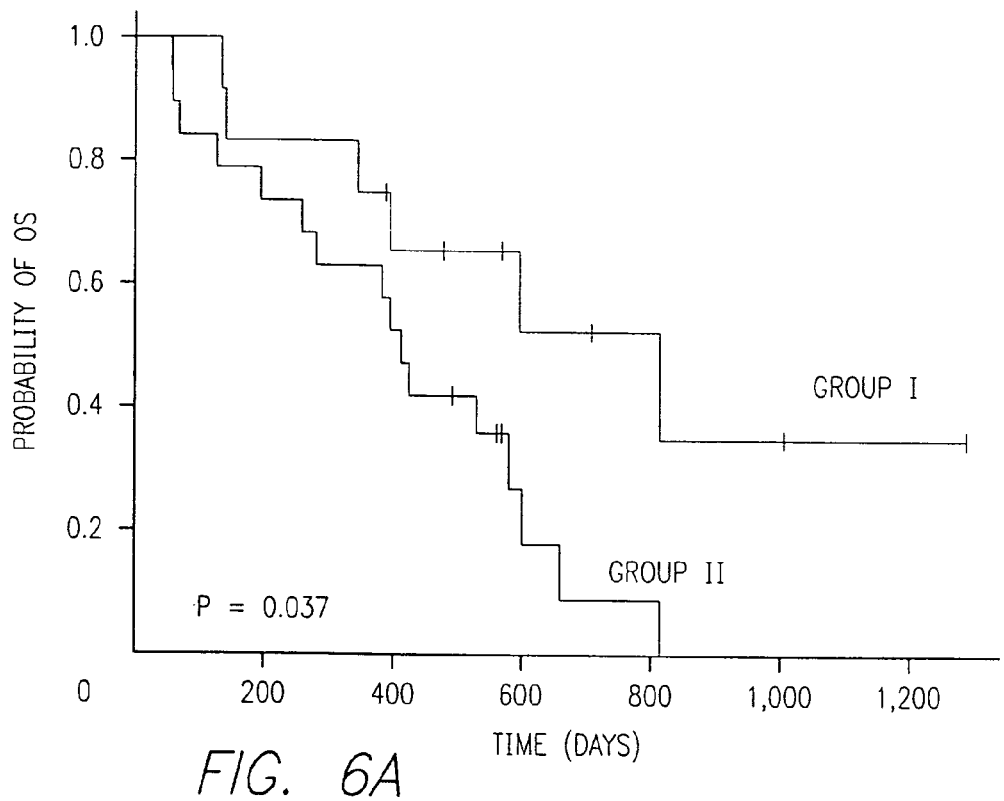
FIG. 6A-C is a series of graphs showing an outcome prediction model in a validation cohort of 31 glioblastomas. 6A, Kaplan-Meier estimates of overall survival in the 31 glioblastomas after subdivision into two groups (group I: 'favorable'; group II: 'unfavorable') according to hierarchical clustering of patients on the expression of 172 of 329 resistance-associated transcripts with >75 percent expression in the tumors, significant difference in outcome between both subgroups (p=0.037, log-rank test). 6B is a Kaplan-Meier plot optimized and simplified predictive model based on the weighted expression of four resistance-associated genes most significantly linked to driving the initial unsupervised patient subgrouping based on the resistance signature. According to Cox proportional-hazards regression analysis, p=0.022 for the model as a continuous variable, and p=0.007 (log-rank test) for the model as a class based on the two major subgroups defined by unsupervised hierarchical clustering. 6C is a Kaplan-Meier plot with partitioning of the tumors into two discrete subgroups (group I: 'favorable'; group II: 'unfavorable') by the four-gene predictor model (p=0.026, log-rank test).

Outcome prediction model based on resistance signature. We evaluated the clinical impact of our resistance signature in an independent cohort of glioblastomas commonly treated with $O^6$-alkylating agents. In order to create a model for predicting survival and response in glioblastomas, we queried the expression status of the 329-transcript resistance signature derived from the cell line models (developed at the Barrow Neurological Institute, Phoenix, Ariz.) in the gene expression profiles of 31 glioblastomas from a different institution (Stanford University Medical Center, Stanford, Calif.). 172 transcripts were expressed in at least 75 percent of the tumors. Unsupervised hierarchical clustering of the tumors based on these transcripts, applying two-way average linkage clustering based on Pearson correlation as a distance metric, resulted in two major tumor subgroups (group I: 12 patients; and group II: 19 patients) with distinct gene expression signatures (data not shown). Highly correlated expression behavior was observed for two major gene clusters (data not shown). One of these clusters demonstrated persistent overexpression in group I and persistent underexpression in group II and included two co-clustering transcripts of TNFAIP3 and one transcript each of NFKBIA, C8orf4, and LIF. The other gene cluster showed overexpression in a subset of tumors in group II and included the MGMT gene. Based on these gene expression signatures we labeled group I as a potentially 'favorable' tumor group and group II as an 'unfavorable' tumor group. Actuarial survival analysis revealed a significant difference in survival between the two groups (p=0.037, log-rank test) (FIG. 6A). The overall survival rates at two years in groups I and II were 0.53 and 0.09, and the median survival times were 814 days and 412 days, respectively (FIG. 6A).

Since a smaller number of genes would make the predictive model more practical we sought to reduce the number of genes in the predictor. A supervised approach via two-class, unpaired SAM analysis was used to identify those genes that were driving the clustering of the tumors. A gene signature based on the top-ten ranking genes that included TNFAIP3 (rank 4) and C8orf 4 (rank 8) was sufficient to drive the unsupervised tumor grouping into two main classes (class error rate: 0.03) and was significantly associated with outcome according to log-likelihood estimate (p=0.016) (data not shown). All but one gene (beta1,4-N-acetylgalactosaminyltransferases IV [Beta4GalNAc-T4]; rank 6) demonstrated reduced expression in the unfavorable tumor subgroup. The top ten genes were: Beta4GalNAc-T4; VAMP4, SDC1, C8orf4, CD44, NPL, SAT, TNFAIP3, FBXO32, and IL1R1.

Figure 6B:
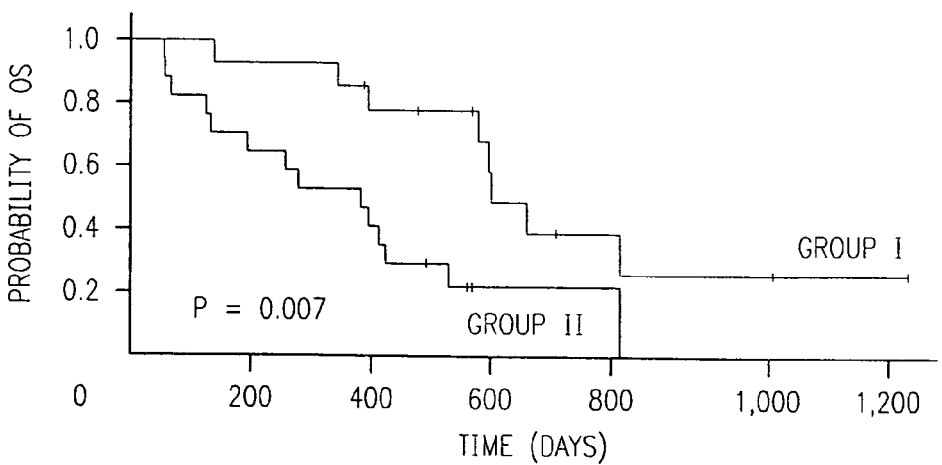

Because a focused number of genes would be particularly amenable to future target modulation, we optimized the model by further minimizing the number of predictive genes based on the SAM ranking. Hierarchical clustering according to the top four genes (CD44 antigen [CD44], F-box protein 32 [FBXO32], syndecan 1 [SDC1], and TNFAIP3) revealed two major tumor subgroups (14 vs. 17 tumors), which demonstrated a significantly different outcome in actuarial survival analysis (p=0.007, log-rank test) (FIG. 6B). Because of the apparent difference in the expression of these genes between the two groups, we performed a Cox proportional-hazards regression analysis of the individual genes, with overall survival as dependent variable. TNFAIP3 and CD44 were significantly associated with outcome when considered as individual continuous variables (p=0.028 and p=0.032, respectively; univariate model). We then examined the combined predictive potential of all four genes, using the average expression of the genes weighted for their relative predictive contribution as indicated by the individual Cox scores. As a continuous variable, the combined predictive model performed better in outcome prognostication compared to the individual genes (p=0.022, univariate model). This model remained significantly associated with patient outcome when taking into account patient age (p=0.025, multivariate model), the most important clinical prognosticator for glioblastomas.

Figure 6C:
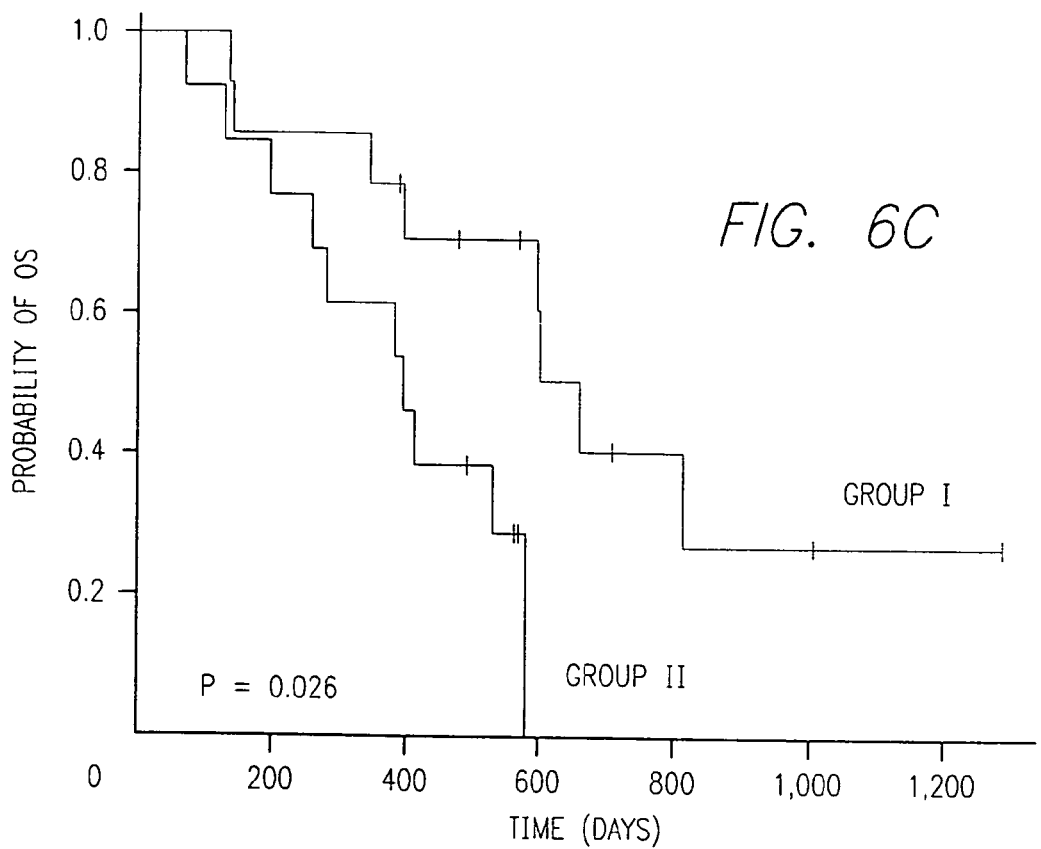

Finally, we examined how the model would perform as a class. We used a schema based on median gene expression to subtype the tumors. Here, the expression of each of the four genes was labeled either 'high' or 'low' based on the median level of all tumors and the number of calls was counted. This approach generated a simplified gene expression profile for each tumor, represented by an integer between 0 and 4 for the number of 'low' and 'high' expression calls. If a tumor had at least three 'low' calls, it was classified as potentially 'unfavorable' (group II); if there were one or less 'low' calls, the tumor was classified as 'favorable' (group I); if a tumor had an equal number of 'low' and 'high' calls, the patient's prognosis was not inferred based on the expression data of the four genes ('non-informative' group III). Such stratification revealed 14 tumors each to fall into groups I and II, and three tumors into group III. Actuarial survival analysis disclosed a strikingly different outcome between groups I and II (p=0.026, log-rank test), with 'favorable' tumors demonstrating a comparably good prognosis (FIG. 6C).

Independent Validation Cohort I

We have validated the prognostic impact of the resistance signature and TNFAIP3 and CD44 as individual factors in an independent glioblastoma v cohort (n=29) from a different institution (University of California at San Francisco=validation Cohort I) profiled on a cDNA microarray platform. Hierarchical clustering of the patients based on the resistance signature again results in two major subgroups, which is primarily driven by a highly correlated gene expression cluster that includes TNFAIP3, NFKBIA, CD44, LIF, and FBXO32 (data not shown). A supervised analysis based on SAM identifies the TNFAIP3 and CD44 genes as top-driving genes for the unsupervised clustering result. Based on the expression pattern of the major gene cluster and our candidate genes, we again labeled the two patient subgroups as having a putatively 'favorable' (Group I) and 'unfavorable' (Group II) prognosis. Actuarial survival curves estimated by the Kaplan-Meier product limit method and log-rank analysis confirm a significant survival difference between the two subgroups (p=0.019) (FIG. 7).

Since the combined unsupervised and supervised analysis had identified TNFAIP3 as a major driving gene for the patient sub-grouping, we compared the TNFAIP3 transcript abundance between both subgroups of Cohort I. This confirms a significant difference in TNFAIP3 abundance distribution between the two groups (p=0.0001, independent t-test) (FIG. 8A), with comparably low abundance present in the 'unfavorable' subgroup (Group II). Stratification of the patient cohort according to median survival also discloses a significant difference in TNFAIP3 abundance between patients with >median survival vs. patients with <median survival (p=0.001, independent t-test) (FIG. 8B), indicating TNFAIP3's survival link beyond patient stratification based on unsupervised clustering.

Figure 9A:
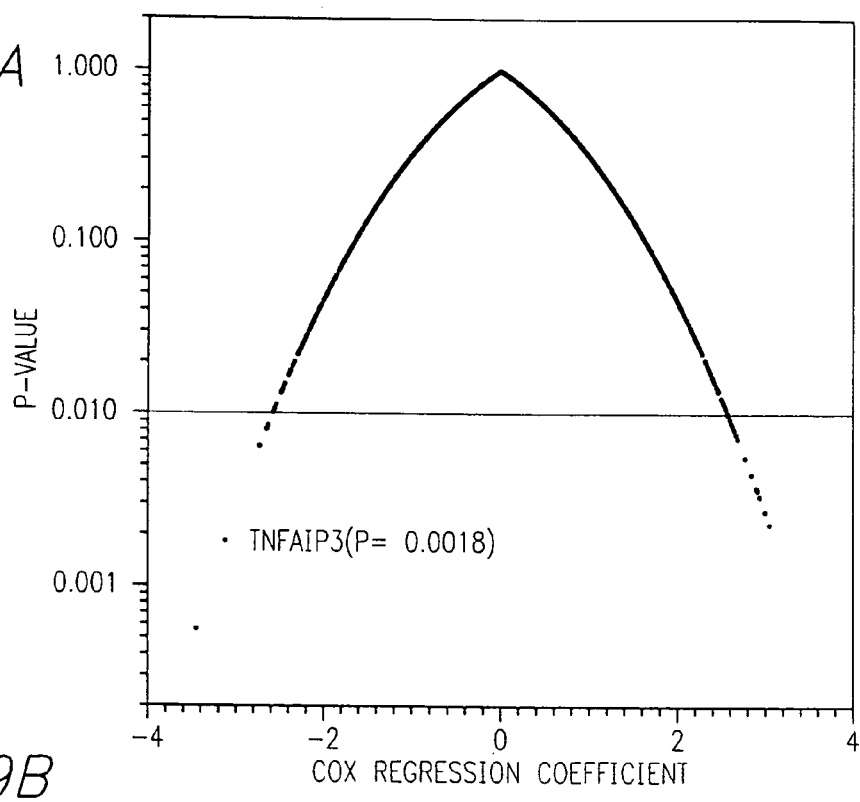
Figure 9B:
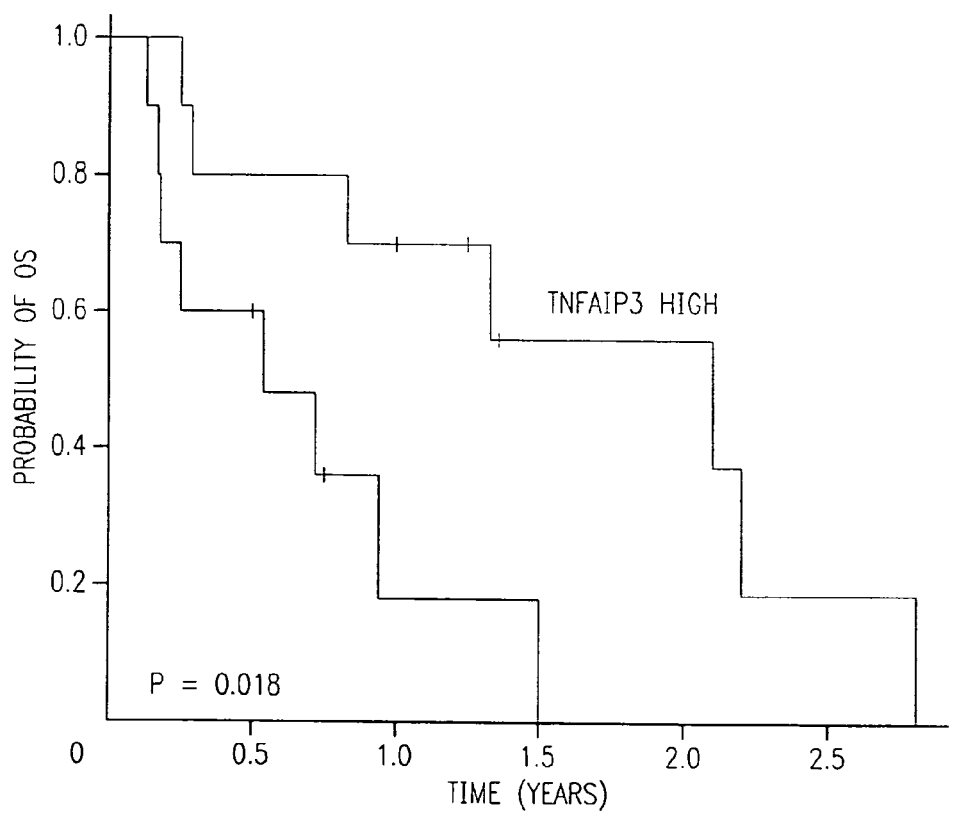

We assessed how TNFAIP3 would perform in terms of survival prediction when considered as an individual factor in Cohort I. Cox-proportional hazards regression analysis with overall survival as dependent variable discloses TNFAIP3 being significantly linked to patient outcome as a continuous variable (p=0.0018) (FIG. 9A). We then performed a global Cox analysis in which we included 2,188 expressed clones representing about 1,800 genes. Univariate analysis for each of these clones reveals TNFAIP3 being the second most significant gene related to patient survival in this genome-wide analysis. Kaplan-Meier estimates based on median TNFAIP3 transcript abundance confirm a significant association between patient outcome and TNFAIP3 in a class model, such that the lower TNFAIP3 the worse the outcome (p=0.018, log-rank test) (FIG. 9B).

Independent Validation Cohorts II+III

Endogenous candidate modulators of canonical NF-κB activation. The pathway leading to the activation of NF-κB involves a complicated network that includes multiple signaling molecules; The recent identification of a wide range of negative regulators of NF-κB has added another layer of complexity in NF-κB activation. One of our major research interests concerned the interrelationship and networking of the endogenous regulators of NF-κB activation, which we had previously linked to cell resistance and patient outcome in glioblastomas. We have therefore evaluated these molecules in terms of their individual and combined capability to predict patient outcome in two additional larger independent validation cohorts of high-grade gliomas from different institutions (MD Anderson Cancer Center=validation Cohort II, University of California, Los Angeles=validation Cohort III), which have been profiled on a commercial microarray platform (Affymetrix Human Genome U 133 A+B Set). Cohort I included 76 high-grade gliomas, of which 55 were glioblastomas (6 without necrosis) and 21 anaplastic astrocytomas. Cohort II included 70 high-grade gliomas, of which 47 were glioblastomas, 8 anaplastic astrocytomas, 9 anaplastic oligodendrogliomas, and 6 anaplastic oligoastrocytomas.

We have initially tested the reliability of the two cohorts for assessing the predictive capacity of the candidate endogenous NF-κB modulators. We have analyzed the survival relationship of common prognosis-related variables, including tumor histology, tumor grade, patient age, and molecular tumor subtypes (MES=mesenchymal, PROLIF=proliferative, PN=proneural), according to univariate Cox proportional hazards regression analysis. This analysis confirms significant survival relationships for all four variables in Cohort II and Cohort III (Tables 3 and 4). Table 3: Cohort II: Survival relationship of tumor histology, tumor grade, patient age, and molecular tumor subtypes (MES=mesenchymal, PROLIF=proliferative, PN=proneural) according to univariate Cox analysis. Significant survival relationship for all four established variables, as a measure of reliability for the cohort.

TABLE 3

Survival Link for Common Prognostic Variables in Cohort II

| Variables | 76 HGG (p=) |
| --- | --- |
| Histology (AA, GBM w necrosis, GBM w/o necrosis) | 0.0002 |
| Grade (III vs. IV) | 0.0007 |
| Age | 0.003 |
| Molecular Subtypes (MES/PROLIF vs. PN) | 0.0001 |

Table 4: Cohort III: Survival relationship of tumor histology, tumor grade, patient age, and molecular tumor subtypes according to univariate Cox analysis. Significant survival relationship for all four established variables, as a measure of reliability for the cohort.

TABLE 4

Survival Link for Common Prognostic Variables in Cohort III

| Variables | 70 HGG (p=) |
| --- | --- |
| Histology (GBM, AA, AO, AOA) | 0.007 |
| Grade (III vs. IV) | 0.0003 |
| Age | 0.0006 |
| Molecular Subtypes (MES/PROLIF vs. PN) | 0.012 |

We then evaluated the outcome relationship of several of our candidate pathway modulators in Cohorts II and III based on multivariate Cox proportional hazards regression models that included the above common prognostic variables and the MGMT gene, the currently most established outcome marker in glioblastomas. These models reveal significant proportional hazard for TNFAIP3 (p=0.012), NFKBIA (p=0.0001), TNIP1 (p=0.014), and NFKBIB (p=0.019) in the subgroup of glioblastomas with necrosis in Cohort II. In addition, NFKBIA shows significant proportional hazard as a continuous variable in a model that included all high-grade gliomas of Cohort II (p=0.002) (Table 5). Comparable analysis in Cohort III discloses significant proportional hazard for TNFAIP3 (p=0.042), NFKBIA (p=0.044), and TNIP1 (p=0.048) in glioblastomas, and proportional hazard for TNIP2 that approaches significance (p=0.064) (Table 11).

Table 5: Cohorts II: Survival relationship of candidate genes (endogenous modulators of NFKB) according to multivariate Cox analysis (inclusion of variables of Table 3 into the analysis plus the MGMT gene, an established prognostic marker in glioblastomas). Significant survival link for NFKBIA, TNFAIP3, TNIP1, and NFIBIB abundance in glioblastomas (GBM); NFKBIA is in addition significantly linked to survival in high-grade gliomas (HGG).

TABLE 5

Survival Link for Candidate Endogenous NF-κB Modulators in Cohort II

| Candidate | Variables | 76 HGG (p=) | 49 GBM (p=) |
|---|---|---|---|
| | | Independent | |
| NFKBIA | Histology or Grade, Age, Molecular subtype, MGMT | 0.002 | 0.0001 |
| TNFAIP3 | Age, Molecular subtype, MGMT | | 0.012 |
| TNIP1 | Age, Molecular subtype, MGMT | | 0.014 |
| NFKBIB | Age, Molecular subtype, MGMT | | 0.019 |

Most of the drugs that the patients received were alkylating agents.

Table 6: Cohort III: Survival relationship of candidate genes (endogenous modulators of NFKB) according to multivariate Cox analysis (inclusion of variables of Table 4 into the analysis plus the MGMT gene, an established prognostic marker in glioblastomas. Significant survival link for NFKBIA, TNFAIP3, and TNIP1 abundance in glioblastomas (GBM) and trend towards significant survival link for TNIP2.

TABLE 6

Survival Link for Candidate Endogenous NF-κB Modulators in Cohort III

| Candidate | Variables | 47 GBM (P=) |
|---|---|---|
| | | Independent |
| NFKBIA | Age, Molecular subtype, MGMT | 0.044 |
| TNFAIP3 | Age, Molecular subtype, MGMT | 0.042 |
| TNIP1 | Age, Molecular subtype, MGMT | 0.048 |
| TNIP2 | Age, Molecular subtype, MGMT | 0.064 |

We then merged the expression data of Cohorts II and III to form one combined Cohort II+III. We also assessed the prognostic capacity of the candidate modulators that emerged as being significant in the above individual cohorts in the combined cohort applying multivariate Cox models. Significant proportional hazard is found for TNFAIP3 (p=0.011), NFKBIA (p<0.00001), TNIP1 (p=0.008), and NFBIB (p=0.030) in glioblastomas, and a trend towards significant proportional hazard for TNIP2 (p=0.122); NFKBIA shows in addition significant proportional hazard in high-grade gliomas (p=0.002) (Table 7).

Table 7: Cohorts II+III: Survival relationship of candidate genes (endogenous modulators of NFKB) according to multivariate Cox analysis. Significant survival link for NFKBIA, NFBIB, TNFAIP3, and TNIP1 abundance in glioblastomas (GBM) and trend towards significant survival link for TNIP2; NFKBIA is in addition significantly linked to survival in high-grade gliomas (HGG).

TABLE 7

Survival Link for Candidate Endogenous NF-κB Modulators in Cohorts II + III

| Candidate | Variables | 146 HGG (p=) | 96 GBM (p=) |
|---|---|---|---|
| | | Independent | |
| NFKBIA | (Grade), Age, Molecular subtype, MGMT | 0.002 | <0.00001 |
| NFKBIB | Age, Molecular subtype, MGMT | — | 0.030 |
| TNFAIP3 | Age, Molecular subtype, MGMT | — | 0.011 |
| TNIP1 | Age, Molecular subtype, MGMT | — | 0.008 |
| TNIP2 | Age, Molecular subtype, MGMT | — | 0.122 |

Figure 10A:
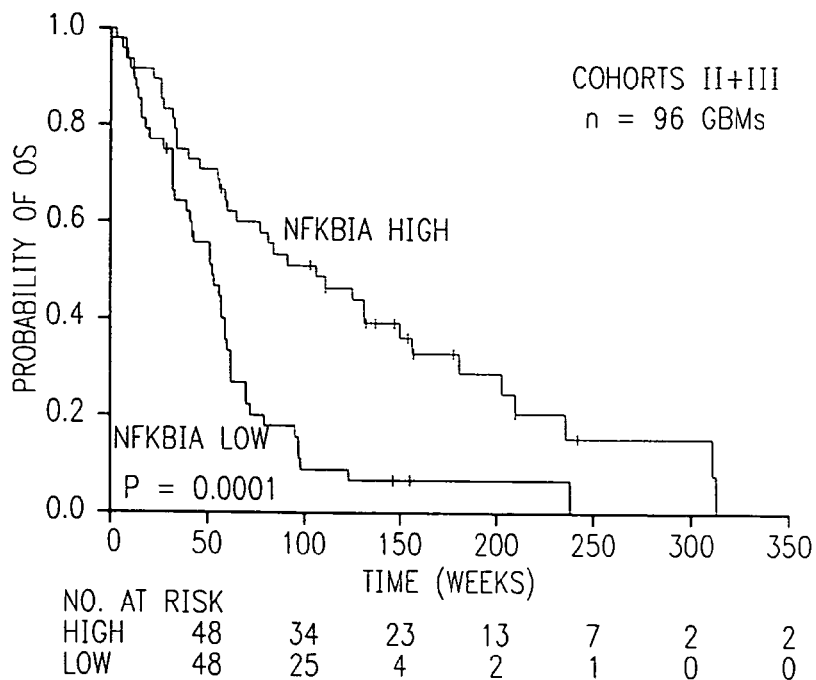
Figure 10B:
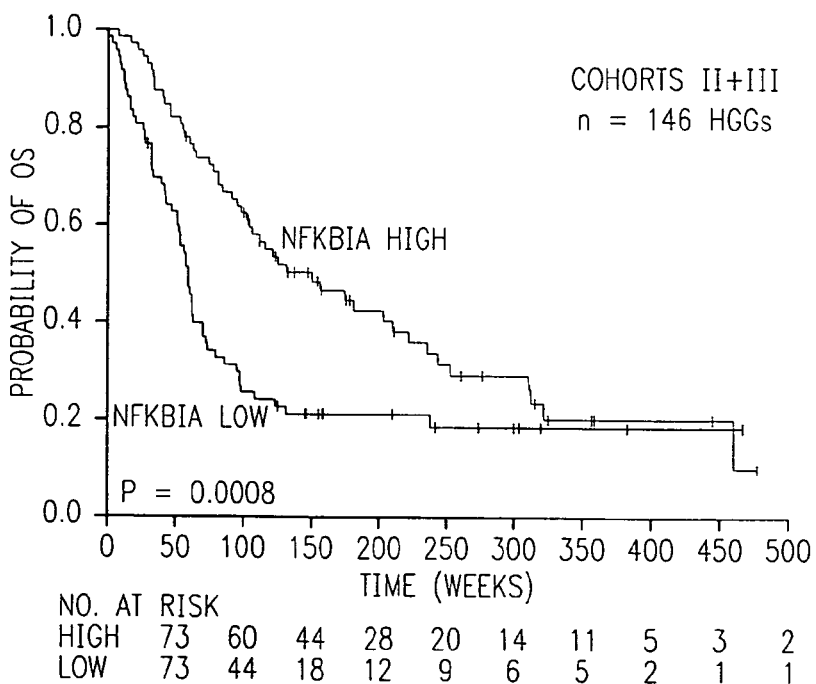
Figure 10C:
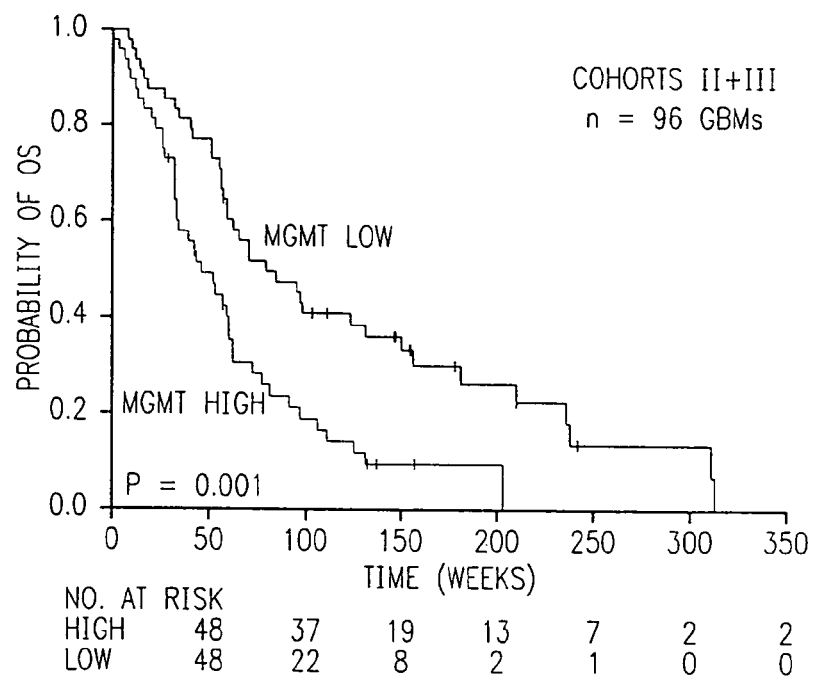
Figure 10D:
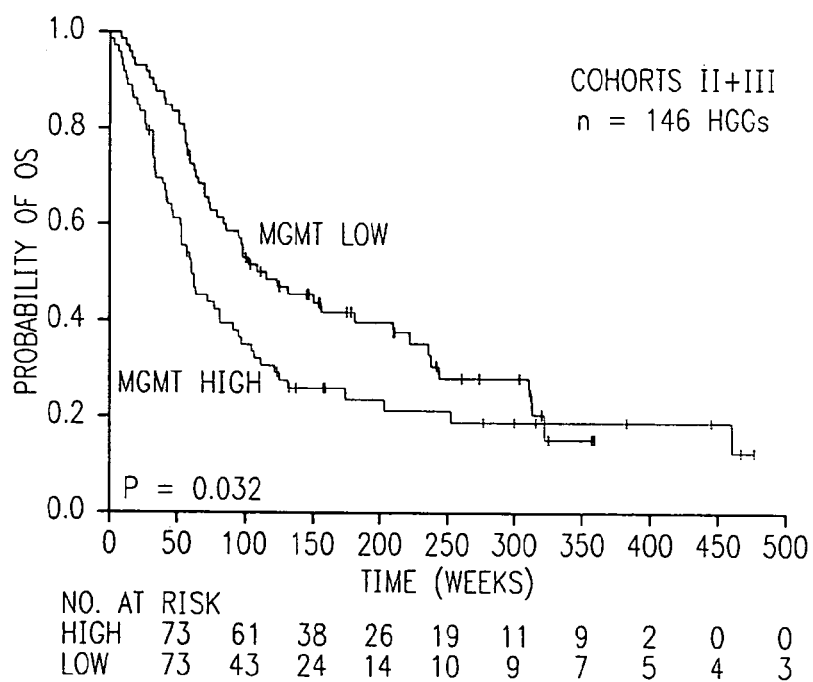

The observed significant survival relationship between NFKBIA and patient outcome not only in glioblastomas but also high-grade gliomas prompted us to examine how this gene may perform in class models for these tumor groups. Kaplan-Meier estimates of overall survival with combined Cohorts II+III stratified based on median NFKBIA abundance disclosed high significance for this gene also in non-parallel hazard functions, both in glioblastomas (p=0.0001, log-rank test) and high-grade gliomas (p=0.0008) (FIGS. 10A and B). We sought to assess the class model performance of NFKBIA versus the MGMT gene. We found NFKBIA to clearly outperform MGMT in predicting patient outcome in two-class models both in glioblastomas (p=0.0001 vs. 0.001, respectively) and high-grade gliomas (p=0.0008 vs. 0.032, respectively) (FIGS. 10C and D).

Figure 11A:
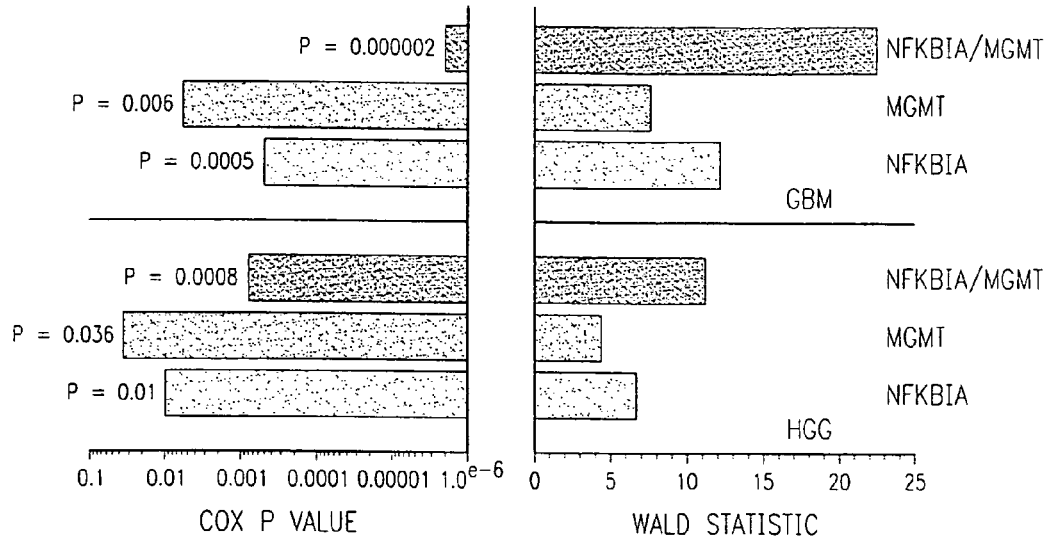
Figure 11B:
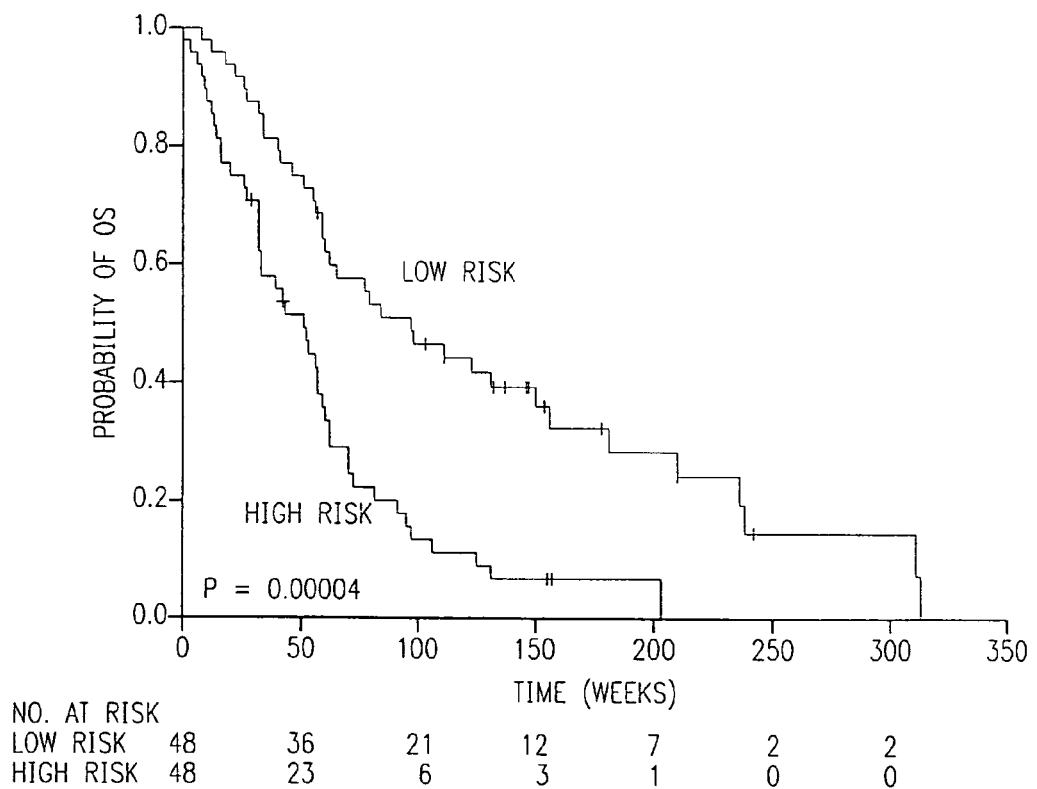

NFKBIA/MGMT combined predictor model. Since NFKBIA and MGMT are constituents of different though potentially complementary pathways relevant to glioma cell survival and resistance, we tested whether a combined predictor model including both genes may outperform the individual genes in terms of predicting glioblastoma outcome. We have used a model in which we have first ranked the abundance in ascending order for NFKBIA and descending order for MGMT, with a low rank for NFKBIA and a high rank for MGMT indicating a putatively high risk for worse outcome. Univariate Cox proportional hazards regression analysis of the sum of ranks showed a significantly greater proportional hazard for the gene combination compared to individual genes both in glioblastomas (p=0.000002) and high-grade gliomas (p=0.000008) (FIG. 11A). A complementary class model based on Kaplan-Meier estimates and log-rank test using the same rank sum model also disclosed a comparably better performance in terms of non-parallel hazard functions for the gene combination compared to the individual genes in glioblastomas (p=0.00004) (FIG. 11B).

Combined Endogenous Modulator Predictor Models

Because of the rising perception of a putatively orchestrated activity and spatiotemporal interaction of multiple endogenous molecules in a multifaceted network of NF-κB pathway modulation, we sought to investigate whether predictor models that include several of their combinations may outperform the individual molecules in the combined Cohorts II+III. We initially focused on modulator combinations for which physical or functional interactions and mutual facilitation of their pathway modulatory ability is known or assumed.

We tested the combination TNFAIP3/TNIP1 since it has lately been suggested that these two genes cooperatively inhibit NF-κB at the level of the IKK complex[8]. TNIP 1 binds IKBKG, the regulatory subunit of the IKK complex, and cooperates with TNFAIP3 in inhibiting NF-κB by physically linking TNFAIP3 to IKBKG and by and facilitating TNFAIP3-mediated de-ubiquitination of IKBKB. Reduced levels of TNIP1 affect the ability of TNFAIP3 to de-ubiquitinate IKBKG and, consequently the TNFAIP3-mediated inhibition of NF-κB. In turn, reduced levels of TNFAIP3 impair the ability of TNIP1 to inhibit NF-κB activation[8]. Consistent with these observations, we found a combined predictor model of both genes in glioblastomas to show greater significance in terms of proportional survival regression in multivariate Cox analysis compared to the individual genes (p=0.004) (Table 8).

We also tested the combination TNFAIP3/TNIP2 because of some indication that TNIP2 may contribute to the NF-κB inhibitory function of TNFAIP3 and functional redundancy between TNIP1 and TNIP2 (Ref. 9). Loss of binding of either TNIP1 or TNIP2 has been found to correlate with complete loss of TNFAIP3's ability to inhibit NF-κB activation (ref. 10). A combined multivariate Cox model confirmed a slightly greater proportional survival regression compared to the individual genes in glioblastomas p=0.010)

We also tested the combination NFKBIA/NFKBIB because of putatively complementary roles of both genes in regulating NF-κB in a biphasic fashion (Ref. 11). NFKBIA and NFKBIB defer in their signal response characteristics. While NFKBIB is thought to constitutively regulate the persistent response in a biphasic activation of NF-κB, NFKBIA appears to be involved in regulating rapid, transient NF-κB activation (Ref. 12). NFKBIA participates in an auto-regulatory loop of NF-κB activation due to the presence of several κB enhancer elements present in the 5' flanking region of the gene, which mediate its transcriptional stimulation upon NF-κB activation (ref. 13). NFKBIA is thus responsible for a strong negative feedback that allows for a fast turn-off of the NF-κB response, whereas NFKBIB functions to reduce the system's oscillatory potential and stabilizes NF-κB responses during longer stimulations (Ref. 14). We reasoned that information regarding the combined abundance of both genes may enable refined predictions regarding NF-κB activation state and therefore putatively patient survival. In line with this notion, we found a combined predictor model of both genes in glioblastomas to show greater significance in terms of proportional survival regression in multivariate Cox analysis compared to the individual genes (p=0.000005) (Table 8).

Table 8: Cohorts II+III: Survival relationship for various (functionally interacting) combinations of candidate genes according to multivariate Cox analysis. Combined predictor models for TNFAIP3+TNIP1, TNFAIP3+TNIP2, and NFKBIA+NFKBIB outperform the survival predictive capacity of the individual genes (indicated parenthesis).

TABLE 8

Combined NF-κb Modulator Predictor Models in Cohorts II + III

| Candidate | Variables | 96 GBM (p=) Independent |
|---|---|---|
| TNFAIP3 + TNIP1 (0.011 + 0.008) | Age, Molecular subtype, MGMT | 0.004 |
| TNFAIP3 + TNIP2 (0.011 + 0.122) | Age, Molecular subtype, MGMT | 0.010 |
| NFKBIA + NFKBIB (<0.00001 + 0.030) | Age, Molecular subtype, MGMT | <0.000005 |

Figure 12A:
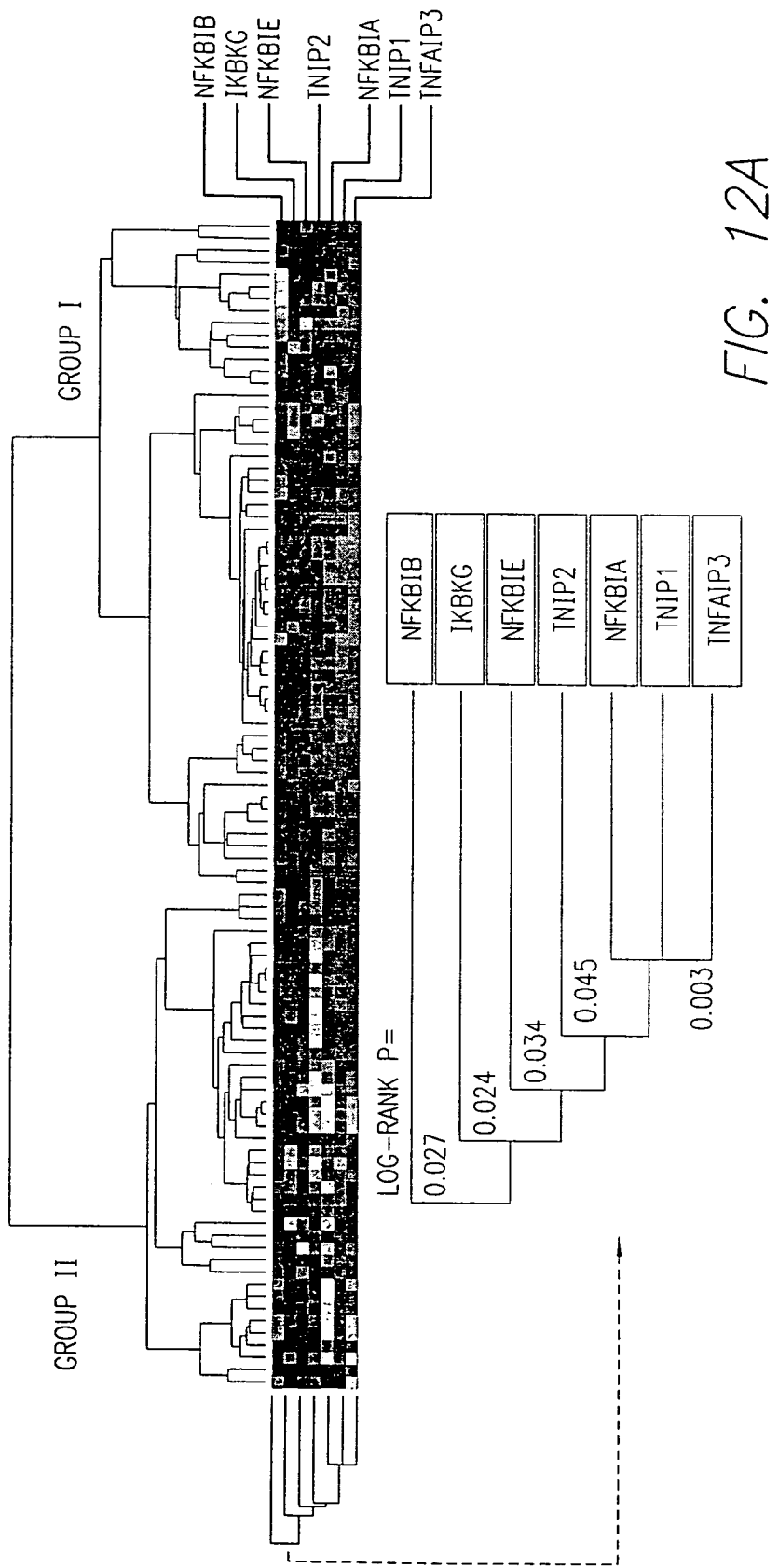
Figure 12B:
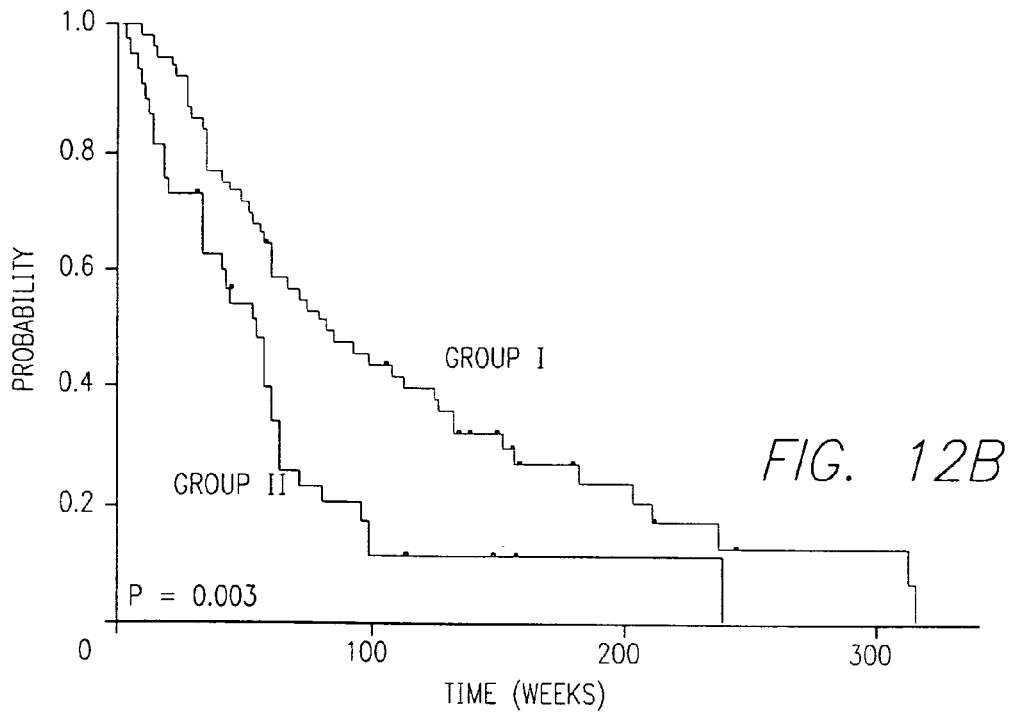

We next examined the expression pattern of seven endogenous modulators of NF-κB (TNFAIP3, NFKBIA, TNIP1, NFKBIB, TNIP2, NFKBIE, and IKBKG) and how these genes may perform in non-parallel hazard functions in the glioblastomas of Cohorts II+III. We used hierarchical clustering as an unsupervised means to evaluate their potential as combined class predictors of patient survival. This learning algorithm revealed correlated expression patterns for most of the modulators across the tumor panel (FIG. 12A, upper panel, gene clustering dendrogram) with NFKBIA, TNFAIP3, and TNIP1 showing the most highly correlated expression behavior. It also revealed the clustering of the glioblastomas into major subgroups (FIG. 12, upper panel). Actuarial survival analysis disclosed a significant difference in the outcome of the two subgroups (p=0.027, log-rank test) with the high-abundance subgroup showing a comparably favorable outcome (FIG. 12A, lower panel). We then pursued a reductionistic approach in which we eliminated one modulator gene in a stepwise manner in the order of least correlated expression behavior (first NFKBIB, then IKBKG, then NFKBIE, then TNIP2) and then re-clustered the tumors. This stepwise model would test the self-sufficiency of the remaining genes in sub-classifying the tumors into prognostic groups. Such stepwise gene reduction resulted in two major subgroups in each elimination step. Actuarial survival analysis of the two major clustering tumor subgroups at each step indicated the significant relationship to patient survival of all predictor models (7-gene to 3-gene models) (FIG. 12A, lower panel) and the most significant survival link for the 3-gene (NFKBIA, TNFAIP3, TNIP1) predictor (FIG. 12B).

We finally evaluated the performance of a four-gene predictor (TNFAIP3, NFKBIA, TNIP1, and TNIP2) showing highest expression correlation across the glioblastomas (Cohorts II+III in the unsupervised classification approach. Kaplan-Meier estimates of overall survival based on stratifying patients according to median modulator abundance particularly indicate a refined ability—compared to NFKBIA alone—to identify those patients which die particularly early (early failures)—and thus strong need for additional therapeutic intervention—compared to those who show a longer-term survival.

In addition to the usual Cox-Mantel log-rank test two additional comparison factors were used: Gehan-Breslow test and Tarone-Ware test; The Gehan-Breslow test gives more weight to earlier failures (deaths), while the Mantel-Cok test gives equal weight to all failures. The Tarone-Ware tests falls in between. The Gehan-Breslow test is more powerful with data from a lognormal survival distribution, but may have low power if there is heavy censoring. The Tarone-Ware test, with its intermediate weighting scheme, is designed to have good power across a wide range of survival functions, although it may not be the most powerful of the three tests in a particular situation.

Kaplan-Meier estimates of overall survival after stratification according to median modulator abundance particularly indicate a refined discretization of early failures compared to NFKBIA alone, which performed best as an individual variable (FIG. 10A). In accord with this notion, actuarial survival analysis based on the Gehan-Breslow test shows a highly significant p value (p=0.0001, vs. NFKBIA alone: p=0.001). This is confirmed by a complementary Tarone-Ware test (p=0.00008, vs. NFKBIA alone: p=0.0003).

Taken collectively, these data indicate an increasing complexity and linkage of several regulatory molecules to patient outcome that interact physical and functionally in a cooperative fashion to block activation of NF-κB. We found that for many of these molecules, combined predictor models outperform the predictive power of the individual molecules. This observation is consistent with recent evidence suggesting the cooperation of these endogenous inhibitors in a negative feedback regulation of NF-κB activation and a mutual facilitation of their repressive ability. In terms of outcome prediction, we found several of these inhibitors to outperform established clinical and morphological prognostic variables such as patient age and tumor grade (III vs. IV), as well as the $O^6$-methylguanine DNA methyltransferase (MGMT) gene, the currently most established outcome marker in glioblastomas. These findings raise the hope for this regulatory network as an amenable target to modulate NF-κB-mediated resistance in glioblastoma cells, with the ultimate goal of increasing the efficacy of chemotherapy in patients harboring these challenging tumors.

Testing of Tissue Samples

The work described above provides a number of different materials that can be used to test tissue samples for the presence of the above-described gene expression signature. This signature has been correlated with resistance to alkylating agents. These materials may take the form of antibodies, DNA probes, primers for PCR or other amplification, and similar materials. The gene expression signatures may be embodies as a single gene expression, namely TNFAIP3, as a small set of highly significant genes, as set forth below in Table 9, or as a large set of genes analyzed in the context of a more global gene expression, as described in the table of 286 resistance genes set forth in Table 9 below. That is, a microarray or probe set representing an entire human gene expression set (about 20,000-40,000 gene transcripts) is analyzed for increased or decreased expression of the listed genes, compared to a normal (e.g. non-cancerous) control. Variations within these embodiments will be apparent to those skilled in the art, given the present disclosure.

TABLE 9

List of 286 genes having altered expression in resistant cells

| Unigene ID | Gene | Name (No. of clones) | Status in resistant cells |
|---|---|---|---|
| Hs.368243 | ABCC2 | "ATP-binding cassette, sub-family C (CFTR/MRP), member 2 (1)" | downexpressed |
| Hs.132992 | ABCG5 | "ATP-binding cassette, sub-family G (WHITE), member 5 (sterolin 1) (1)" | downexpressed |
| Hs.521212 | AKR1B1 | "Aldo-keto reductase family 1, member B1 (aldose reductase) (1)" | downexpressed |
| Hs.558319 | AKR1C1 | "Aldo-keto reductase family 1, member C1 (dihydrodiol dehydrogenase 1; 20-alpha (3-alpha)-hydroxysteroid dehydrogenase) (1)" | downexpressed |
| Hs.459538 | ALDH1A3 | "Aldehyde dehydrogenase 1 family, member A3 (1)" | downexpressed |
| Hs.355957 | ANK2 | "Ankyrin 2, neuronal (1)" | overexpressed |
| Hs.448589 | ANKRD1 | Ankyrin repeat domain 1 (cardiac muscle) (1) | overexpressed |
| Hs.121592 | AP1S2 | "Adaptor-related protein complex 1, sigma 2 subunit (1)" | downexpressed |
| Hs.158932 | APC | Adenomatosis polyposis coli (2) | overexpressed |
| Hs.286221 | ARF1 | ADP-ribosylation factor 1 (1) | overexpressed |
| Hs.6838 | ARHE | Rho family GTPase 3 (1) | downexpressed |
| Hs.515249 | ARRDC2 | Arrestin domain containing 2 (1) | downexpressed |
| Hs.13205 | B3GTL | Beta 3-glycosyltransferase-like (1) | overexpressed |
| Hs.478588 | BCL6 | B-cell CLL/lymphoma 6 (zinc finger protein 51) (1) | downexpressed |
| Hs.100686 | BCMP11 | Breast cancer membrane protein 11 (1) | downexpressed |
| Hs.148074 | Beta4GalNAc-T4 | "Beta1,4-N-acetylgalactosaminyltransferases IV (1)" | downexpressed |
| Hs.296648 | BMP5 | Bone morphogenetic protein 5 (1) | downexpressed |
| Hs.460095 | C16orf45 | Chromosome 16 open reading frame 45 (1) | downexpressed |
| Hs.348553 | C19orf33 | Hypothetical LOC541469 protein (1) | overexpressed |
| Hs.283683 | C8orf4 | Chromosome 8 open reading frame 4 (1) | downexpressed |
| Hs.292737 | C9orf47 | "Endothelial differentiation, sphingolipid G-protein-coupled receptor, 3 (1)" | downexpressed |
| Hs.459642 | CACNA1H | "Calcium channel, voltage-dependent, alpha 1H subunit (1)" | downexpressed |
| Hs.397705 | CAMTA1 | Calmodulin binding transcription activator 1 (1) | downexpressed |
| Hs.303649 | CCL2 | Chemokine (C—C motif) ligand 2 (1) | downexpressed |
| Hs.512306 | CCL4L | Chemokine (C—C motif) ligand 4 (1) | downexpressed |
| Hs.251526 | CCL7 | Chemokine (C—C motif) ligand 7 (1) | downexpressed |
| Hs.271387 | CCL8 | Chemokine (C—C motif) ligand 8 (1) | downexpressed |
| Hs.523852 | CCND1 | Cyclin D1 (2) | downexpressed |
| Hs.502328 | CD44 | CD44 antigen (homing function and Indian blood group system) (2) | downexpressed |
| Hs.443057 | CD53 | CD53 antigen (1) | downexpressed |
| Hs.436040 | CDH13 | "Cadherin 13, H-cadherin (heart) (1)" | downexpressed |
| Hs.106070 | CDKN1C | "Cyclin-dependent kinase inhibitor 1C (p57, Kip2) (2)" | downexpressed |
| Hs.220864 | CHD2 | Chromodomain helicase DNA binding protein 2 (1) | downexpressed |
| Hs.387794 | ChGn | "Chondroitin beta1,4 N-acetylgalactosaminyltransferase (1)" | downexpressed |
| Hs.134830 | COL8A1 | "Collagen, type VIII, alpha 1 (1)" | downexpressed |
| Hs.464422 | COLEC12 | Collectin sub-family member 12 (1) | downexpressed |
| Hs.78068 | CPZ | Carboxypeptidase Z (1) | downexpressed |
| Hs.1349 | CSF2 | Colony stimulating factor 2 (granulocyte-macrophage) (1) | downexpressed |
| Hs.83577 | CSRP3 | Cysteine and glycine-rich protein 3 (cardiac LIM protein) (1) | downexpressed |
| Hs.789 | CXCL1 | "Chemokine (C—X—C motif) ligand 1 (melanoma growth stimulating activity, alpha) (2)" | downexpressed |
| Hs.75765 | CXCL2 | Chemokine (C—X—C motif) ligand 2 (1) | downexpressed |
| Hs.154654 | CYP1B1 | "Cytochrome P450, family 1, subfamily B, polypeptide 1 (2)" | downexpressed |
| Hs.15476 | DEF6 | Differentially expressed in FDCP 6 homolog (mouse) (1) | downexpressed |
| Hs.289347 | DHRS3 | Dehydrogenase/reductase (SDR family) member 3 (1) | downexpressed |
| Hs.107382 | DHX37 | DEAH (Asp-Glu-Ala-His) box polypeptide 37 (1) | overexpressed |
| Hs.249600 | DLGAP4 | "Discs, large (*Drosophila*) homolog-associated protein 4 (1)" | downexpressed |

TABLE 9-continued

List of 286 genes having altered expression in resistant cells

| Unigene ID | Gene | Name (No. of clones) | Status in resistant cells |
|---|---|---|---|
| Hs.350507 | DMRTC2 | DMRT-like family C2 (1) | overexpressed |
| Hs.532446 | DNA2L | DNA2 DNA replication helicase 2-like (yeast) (1) | downexpressed |
| Hs.526500 | DNAH3 | "Dynein, axonemal, heavy polypeptide 3 (1)" | downexpressed |
| Hs.519873 | DSP | Desmoplakin (1) | overexpressed |
| Hs.130988 | DYRK1B | Dual-specificity tyrosine-(Y)-phosphorylation regulated kinase 1B (1) | overexpressed |
| Hs.126667 | EDG2 | "Endothelial differentiation, lysophosphatidic acid G-protein-coupled receptor, 2 (2)" | downexpressed |
| Hs.183713 | EDNRA | Endothelin receptor type A (1) | downexpressed |
| Hs.502306 | EHF | Ets homologous factor (1) | downexpressed |
| Hs.478553 | EIF4A2 | "Eukaryotic translation initiation factor 4A, isoform 2 (1)" | downexpressed |
| Hs.200100 | Ells1 | Hypothetical protein Ells1 (1) | downexpressed |
| Hs.304578 | ELMO1 | "Engulfment and cell motility 1 (ced-12 homolog, C. elegans) (1)" | downexpressed |
| Hs.435765 | ENPEP | Glutamyl aminopeptidase (aminopeptidase A) (1) | downexpressed |
| Hs.22634 | ETV1 | Ets variant gene 1 (1) | downexpressed |
| Hs.165830 | EVI1 | Ecotropic viral integration site 1 (1) | overexpressed |
| Hs.150956 | EXTL1 | Exostoses (multiple)-like 1 (1) | downexpressed |
| Hs.356216 | FAM46C | "Family with sequence similarity 46, member C (1)" | downexpressed |
| Hs.494529 | FANCC | "Fanconi anemia, complementation group C (1)" | downexpressed |
| Hs.46730 | FB14 | Chromosome 4 open reading frame 12 (2) | overexpressed |
| Hs.403933 | FBXO32 | F-box protein 32 (2) | downexpressed |
| Hs.443687 | FHL2 | Four and a half LIM domains 2 (1) | downexpressed |
| Hs.497841 | FLJ10052 | Sushi domain containing 4 (1) | downexpressed |
| Hs.480712 | FLJ10378 | "La ribonucleoprotein domain family, member 2 (1)" | downexpressed |
| Hs.437460 | FLJ10385 | WD repeat domain 79 (1) | overexpressed |
| Hs.471918 | FLJ23231 | Zinc finger CCCH-type containing 12A (1) | downexpressed |
| Hs.122115 | FLJ33915 | Hypothetical protein FLJ33915 (1) | overexpressed |
| Hs.558719 | FLJ34154 | Hypothetical protein FLJ34154 (1) | downexpressed |
| Hs.269546 | FLJ40298 | Hypothetical protein FLJ40298 (1) | downexpressed |
| Hs.527816 | FMN1 | Formin 1 (1) | downexpressed |
| Hs.303476 | FMO5 | "Chaperonin containing TCP1, subunit 8 (theta) (1)" | overexpressed |
| Hs.484423 | FOXF2 | Forkhead box F2 (1) | downexpressed |
| Hs.9914 | FST | Follistatin (2) | downexpressed |
| Hs.118722 | FUT8 | "Fucosyltransferase 8 (alpha (1,6) fucosyltransferase) (1)" | downexpressed |
| Hs.116250 | GABRA2 | "Gamma-aminobutyric acid (GABA) A receptor, alpha 2 (1)" | downexpressed |
| Hs.411308 | GALNTL2 | UDP-N-acetyl-alpha-D-galactosamine:polypeptide N-acetylgalactosaminyltransferase-like 2 (1) | downexpressed |
| Hs.29304 | GARNL3 | GTPase activating Rap/RanGAP domain-like 3 (1) | downexpressed |
| Hs.32973 | GLRB | "Glycine receptor, beta (1)" | overexpressed |
| Hs.344151 | GOLGA4 | "Golgi autoantigen, golgin subfamily a, 4 (1)" | downexpressed |
| Hs.508364 | GPC5 | Glypican 5 (1) | downexpressed |
| Hs.148685 | GPRC5B | "G protein-coupled receptor, family C, group 5, member B (2)" | downexpressed |
| Hs.98206 | GREM2 | "Gremlin 2, cysteine knot superfamily, homolog (Xenopus laevis) (1)" | downexpressed |
| Hs.58650 | HHAT | Hedgehog acyltransferase (1) | overexpressed |
| Hs.171806 | HOXB3 | Homeo box B3 (1) | downexpressed |
| Hs.534538 | HSPB6 | "Heat shock protein, alpha-crystalline-related, B6 (1)" | downexpressed |
| Hs.556605 | ID2B | "Inhibitor of DNA binding 2B, dominant negative helix-loop-helix protein (1)" | downexpressed |
| Hs.76095 | IER3 | Immediate early response 3 (1) | downexpressed |
| Hs.20315 | IFIT1 | Interferon-induced protein with tetratricopeptide repeats 1 (1) | overexpressed |
| Hs.369982 | IGFBP5 | Insulin-like growth factor binding protein 5 (2) | downexpressed |
| Hs.370510 | IGSF4 | "Immunoglobulin superfamily, member 4 (2)" | downexpressed |
| Hs.467304 | IL11 | Interleukin 11 (1) | downexpressed |
| Hs.557403 | IL1R1 | "Interleukin 1 receptor, type I (2)" | downexpressed |
| Hs.512234 | IL6 | "Interleukin 6 (interferon, beta 2) (1)" | downexpressed |
| Hs.28792 | INHBA | "Inhibin, beta A (activin A, activin AB alpha polypeptide) (1)" | downexpressed |
| Hs.289293 | INM01 | Chromosome 8 open reading frame 42 (1) | overexpressed |
| Hs.411865 | IPO4 | Importin 4 (1) | overexpressed |
| Hs.440497 | KCNAB2 | "Potassium voltage-gated channel, shaker-related subfamily, beta member 2 (1)" | downexpressed |
| Hs.24040 | KCNK3 | "Potassium channel, subfamily K, member 3 (1)" | downexpressed |
| Hs.525529 | KCNMB4 | "Potassium large conductance calcium-activated channel, subfamily M, beta member 4 (1)" | overexpressed |
| Hs.493804 | KIAA0258 | KIAA0258 (1) | overexpressed |
| Hs.49658 | KIAA0495 | KIAA0495 (1) | downexpressed |
| Hs.284232 | KIAA0720 | "Pleckstrin homology domain containing, family G (with RhoGef domain) member 5 (1)" | downexpressed |
| Hs.136102 | KIAA0853 | KIAA0853 (1) | downexpressed |
| Hs.472285 | KIAA1272 | Chromosome 20 open reading frame 74 (1) | downexpressed |
| Hs.461405 | KIAA1576 | KIAA1576 protein (1) | downexpressed |

TABLE 9-continued

List of 286 genes having altered expression in resistant cells

| Unigene ID | Gene | Name (No. of clones) | Status in resistant cells |
|---|---|---|---|
| Hs.6829 | KIAA1644 | KIAA1644 protein (1) | downexpressed |
| Hs.369522 | KIAA1838 | KIAA1838 (1) | downexpressed |
| Hs.150549 | KIAA1893 | G protein-regulated inducer of neurite outgrowth 1 (1) | downexpressed |
| Hs.533782 | KRT8 | Keratin 8 (1) | overexpressed |
| Hs.470126 | KYNU | Kynureninase (L-kynurenine hydrolase) (3) | downexpressed |
| Hs.506829 | LASS6 | LAG1 longevity assurance homolog 6 (S. cerevisiae) (1) | overexpressed |
| Hs.154078 | LBP | Lipopolysaccharide binding protein (1) | downexpressed |
| Hs.381099 | LCP1 | Lymphocyte cytosolic protein 1 (L-plastin) (1) | overexpressed |
| Hs.23748 | LDB2 | LIM domain binding 2 (1) | downexpressed |
| Hs.46458 | LEPREL2 | Leprecan-like 2 (1) | downexpressed |
| Hs.124316 | LHFPL3 | Lipoma HMGIC fusion partner-like 3 (1) | downexpressed |
| Hs.2250 | LIF | Hypothetical protein MGC20647 (1) | downexpressed |
| Hs.187694 | LMAN1L | "Lectin, mannose-binding, 1 like (1)" | downexpressed |
| Hs.444179 | LMTK2 | Lemur tyrosine kinase 2 (1) | overexpressed |
| Hs.558716 | LOC283130 | Hypothetical protein LOC283130 (1) | overexpressed |
| Hs.22907 | LOC283824 | Hypothetical protein LOC283824 (1) | downexpressed |
| Hs.556244 | LOC492304 | Putative insulin-like growth factor II associated protein (1) | downexpressed |
| Hs.15200 | LOC64744 | Stromal membrane-associated protein 1-like (1) | downexpressed |
| Hs.101651 | LOC90133 | Keratin 8-like 2 (1) | overexpressed |
| Hs.446179 | LSM8 | "LSM8 homolog, U6 small nuclear RNA associated (S. cerevisiae) (1)" | downexpressed |
| Hs.187199 | MALAT1 | Metastasis associated lung adenocarcinoma transcript 1 (non-coding RNA) (1) | downexpressed |
| Hs.89983 | MASP1 | Mannan-binding lectin seine peptidase 1 (C4/C2 activating component of Ra-reactive factor) (2) | downexpressed |
| Hs.47668 | MDS006 | X 006 protein (1) | downexpressed |
| Hs.534463 | MEG3 | **Maternally expressed 3 (1) | downexpressed |
| Hs.99196 | MGC11324 | Hypothetical protein MGC11324 (1) | downexpressed |
| Hs.38516 | MGC15887 | "Family with sequence similarity 89, member A (2)" | downexpressed |
| Hs.26670 | MGC17330 | HGFL gene (1) | downexpressed |
| Hs.459704 | MGC21881 | Hypothetical protein MGC21881 (1) | overexpressed |
| Hs.48343 | MGC26963 | Hypothetical protein MGC26963 (1) | overexpressed |
| Hs.488679 | MGC3036 | Hypothetical protein MGC3036 (2) | overexpressed |
| Hs.351133 | MGC35558 | Hypothetical protein MGC35558 (1) | overexpressed |
| Hs.368934 | MGC40157 | Hypothetical protein MGC40157 (1) | downexpressed |
| Hs.501522 | MGMT | O-6-methylguanine-DNA methyltransferase (1) | overexpressed |
| Hs.81874 | MGST2 | Microsomal glutathione S-transferase 2 (1) | overexpressed |
| Hs.102406 | MLPH | Melanophilin (1) | downexpressed |
| Hs.248267 | MPST | Mercaptopyruvate sulfurtransferase (1) | downexpressed |
| Hs.190086 | MRCL3 | Myosin regulatory light chain MRCL3 (1) | overexpressed |
| Hs.89404 | MSX2 | Msh homeo box homolog 2 (Drosophila) (1) | downexpressed |
| Hs.534330 | MT1E | Metallothionein 1E (functional) (1) | downexpressed |
| Hs.513626 | MT1F | Metallothionein 1F (functional) (1) | downexpressed |
| Hs.374950 | MT1X | Metallothionein 1X (1) | downexpressed |
| Hs.434418 | MYT1L | Myelin transcription factor 1-like (1) | overexpressed |
| Hs.324271 | NAPE-PLD | N-acyl-phosphatidylethanolamine-hydrolyzing phospholipase D (1) | overexpressed |
| Hs.439671 | NBL1 | "Neuroblastoma, suppression of tumorigenicity 1 (1)" | downexpressed |
| Hs.371987 | NFAT5 | "Nuclear factor of activated T-cells 5, tonicity-responsive (1)" | downexpressed |
| Hs.370359 | NFIB | Nuclear factor I/B (1) | overexpressed |
| Hs.257970 | NFIX | Nuclear factor I/X (CCAAT-binding transcription factor) (1) | downexpressed |
| Hs.81328 | NFKBIA | "Nuclear factor of kappa light polypeptide gene enhancer in B-cells inhibitor, alpha (1)" | downexpressed |
| Hs.29444 | NID67 | Putative small membrane protein NID67 (1) | downexpressed |
| Hs.310429 | NIN | Ninein (GSK3B interacting protein) (1) | overexpressed |
| Hs.240951 | NKD2 | Naked cuticle homolog 2 (Drosophila) (1) | downexpressed |
| Hs.502564 | NOTCH2NL | Notch homolog 2 (Drosophila) N-terminal like (1) | overexpressed |
| Hs.156832 | NPAS2 | Neuronal PAS domain protein 2 (1) | downexpressed |
| Hs.496969 | NPL | N-acetylneuraminate pyruvate lyase (dihydrodipicolinate synthase) (1) | downexpressed |
| Hs.514556 | NPTX1 | Neuronal pentraxin I (1) | downexpressed |
| Hs.519445 | NR2F1 | "Nuclear receptor subfamily 2, group F, member 1 (1)" | downexpressed |
| Hs.202247 | OTP | Orthopedia homolog (Drosophila) (1) | downexpressed |
| Hs.494928 | PAPPA | "Pregnancy-associated plasma protein A, pappalysin 1 (1)" | downexpressed |
| Hs.489615 | PBEF1 | Pre-B-cell colony enhancing factor 1 (1) | downexpressed |
| Hs.130757 | PCDHB15 | Protocadherin beta 15 (1) | overexpressed |
| Hs.533023 | PCDHB2 | Protocadherin beta 2 (1) | overexpressed |
| Hs.370661 | PDE5A | "Phosphodiesterase 5A, cGMP-specific (1)" | downexpressed |
| Hs.23363 | PGM2 | Phosphoglucomutase 2 (1) | overexpressed |
| Hs.307835 | PGM5 | Phosphoglucomutase 5 (1) | downexpressed |
| Hs.524271 | PHC2 | Polyhomeotic-like 2 (Drosophila) (1) | downexpressed |
| Hs.464971 | PIK3C3 | "Phosphoinositide-3-kinase, class 3 (1)" | downexpressed |
| Hs.518451 | PIK3CD | "Phosphoinositide-3-kinase, catalytic, delta polypeptide (1)" | downexpressed |

TABLE 9-continued

List of 286 genes having altered expression in resistant cells

| Unigene ID | Gene | Name (No. of clones) | Status in resistant cells |
|---|---|---|---|
| Hs.231295 | PITPNC1 | "Phosphatidylinositol transfer protein, cytoplasmic 1 (2)" | downexpressed |
| Hs.546392 | PLAC8 | Placenta-specific 8 (1) | overexpressed |
| Hs.437009 | POLG2 | "Polymerase (DNA directed), gamma 2, accessory subunit (1)" | downexpressed |
| Hs.458336 | POPDC3 | Popeye domain containing 3 (2) | downexpressed |
| Hs.153310 | PREX1 | "Phosphatidylinositol 3,4,5-trisphosphate-dependent RAC exchanger 1 (1)" | downexpressed |
| Hs.256067 | PRKAA2 | "Protein kinase, AMP-activated, alpha 2 catalytic subunit (1)" | overexpressed |
| Hs.446240 | PRKCBP1 | Protein kinase C binding protein 1 (1) | downexpressed |
| Hs.555950 | PRRX2 | Paired related homeobox 2 (1) | downexpressed |
| Hs.445857 | PRSS12 | "Protease, serine, 12 (neurotrypsin, motopsin) (2)" | downexpressed |
| Hs.149473 | PRSS7 | "Protease, serine, 7 (enterokinase) (1)" | overexpressed |
| Hs.434255 | PSD3 | Pleckstrin and Sec7 domain containing 3 (1) | downexpressed |
| Hs.79033 | QPCT | Glutaminyl-peptide cyclotransferase (glutaminyl cyclase) (1) | downexpressed |
| Hs.7482 | RBM19 | RNA binding motif protein 19 (1) | overexpressed |
| Hs.507866 | RGC32 | Response gene to complement 32 (1) | downexpressed |
| Hs.445030 | RHOBTB3 | Rho-related BTB domain containing 3 (1) | downexpressed |
| Hs.35861 | RIS1 | Ras-induced senescence 1 (1) | downexpressed |
| Hs.524809 | RSN | Restin (Reed-Steinberg cell-expressed intermediate filament-associated protein) (1) | downexpressed |
| Hs.28491 | SAT | Spermidine/spermine N1-acetyltransferase (2) | downexpressed |
| Hs.374180 | SCAMP5 | Secretory carrier membrane protein 5 (1) | overexpressed |
| Hs.224607 | SDC1 | Syndecan 1 (1) | overexpressed |
| Hs.252451 | SEMA3A | "Sema domain, immunoglobulin domain (Ig), short basic domain, secreted, (semaphorin) 3A (2)" | downexpressed |
| Hs.440932 | SEPT9 | Septin 9 (1) | downexpressed |
| Hs.381167 | SERPINB1 | "Serpin peptidase inhibitor, clade B (ovalbumin), member 1 (1)" | overexpressed |
| Hs.502829 | SF1 | Splicing factor 1 (1) | downexpressed |
| Hs.213424 | SFRP1 | Secreted frizzled-related protein 1 (1) | downexpressed |
| Hs.374257 | SIAT4A | "ST3 beta-galactoside alpha-2,3-sialyltransferase 1 (1)" | downexpressed |
| Hs.101307 | SLC14A1 | "Solute carrier family 14 (urea transporter), member 1 (Kidd blood group) (1)" | downexpressed |
| Hs.518089 | SLC15A2 | "Solute carrier family 15 (H+/peptide transporter), member 2 (1)" | downexpressed |
| Hs.443572 | SLC22A5 | "Solute carrier family 22 (organic cation transporter), member 5 (1)" | downexpressed |
| Hs.516866 | SLC23A2 | "Solute carrier family 23 (nucleobase transporters), member 2 (1)" | downexpressed |
| Hs.250083 | SLC9A2 | "Solute carrier family 9 (sodium/hydrogen exchanger), member 2 (1)" | downexpressed |
| Hs.535801 | SLC9A3 | "Solute carrier family 9 (sodium/hydrogen exchanger), member 3 (1)" | downexpressed |
| Hs.517070 | SLPI | Secretory leukocyte peptidase inhibitor (1) | downexpressed |
| Hs.349470 | SNCG | "Synuclein, gamma (breast cancer-specific protein 1) (1)" | overexpressed |
| Hs.487046 | SOD2 | "Superoxide dismutase 2, mitochondrial (2)" | downexpressed |
| Hs.98367 | SOX17 | SRY (sex determining region Y)-box 17 (1) | overexpressed |
| Hs.2316 | SOX9 | "SRY (sex determining region Y)-box 9 (campomelic dysplasia, autosomal sex-reversal) (1)" | downexpressed |
| Hs.111779 | SPARC | "Secreted protein, acidic, cysteine-rich (osteonectin) (1)" | downexpressed |
| Hs.129794 | SPATA12 | Spermatogenesis associated 12 (1) | overexpressed |
| Hs.558463 | SPEN | "Spen homolog, transcriptional regulator (Drosophila) (1)" | overexpressed |
| Hs.71465 | SQLE | Squalene epoxidase (1) | downexpressed |
| Hs.25590 | STC1 | Stanniocalcin 1 (2) | downexpressed |
| Hs.233160 | STC2 | Stanniocalcin 2 (1) | downexpressed |
| Hs.24553 | STRA6 | Stimulated by retinoic acid gene 6 homolog (mouse) (1) | downexpressed |
| Hs.508958 | STXBP6 | Syntaxin binding protein 6 (amisyn) (1) | overexpressed |
| Hs.480615 | SYNPO2 | Synaptopodin 2 (1) | overexpressed |
| Hs.503998 | TAGLN | Transgelin (1) | overexpressed |
| Hs.129895 | TBX3 | T-box 3 (ulnar mammary syndrome) (2) | overexpressed |
| Hs.2012 | TCN1 | "Transcobalamin I (vitamin B12 binding protein, R binder family) (1)" | downexpressed |
| Hs.473152 | TFAP2C | Transcription factor AP-2 gamma (activating enhancer binding protein 2 gamma) (1) | downexpressed |
| Hs.79353 | TFDP1 | Transcription factor Dp-1 (1) | downexpressed |
| Hs.438231 | TFPI2 | Tissue factor pathway inhibitor 2 (1) | downexpressed |
| Hs.2030 | THBD | Thrombomodulin (1) | downexpressed |
| Hs.7337 | TMEM19 | Transmembrane protein 19 (1) | overexpressed |
| Hs.143250 | TNC | Tenascin C (hexabrachion) (2) | downexpressed |
| Hs.556258 | TncRNA | Trophoblast-derived noncoding RNA (1) | downexpressed |
| Hs.211600 | TNFAIP3 | "Tumor necrosis factor, alpha-induced protein 3 (2)" | downexpressed |
| Hs.437322 | TNFAIP6 | "Tumor necrosis factor, alpha-induced protein 6 (1)" | downexpressed |
| Hs.149168 | TNFRSF19 | "Tumor necrosis factor receptor superfamily, member 19 (1)" | downexpressed |

TABLE 9-continued

List of 286 genes having altered expression in resistant cells

| Unigene ID | Gene | Name (No. of clones) | Status in resistant cells |
|---|---|---|---|
| Hs.478275 | TNFSF10 | "Tumor necrosis factor (ligand) superfamily, member 10 (1)" | downexpressed |
| Hs.554791 | TP53I11 | Tumor protein p53 inducible protein 11 (1) | downexpressed |
| Hs.201482 | TPD52L1 | Tumor protein D52-like 1 (1) | overexpressed |
| Hs.416436 | TRIM50A | DKFZp434A0131 protein (1) | downexpressed |
| Hs.12084 | TUFM | "Tu translation elongation factor, mitochondrial (1)" | downexpressed |
| Hs.524187 | TULP3 | Tubby like protein 3 (1) | downexpressed |
| Hs.6651 | VAMP4 | Vesicle-associated membrane protein 4 (1) | downexpressed |
| Hs.109225 | VCAM1 | Vascular cell adhesion molecule 1 (1) | downexpressed |
| Hs.469244 | WASF2 | "WAS protein family, member 2 (1)" | downexpressed |
| Hs.36688 | WFDC1 | WAP four-disulfide core domain 1 (1) | downexpressed |
| Hs.105633 | WINS1 | Lines homolog 1 (*Drosophila*) (1) | overexpressed |
| Hs.492974 | WISP1 | WNT1 inducible signaling pathway protein 1 (1) | downexpressed |
| Hs.152213 | WNT5A | "Wingless-type MMTV integration site family, member 5A (2)" | downexpressed |
| Hs.529901 | XIST | X (inactive)-specific transcript (2) | downexpressed |
| Hs.48589 | ZNF228 | Zinc finger protein 228 (1) | overexpressed |
| Hs.434401 | ZNF638 | Zinc finger protein 638 (1) | downexpressed |
| Hs.521064 | ZNF655 | Zinc finger protein 655 (1) | downexpressed |
| Hs.367688 | | CDNA clone IMAGE: 4794726 (1) | downexpressed |
| Hs.25318 | | Clone 25194 mRNA sequence (1) | downexpressed |
| Hs.271721 | | "*Homo sapiens*, clone IMAGE: 4179986 (1)" | downexpressed |
| Hs.404514 | | Transcribed locus (1) | downexpressed |
| Hs.124776 | | CDNA clone IMAGE: 4152983 (1) | downexpressed |
| Hs.484885 | | CDNA clone IMAGE: 5531727 (2) | downexpressed |
| Hs.87606 | | "Transcribed locus, weakly similar to XP_496827.1 PREDICTED: similar to LINE-1 reverse transcriptase homolog [*Homo sapiens*] (1)" | downexpressed |
| Hs.102336 | | Rho GTPase activating protein 8 (1) | downexpressed |
| Hs.105316 | | Transcribed locus (1) | downexpressed |
| Hs.567557 | | Transcribed locus (1) | downexpressed |
| Hs.156737 | | Transcribed locus (1) | downexpressed |
| Hs.191582 | | Hypothetical gene supported by AK001829 (1) | downexpressed |
| Hs.409967 | | Transcribed locus (1) | downexpressed |
| Hs.514903 | | Hypothetical LOC388480 (1) | downexpressed |
| Hs.523529 | | Similar to Formin binding protein 2 (srGAP2) (1) | downexpressed |
| Hs.560535 | | Transcribed locus (1) | downexpressed |
| Hs.356225 | | "Golgi autoantigen, golgin subfamily a, 8B (1)" | downexpressed |
| Hs.563454 | | **Full-length cDNA clone CS0DF028YB15 of Fetal brain of *Homo sapiens* (human) (1) | downexpressed |
| Hs.550126 | | "CDNA FLJ45989 fis, clone RECTM2001307 (1)" | downexpressed |
| Hs.113418 | | LOC441801 (1) | downexpressed |
| Hs.382827 | | Similar to Zinc-alpha-2-glycoprotein precursor (Zn-alpha-2-glycoprotein) (Zn-alpha-2-GP) (1) | downexpressed |
| Hs.59203 | | Transcribed locus (1) | downexpressed |
| Hs.122011 | | "Transcribed locus, strongly similar to XP_526752.1 PREDICTED: similar to hypothetical protein FLJ33167 [Pan troglodytes] (1)" | overexpressed |
| Hs.536912 | | Transcribed locus (1) | overexpressed |
| Hs.558980 | | Germline transcript of Ig heavy chain variable region (V) (1) | overexpressed |
| Hs.281207 | | Hypothetical LOC400236 (1) | overexpressed |
| Hs.130074 | | Similar to F4N2.10 (1) | overexpressed |
| Hs.537276 | | Transcribed locus (1) | overexpressed |
| Hs.529274 | | Transcribed locus (1) | overexpressed |
| Hs.41829 | | Transcribed locus (1) | overexpressed |
| Hs.98945 | | "*Homo sapiens*, clone IMAGE: 5744200, mRNA (1)" | overexpressed |
| Hs.560769 | | **Transcribed locus (1) | overexpressed |
| Hs.148647 | | Transcribed locus (1) | overexpressed |
| Hs.416043 | | Hypothetical LOC401491 (1) | overexpressed |

Microarrays

In one preferred embodiment, a microarray having a large number of human genes is analyzed for the expression of a characteristic set of genes shown here to be associated with resistance. This list of genes is found in the "Table of Resistance Genes", Table 9. This table indicates each gene by UNigene ID and accepted gene name in Geribank/EMBL/DDBJ. The table further shows whether the gene is downexpressed or upexpressed in resistance. Therefore, one may use the present expression signature of 288 genes which may be contained in a microarray having a wide sampling of all human genes, such as the Agilent Human 1B Oligo Microarray Kit, the GeneChip Human Genome U133A 2.0 Array, or the Stanford reporter based microarray (HEEBO). Each of the 288 genes listed has been shown to be statistically significantly varied between alkylating agent (BRDU or TMZ) sensitive and resistant cells.

Further description on the preparation of microarrays is found in U.S. Pat. Nos. 5,716,785, 5,891,636, and 5,807,522. The '522 patent which was issued to Stanford University. The patent covers methods for fabricating microarrays for applications such as gene expression analysis. The '522 patent describes technology used to print microarrays at densities greater than 100 polynucleotides per cm². The above patents are hereby incorporated by reference as teaching the making and using of microarrays in expression analysis. Further description is found in U.S. Pat. No. 6,004,755, also incorporated here by reference.

Multiplex PCR and Microarrays

In addition, a collection of probes or primers for multiplex PCR may be made. In this case, a smaller set of probes is desirable. However, a smaller set of probes from a larger microarray may also be analyzed. The most significantly variable gene expression was found for the following genes, which are all down expressed in resistant cells:

TABLE 10

Most Significant Genes

| Unigene ID | Gene | Name (Number of clones) |
| --- | --- | --- |
| Hs.211600 | TNFAIP3 | Tumor necrosis factor, alpha-induced protein 3 |
| Hs.81328 | NFKBIA | Nuclear factor of kappa light polypeptide gene enhancer in B-cells inhibitor, alpha |
| Hs.283683 | C8orf4 | Chromosome 8 open reading frame 4 |
| Hs.2250 | LIF | Hypothetical protein MGC20647 |
| Hs.501522 | MGMT | O-6-methylguanine-DNA methyltransferase |
| Hs.148074 | Beta4GalNAc-T4 | Beta1,4-N-acetylgalactosaminyltransferases IV |
| Hs.224607 | SDC1 | Syndecan 1 |
| Hs.502328 | CD44 | CD44 antigen (homing function and Indian blood group system) |
| Hs.403933 | FBXO32 | F-box protein 32 |
| Hs.462086 | RIP | RPA interacting protein |
| Hs.355141 | TNIP1 | TNFAIP3 interacting protein 1 |
| Hs.458276 | NFKBIE | Nuclear factor of kappa light polypeptide gene enhancer in B-cells inhibitor, epsilon |
| Hs.9731 | NFKBIB | Nuclear factor of kappa light polypeptide gene enhancer in B-cells inhibitor, beta |
| Hs.368551 | TNIP2 | TNFAIP3 interacting protein 2 |

The UniGene database contains sets of non-redundant gene-oriented sequence clusters. It is created through automatic partitioning of GenBank sequences, and each UniGene cluster represents a unique gene. See world wide web ncbi.nlm.nih.gov. In addition to the UniGene table, the Gene Database also contains relationship tables relating the UniGene clusters to GenBank Accession numbers, Entrez Gene ID's and so on. For example, the UniGene-GenBank relationship table stores all the GenBank Accession numbers associated with each UniGene cluster.

Currently four different chemistries, TaqMan® (Applied Biosystems, Foster City, Calif., USA), Molecular Beacons, Scorpions® and SYBR® Green (Molecular Probes), are available for real-time PCR. All of these chemistries allow detection of PCR products via the generation of a fluorescent signal. TaqMan probes, Molecular Beacons and Scorpions depend on Forster Resonance Energy Transfer (FRET) to generate the fluorescence signal via the coupling of a fluorogenic dye molecule and a quencher moeity to the same or different oligonucleotide substrates. SYBR Green is a fluorogenic dye that exhibits little fluorescence when in solution, but emits a strong fluorescent signal upon binding to double-stranded DNA.

TaqMan probes are oligonucleotides that have a fluorescent reporter dye attached to the 5' end and a quencher moeity coupled to the 3' end. These probes are designed to hybridize to an internal region of a PCR product. In the unhybridized state, the proximity of the fluor and the quench molecules prevents the detection of fluorescent signal from the probe. During PCR, when the polymerase replicates a template on which a TaqMan probe is bound, the 5'-nuclease activity of the polymerase cleaves the probe. This decouples the fluorescent and quenching dyes and FRET no longer occurs. Thus, fluorescence increases in each cycle, proportional to the amount of probe cleavage.

Like TaqMan probes, Molecular Beacons also use FRET to detect and quantitate the synthesized PCR product via a fluor coupled to the 5' end and a quench attached to the 3' end of an oligonucleotide substrate. Unlike TaqMan probes, Molecular Beacons are designed to remain intact during the amplification reaction, and must rebind to target in every cycle for signal measurement. Molecular Beacons form a stem-loop structure when free in solution. Thus, the close proximity of the fluor and quench molecules prevents the probe from fluorescing. When a Molecular Beacon hybridizes to a target, the fluorescent dye and quencher are separated, FRET does not occur, and the fluorescent dye emits light upon irradiation.

Molecular Beacons, like TaqMan probes, can be used for multiplex assays by using spectrally separated fluor/quench moieties on each probe. As with TaqMan probes, Molecular Beacons can be expensive to synthesize, with a separate probe required for each target.

TaqMan probes, Molecular Beacons and Scorpions allow multiple DNA species to be measured in the same sample (multiplex PCR), since fluorescent dyes with different emission spectra may be attached to the different probes. Multiplex PCR allows internal controls to be co-amplified and permits allele discrimination in single-tube, homogeneous assays. These hybridization probes afford a level of discrimination impossible to obtain with SYBR Green, since they will only hybridize to true targets in a PCR and not to primer-dimers or other spurious products.

Finally, a single gene may be used in a real time quantitative PCR assay to determine if it is lower than a standard expression level. In this case, the preferred gene is TNFAIP3.

Stanley et al., "Multiplexed tandem PCR: gene profiling from small amounts of RNA using SYBR Green detection," Nucleic Acids Research 2005 33(20):e180; doi: 10.1093/nar/gni 182, Published online 24 Nov. 2005, describes a method that was shown to measure the levels of expression of 72 different genes from human breast cells. Further description of a format for using the presently described primers in a multiplex PCR is found in Tabiti, Karim et al. US. Nov. 20, 2003 U.S. 20030215830, "Quantitative multiplex PCR with high dynamic range," the description of which is hereby incorporated by reference.

Obtaining Sequences for Arrays and Per Primers

Nucleic acid primers, probes or array targets may be designed based solely on the identification of the sequences given herein. For example, using Table 9, one may obtain the sequence of TNFAIP3 by going to the NCBI website (http://www.ncbi.nlm.nih.gov/entrez/query.fcgi?CMD=Pager&DB=nucleotide) and searching "UNIGENE" for the gene identifier, in this case TNFAIP3. One then selects from the results sequence 211600, or any desired TNFAIP3 mRNA, cDNA (including EST) or peptide sequence.

Preferably, the primers will be designed to amplify cDNA prepared from the mRNA expressed in the cell to be evaluated. However, it is also contemplated that homogenous assays may be used to obviate any amplification of the target or the signal. A recently developed approach is based on fluorescence correlation spectroscopy (FCS). This expression assay is based on gene-specific hybridization of two dye-labeled DNA probes to a selected target molecule (either DNA or RNA) in solution. The subsequent dual color cross-correlation analysis allows the quantification of the bio-molecule of interest in absolute numbers. See Current Pharmaceutical Biotechnology, Volume 5, Number 2, April 2004, pp. 191-197(7).

Primers may be designed by inputting the sequence to be analyzed into one of the known primer design tools, such as: Primer 3, http://frodo.wi.mit.edu/cgi-bin/primer3/primer3_www.cgi; FastPCR, available from the University of Helsinki; Genefisher, http://bibiserv.techfak.uni-bielefeld.de/genefisher/; or PCRNOW™ primer design tool, http://pathogene.swmed.edu/rt_primer/. Primers need not amplify the entire cDNA, merely a segment selected on the basis of size, invariability from patient to patient, or other design choice.

Modulation of Resistant Phenotype

Since it has now been shown that low levels of expression of TNFAIP3, NFKBIA. and other genes as described above are associated with resistance to alkylating agents, novel methods and materials may be implemented to increase TNFAIP3 or NFKBIA activity in cells to be treated with the alkylating agent. These methods include the administration to the cells of TNFAIP3 or NFKBIA polypeptides (either full length protein or active fragments) and delivery to cells of nucleic acids encoding TNFAPI3 or NFKBIA polypeptides. It is contemplated that patients with glioblastomas will receive gene therapy including such nucleic acids. A discussion of gene therapy of the brain is found in Lam, P., "Potential of gene therapy for brain tumors," *Human Molecular Genetics,* 2001, Vol. 10, No. 7 777-787, which teaches the following:

Both the IL-4R and TfR (transferring receptor) are expressed at high levels on human glioma cells and the TfR is also high on the luminal surface of brain capillaries. These receptors may be used for targeting in gene therapy. For example, an envelope protein of the retrovirus virion may be fused to a polypeptide that binds to one of these receptors. Ligands or receptor antibodies have also been added to the capsid of adenovirus (Ad) virions to enhance infection of glioma cells, e.g. antibodies to EGFR, which is expressed at high levels on GBM, a peptide selected for binding to the TfR, a lysine polypeptide and ligands that target heparin sulfate and integrin receptors. Biologically active proteins, such as β-galactosidase and viral thymidine kinase (TK) have been fused to translocating peptides/proteins, such as TAT or VP22, to allow their movement out of the cell of synthesis into neighboring cells.

Non-viral vectors useful for delivering the present nucleic acids include naked DNA, polycationic polymers and liposomes. These vectors are delivered into the tissue by injection or particle bombardment and typically enter the cytoplasm by endocytosis or transient membrane disruption. Transduction efficiency is increased by incorporation of fusion proteins and targeting elements. DNA transit to the nucleus can be facilitated by high mobility group proteins and nuclear localization signals and viral elements can also be included to prolong DNA stability.

Virus vectors have a high efficiency of gene delivery and multiple therapeutic capabilities. Most of the viruses used for gene delivery are common human pathogens with a broad host cell range. The commonly used viral vectors for gene delivery into brain tumors include the recombinant HSV, Ad. retrovirus and hybrid vectors derived from them. Gutless Ad, HSV amplicon and AAV vectors, which like retrovirus vectors express no viral genes, have less potential toxicity, but reduced transduction efficiency. Retrovirus vectors have been the mainstay for most clinical gene therapy protocols and have special appeal for brain tumors given that the classic Moloney Murine Leukemia Virus type can only insert genes into dividing cells, such as tumor and endothelial cells within the neovasculature in the adult brain. Since these vectors tend to have very low titers and are unstable in body fluids, they have been delivered by grafting in vector producer cells, injecting virions pseudotyped with vesicular stomatitis virus glycoprotein (VSVG) to stabilize the virions or packaged in human cells, or by converting tumor cells to producer cells.

Direct, stereotactic injection is the most common route of delivery, with the volume and number of injections being limited by inherent toxicity of fluids and the potential for hemorrhage. The number of vectors, delivery period and range of gene delivery can be increased by slow and convection-enhanced delivery, incorporation of stable virus particles into biodegradable microspheres and pre-exposure to proteases to degrade extracellular matrix proteins. Still, in most schemes the vector only diffuses a few millimeters from the injection site.

The trans-cranial injection of viral gene therapy vectors is clearly effective, including primate models, and allows for the local production of therapeutic genes. The single injection into the human or animal brain of either adenovirus or herpes simplex virus results in inflammatory reaction leading to astrogliosis and demyelination and more recent viral gene therapy approaches employ either adeno-associated virus (AAV) or retrovirus. AAV vectors generally need to be given at some repeat intervals, and 90% of the human population has a pre-existing immunity to AAV. Both AAV and retrovirus permanently and randomly integrate into the host genome. Neither AAV nor retrovirus crosses the BBB. Therefore, it is necessary to administer the virus via craniotomy and an intracerebral injection.

As described in Pardridge, Neurorx. 2005 Jan.; 2(1): 129-138, "Tyrosine Hydroxylase Replacement in Experimental Parkinson's Disease with Transvascular Gene Therapy," exogenous genes incorporated in plasmid DNA can be widely distributed throughout the entire brain after an intravenous injection with the use of a form of transvascular gene transfer technology that uses pegylated immunoliposomes, or PILs. The plasmid DNA is encapsulated in the interior of a 100-nm liposome. The surface of the liposome is decorated with several thousand strands of 2000-Da polyethyleneglycol (PEG), and this pegylation process alters the surface of the liposome such that the liposome is not rapidly cleared by the reticuloendothelial system after an intravenous administration. The pegylated liposome is relatively inert and does not cross the blood brain barrier (BBB). However, transvascular transport of the PIL can be induced by conjugating receptor specific monoclonal antibodies (mAbs) to the tips of 1-2% of the PEG tails so that each 100-nm liposome is conjugated with approximately 50 mAb molecules. The transferrin receptor (TfR) or the insulin receptor is expressed at both the BBB and on neuronal cell membranes. Therefore, a PIL, targeted with a mAb to either the TfR or the insulin receptor, is able to undergo sequential receptor-mediated transcytosis across the BBB, followed by receptor-mediated endocytosis into neurons. The PIL rapidly enters the nuclear compartment after endocytosis into the cell, as demonstrated by confocal microscopy.

Gene therapy to the brain is further described in Ningya Shi and William M. Pardridge, "Noninvasive gene targeting to the brain," *Proc Natl Acad Sci USA,* 2000 Jun. 20; 97(13): 7567-7572 (2000) and in U.S. Pat. No. 6,372,250 to Pardridge, issued Apr. 16, 2002 and hereby incorporated by reference in its entirety. Its disclosure describes the preparation of a receptor specific liposome, which may be used to deliver a nucleic acid according to the present invention.

It is also contemplated that TNFAIP3 or NFKBIA may be upregulated in cells resistant to alkylating agents by drugs that increase transcription of this gene or translation of the corresponding mRNA. Such drugs include TNFAIP3 or NFKBIA transcription factors, and small molecules that act as transcription factors. Methods for screening for such molecules are described in USPGPUB 20050079496 to Serfling, et al. published Apr. 14, 2005, entitled "Methods for diagnosing and treating neoplasias using nf-at transcriptions factors," hereby incorporated by reference for teaching how to identify and modulate transcription factors. Although the transcription factors discussed there relate to lymphomas, those skilled in the art will appreciate that such methods may be adapted to TNFAIP3 or NFKBIA as well, given the present disclosure.

Kits

Kits may be prepared which contain reagents useful in the practice of the present invention. For example, a kit may be prepared using certain materials provided in a Roche Lightcycler kit, except that the kit is directed to detection of mRNA's as described above.

The kit allows quantification of TNFAIP3 or NFKBIA mRNA relative to the housekeeping gene porphobilinogen deaminase (PBGD) in research samples obtained from cell cultures and other biological samples, such as clinical samples obtained from tumor debulking. In the first step, cDNA is reverse transcribed from RNA using AMV reverse transcriptase and random hexamer priming. In the second step, a 100-200 bp fragment of TNFAIP3 or NFKBIA-encoding mRNA is amplified from the cDNA by hot start PCR. Fluorescence detection of the amplicon is accomplished using a specific pair of hybridization probes.

The kit is function-tested using calibration RNA derived from an immortalized cell lines that are known to be sensitive and resistant. The amount of mRNA encoding for TNFAIP3 or NFKBIA is expressed as a relative ratio to a reference gene (PBGD) in a sample, compared to the TNFAIP3: PBGD ratio in the calibrator. The quantity of TNFAIP3 or NFKBIA and PBGD is a function of the PCR efficiency and the sample crossing point, and does not require a standard curve for its determination. Normalization against the Calibrator RNA corrects for differences in TNFAIP3 or NFKBIA values, resulting from the combined variation in the quantity and quality of the RNA sample and the efficiency of PCR.

The kit is designed for 96 reactions (for a maximum of 39 samples) with a final reaction volume of 20 µl each. This is intended to be compatible with standard 96 well microtiter plates, but other formats may be designed. It employs the Hot Start PCR technique, which prevents the elongation of non-specific primer-template hybrids that may form at lower temperatures. The primer and hybridization probe mixes are supplied as convenient premixed reagents. Contamination risk is minimized by the instrument's closed-tube, real-time fluorescence detection system.

Microarray Kits

Microarrays are known in the art and are described in detail in U.S. Pat. No. 6,973,388 to Friend, et al., issued Dec. 6, 2005, entitled "Methods of diagnosing disease states using gene expression profiles," hereby incorporated by reference as describing microarray preparation and use. Briefly, microarrays consist of a surface to which probes that correspond in sequence to gene products (e.g., cDNAs, mRNAs, cRNAs, polypeptides, and fragments thereof), can be specifically hybridized or bound at a known position. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site" (hereinafter, "site") is a nucleic acid or nucleic acid analogue to which a particular cognate cDNA can specifically hybridize. The nucleic acid or analogue of the binding site can be, e.g., a synthetic oligomer, a full-length cDNA, a less-than full-length cDNA, or a gene fragment.

Although in a preferred embodiment the microarray contains binding sites for products of all or almost all genes listed herein, and controls, such comprehensiveness is not necessarily required. Usually the microarray will have binding sites corresponding to at least TNFAIP3, RIP, C8ORF, NFKBIA, NFKBIE, SCD1, CD44, TNIP1, TNIP2, and FBXO32. A gene to be included in the microarray is prepared from an open reading frame (ORF) of preferably at least 50, 75, or 99 amino acids. The "binding site" to which a particular cognate cDNA specifically hybridizes is usually a nucleic acid or nucleic acid analogue attached at that binding site. The binding sites of the microarray may include, in addition to the particular genes of interest described here, almost any number of desired additional genes and controls, up to each gene in an organism's genome. These DNAs can be obtained by, e.g., polymerase chain reaction (PCR) amplification of gene segments from genomic DNA, cDNA (e.g., by RT-PCR), or cloned sequences. PCR primers are chosen, based on the known sequence of the genes or cDNA that result in amplification of unique fragments (i.e., fragments that do not share more than 10 bases of contiguous identical sequence with any other fragment on the microarray). Computer programs are useful in the design of primers with the required specificity and optimal amplification properties. See, e.g., Oligo version 5.0 (National Biosciences). In the case of binding sites corresponding to very long genes, it will sometimes be desirable to amplify segments near the 3' end of the gene so that when oligo-dT primed cDNA probes are hybridized to the microarray, less-than-full length probes will bind efficiently. Typically each gene fragment on the microarray will be between about 50 bp and about 2000 bp, more typically between about 100 bp and about 1000 bp, and usually between about 300 bp and about 800 bp in length. PCR methods are well known and are described, for example, in Innis et al. eds., 1990, PCR Protocols: A Guide to Methods and Applications, Academic Press Inc. San Diego, Calif., which is incorporated by reference in its entirety for all purposes. It will be apparent that computer controlled robotic systems are useful for isolating and amplifying nucleic acids.

Antibody Kits

Antibodies to TNFAIP3 are commercially available, e.g., from Abcam plc., Cambridge, England. These antibodies may be used to evaluate TNFAIP3 protein levels in cells through staining with a labeled antibody. The cells may be evaluated microscopically, or by automated methods such as cell sorting.

Immunohistochemistry is used for localization of TNFAIP3 antigens in tissue sections of tumors by the use of labeled antibodies as specific reagents through antigen-antibody interactions that are visualized by a marker such as fluorescent dye, enzyme, radioactive element or colloidal gold. Tissue preparation is the cornerstone of immunohistochemistry. To ensure the preservation of tissue architecture and cell morphology, prompt and adequate fixation is essential. Many antigens can be successfully demonstrated in formalin-fixed paraffin-embedded tissue sections. Antigen retrieval techniques may further enhance the use of formalin as routine fixative for immunohistochemistry. Background staining may be specific or non-specific. Inadequate or delayed fixation may give rise to false positive results due to the passive uptake of serum protein and diffusion of the antigen. Such false positives are common in the center of large tissue blocks or throughout tissues in which fixation was delayed. Special controls must be run in order to test the protocols and for the specificity of the antibody being used.

Positive Control is to test for a protocol or procedure used. It will be ideal to use the tissue of known positive as a control. If the positive control tissue showed negative staining, the protocol and procedure need to be checked until a good positive staining is obtained.

Negative Control is to test for the specificity of the antibody involved. First, no staining must be shown in the omission of the primary antibody or the replacement of the specific primary antibody by a normal serum (must be the same species as primary antibody). This control is easy to achieve and can be used routinely in immunohistochemical staining.

Direct method is one step staining method, and involves a labeled antibody (i.e., FITC conjugated antiserum) reacting directly with the antigen in tissue sections. This technique utilizes only one antibody and the procedure is short and quick. However, it is insensitive due to little signal amplification and rarely used since the introduction of indirect method.

Indirect method involves an unlabeled primary antibody (first layer) which reacts with tissue antigen, and a labeled secondary antibody (second layer) react with primary antibody (Note: The secondary antibody must be against the IgG of the animal species in which the primary antibody has been raised). This method is more sensitive due to signal amplification through several secondary antibody reactions with different antigenic sites on the primary antibody. In addition, it is also economic since one labeled second layer antibody can be used with many first layer antibodies (raised from the same animal species) to different antigens.

The second layer antibody can be labeled with a fluorescent dye such as FITC, rhodamine or Texas red, and this is called indirect immunofluorescence method. The second layer antibody may be labeled with an enzyme such as peroxidase, alkaline phosphatase or glucose oxidase, and this is called indirect immunoenzyme method.

It is also preferred to stain for two or more antigens as listed in Table 9 in one common tissue section. This can be achieved by immunofluorescence method using different fluorescent dyes. Multiple staining can also be done with peroxidase conjugated antibodies developed with different chromogen substrates to produce the end products of different colors.

CONCLUSION

The present examples, methods, procedures, specific compounds and molecules are meant to exemplify and illustrate the invention and should in no way be seen as limiting the scope of the invention, which is defined by the literal and equivalent scope of the appended claims. Any patents or publications mentioned in this specification are indicative of levels of those skilled in the art to which the patent pertains and are intended to convey details of the invention which may not be explicitly set out but would be understood by workers in the filed. Such patens or publications are hereby incorporated by reference to the same extent as if each was specifically and individually incorporated by reference and for the purpose of describing and enabling the method or material referred to.

REFERENCES

1. C. Y. Wang, J. C. Cusack, Jr., R. Liu et al., *Nat Med* 5 (4), 412 (1999); Y. Pommier, O. Sordet, S. Antony et al., *Oncogene* 23 (16), 2934 (2004).
2. A. W. Opipari, Jr., M. S. Boguski, and V. M. Dixit, *J Biol Chem* 265 (25), 14705 (1990).
3. E. G. Lee, D. L. Boone, S. Chai et al., *Science* 289 (5488), 2350 (2000).
4. V. G. Tusher, R. Tibshirani, and G. Chu, *Proc Natl Acad Sci USA* 98 (9), 5116 (2001).
5. I. E. Wertz, K. M. O'Rourke, H. Zhou et al., *Nature* 430 (7000), 694 (2004).
6. J. B. Friedman, E. B. Brunschwig, P. Platzer et al., *Int J Cancer* 111 (1), 72 (2004).
7. K. Nakashima, M. Yanagisawa, H. Arakawa et al., *FEBS Lett* 457 (1), 43 (1999).
8. C. Mauro, F. Pacifico, A. Lavorgna et al., *The Journal of biological chemistry* 281 (27), 18482 (2006).
9. S. Van Huffel, F. Delaei, K. Heyninck et al., *The Journal of biological chemistry* 276 (32), 30216 (2001).
10. M. Klinkenberg, S. Van Huffel, K. Heyninck et al., *FEBS letters* 498 (1), 93 (2001).
11. J. D. Cheng, R. P. Ryseck, R. M. Attar et al., *The Journal of experimental medicine* 188 (6), 1055 (1998).
12. J. E. Thompson, R. J. Phillips, H. Erdjument-Bromage et al., *Cell* 80 (4), 573 (1995).
13. P. J. Chiao, S. Miyamoto, and I. M. Verma, *Proceedings of the National Academy of Sciences of the United States of America* 91 (1), 28 (1994).
14. A. Hoffmann, A. Levchenko, M. L. Scott et al., *Science* 298 (5596), 1241 (2002).

What is claimed is:

1. A method for identifying a therapeutically responsive phenotype in a brain tumor cell, comprising the step of measuring a level of expression of TNFAIP3 gene, NFKBIA gene, TNIP1 gene and TNIP2 genes in the cell and identifying said cell as being sensitive or resistant to an alkylating agent based on said level of expression of TNFAIP3 gene, NFKBIA gene, TNIP1 gene, and TNIP2 genes, wherein a responsive phenotype has more expression of TNIP1, TNFAIP3, NFKBIA and TNIP2 than a resistant phenotype.

2. The method of claim 1 wherein the level of expression of the gene is measured by determining a level of mRNA encoding the gene.

3. The method of claim 2 wherein the measurement of mRNA comprises the step of real-time reverse transcription PCR.

4. The method of claim 2 wherein the measurement of mRNA comprises the step of using a microarray.

5. The method of claim 1 where the measuring of the expression of the gene comprises determining a level of the cognate protein in the cell.

6. The method of claim 1 further comprising the step of measuring the level of expression of at least three genes selected from the group consisting of C8orf4, MGMT, Beta4GalNAc-T4, SDC1, CD44, FBXO32, RIP, NFKBIE, and NFKBIB.

7. A method for identify an alkylating agent resistance phenotype in a brain tumor cell, comprising the step of measuring a level of expression of a TNFAIP3 gene in the cell, wherein a resistant phenotype is identified us having said alkylating agent resistance phenotype based on less expression of TNFAIP3 than a sensitive phenotype and said measuring includes measurement of expression of a control gene, which is selected from the group consisting of: PBGD (porphobilinogen deaminase). 5-aminolevulinate synthase (ALAS), beta actin, and Glyceraldehyde-3-phosphate dehydrogenase (GAPDH).

8. A method for assessing probability of survival time of a patient with a brain tumor, comprising: obtaining a cell from the tumor; and measuring, a level of expression of genes TNFAIP3, SDC1, CD44 and FBXO32 in the cell, wherein shortened survival is based on a lowered level of expression of all four genes.

9. The method of claim 8 further comprising the step of measuring the level of expression of at least one gene selected from the group consisting of NFKBIA, C8orf4, LIF, MGMT, Beta4GalNAc-T4, RIP, TNIP1, NFKBIE, NFKBIB, and TNIP2.

10. The method of claim 9 wherein the measurement of level of expression comprises the measurement of mRNA levels using a microarray.

* * * * *

UNITED STATES PATENT AND TRADEMARK OFFICE
CERTIFICATE OF CORRECTION

PATENT NO. : 7,875,274 B2  Page 1 of 1
APPLICATION NO. : 11/638161
DATED : January 25, 2011
INVENTOR(S) : Branimir Sikic and Markus Bredel It is certified that error appears in the above-identified patent and that said Letters Patent is hereby corrected as shown below:

Column 51, line 40, Claim 6, after "C8orf4," insert --LIF,--.
    Column 52, line 19, Claim 7, replace "us" with --as--.
    Column 52, line 24, Claim 7, replace "deaminase)." with --deaminase)--.
    Column 52, line 30, Claim 8, after measuring delete ",".

Signed and Sealed this

Thirteenth Day of November, 2012

David J. Kappos
*Director of the United States Patent and Trademark Office*